(12) United States Patent
Katzhendler et al.

(10) Patent No.: US 9,428,448 B2
(45) Date of Patent: Aug. 30, 2016

(54) COMPOUNDS AND METHODS OF TREATING OBESITY

(71) Applicants: Yissum Research Development Company of the Hebrew University of Jerusalem Ltd., Jerusalem (IL); Al-Quds University, Jerusalem (IL)

(72) Inventors: Jehoshua Katzhendler, Jerusalem (IL); Meir Saidian, Jerusalem (IL); Yousef Najajreh, Beit Jala (IL); Raphael Mevorach, Efrat (IL); Elliot Berry, Jerusalem (IL); Yosefa Avraham, Jerusalem (IL)

(73) Assignees: Yissum Research Development Company of the Hebrew University of Jerusalem Ltd., Jerusalem (IL); Al-Quds University, Jerusalem (IL)

( * ) Notice: Subject to any disclaimer, the term of this patent is extended or adjusted under 35 U.S.C. 154(b) by 0 days.

(21) Appl. No.: 14/314,228

(22) Filed: Jun. 25, 2014

(65) Prior Publication Data

US 2014/0309273 A1 Oct. 16, 2014

Related U.S. Application Data

(63) Continuation of application No. 12/920,637, filed as application No. PCT/IL2009/000247 on Mar. 4, 2009, now abandoned.

(60) Provisional application No. 61/033,438, filed on Mar. 4, 2008.

(51) Int. Cl.
| | | |
|---|---|---|
| *A61K 31/164* | (2006.01) | |
| *A61K 31/325* | (2006.01) | |
| *C07C 235/28* | (2006.01) | |
| *C07C 233/91* | (2006.01) | |
| *C07C 271/02* | (2006.01) | |
| *C07C 235/06* | (2006.01) | |
| *C07C 235/08* | (2006.01) | |
| *C07C 271/16* | (2006.01) | |
| *C07C 53/126* | (2006.01) | |
| *C07C 233/20* | (2006.01) | |
| *C07C 233/22* | (2006.01) | |
| *C07D 207/08* | (2006.01) | |

(52) U.S. Cl.
CPC .......... *C07C 271/02* (2013.01); *A61K 31/164* (2013.01); *A61K 31/325* (2013.01); *C07C 53/126* (2013.01); *C07C 233/20* (2013.01); *C07C 233/22* (2013.01); *C07C 235/06* (2013.01); *C07C 235/08* (2013.01); *C07C 235/28* (2013.01); *C07C 271/16* (2013.01); *C07D 207/08* (2013.01)

(58) Field of Classification Search
CPC .............. A61K 31/164; A61K 31/325; C07C 235/28; C07C 233/91
See application file for complete search history.

(56) References Cited

U.S. PATENT DOCUMENTS

| 5,506,224 A | 4/1996 | Della Valle et al. |
|---|---|---|
| 5,618,955 A | 4/1997 | Mechoulam et al. |
| 6,410,597 B1 | 6/2002 | Bieberich et al. |
| 2005/0020679 A1 | 1/2005 | Makriyannis et al. |

FOREIGN PATENT DOCUMENTS

| BE | 663371 A | 11/1965 |
|---|---|---|
| DE | 19544635 A1 | 6/1997 |
| EP | 0 161 422 A1 | 11/1985 |
| EP | 0 201 743 A2 | 11/1986 |
| EP | 0 208 961 A2 | 1/1987 |
| EP | 0 421 441 A2 | 4/1991 |
| EP | 0 682 011 A1 | 11/1995 |
| EP | 1 527 776 A1 | 5/2005 |
| JP | 02235862 A | 9/1990 |
| WO | 94/12466 A1 | 6/1994 |
| WO | 95/08529 A1 | 3/1995 |
| WO | 96/18391 A2 | 6/1996 |
| WO | 97/00852 A1 | 1/1997 |
| WO | 01/01980 A1 | 1/2001 |
| WO | 02/29001 A2 | 4/2002 |
| WO | 2005/046580 A2 | 5/2005 |
| WO | 2005/115370 A2 | 12/2005 |
| WO | 2006/044381 A2 | 4/2006 |
| WO | 2008/021625 A2 | 2/2008 |
| WO | 2009/073788 A1 | 6/2009 |
| WO | 2009/09973 A2 | 9/2009 |
| WO | 2009/125409 A2 | 10/2009 |
| WO | 2011/027373 A1 | 3/2011 |
| WO | 2013/025399 A1 | 2/2013 |
| WO | 2013/063263 A1 | 5/2013 |

OTHER PUBLICATIONS

Kubinyi (3D QSAR in Drug Design: Ligand-Protein Interactions and Molecular Similarity, vol. 2-3, Springer, 1998, 800 pages). p. 243-44 provided.*
Wermuth, The Practice of Medicinal Chemsitry, 2d ed. (2003), 768 pages. Chs. 9-10 provided.*
Lynch et al. (Prostaglandins & other Lipid Mediators 64 (2001) 33-45).*
Gardell et al. (Trends in Molecular Medicine, vol. 12, Issue 2, Feb. 2006, pp. 65-75).*
Smith et al. (Inorg. Chem., v. 16, n. 3, 1977, p. 558-562).

(Continued)

*Primary Examiner* — Robert Havlin

(74) *Attorney, Agent, or Firm* — Vorys, Sater, Seymour and Pease LLP

(57) ABSTRACT

Provided are new fatty acid derivatives, methods for their preparation, pharmaceutical compositions including such compounds, and methods of using these compounds and compositions, e.g., as agents for the treatment of obesity and related disorders, and for improving cognition.

5 Claims, 17 Drawing Sheets

(56) References Cited

OTHER PUBLICATIONS

Abadji, Vasiliki et al., (1994) (R)-methanandamide: a chiral novel anandamide possessing higher potency and metabolic stability. J. Med. Chem 37(12):1889-1893.

Astarita, Giuseppe et al., (2006) Pharmacological Characterization of Hydrolysis-Resistant Analogs of Oleoylethanolamide with Potent Anorexiant Properties. J. Pharmacol. Exp. Ther. 318(2):563-570.

Avraham, Yosefa et al., (1996) Behavioral and neurochemical alterations caused by diet restriction—the effect of tyrosine administration in mice. Brain Research 732(1-2):133-144.

Berge, Stephen M. et al., (1977) Pharmaceutical salts. J. of Pharm. Sol. 66(1):1-19.

Bieberich, Erhard et al., (2002) Synthesis and characterization of novel ceramide analogs for induction of apoptosis in human cancer cells. Cancer Letters 181(1):55-64.

Boring, D. L. et al., (1996) Cerebrodiene, arachidonyl-ethanolamide, and hybrid structures: potential for interaction with brain cannabinoid receptors. Prostaglandins Leukotrienes Essential Fatty Acids 55(3):207-210.

De Lago, Eva et al., (2004) In vivo pharmacological actions of two novel inhibitors of anandamide cellular uptake. Eur. J. Pharmachol. 484(2-3):249-257.

Di Marzo, Vincenzo at al., (2004) The anandamide membrane transporter. Structure-activity relationships of anandamide and oleoylethanolamine analogs with phenyl rings in the polar head group region. Bioorg. & Med. Chem. 12(19):5161-5169.

Fontana, A. et al., (1995) Analysis of anandamide, an endogenous cannabinoid substance, and of other natural Nacylethanolamines. Prostaglandins Leukotrienes and Essential Fatty Acids 53(4):301-308.

Hanus, Lumir et al., (1993) Two new unsaturated fatty acid ethanolamides in brain that bind to the cannabinoid receptor. J. Med. Chem., 36(20):3032-3034.

Houseknecht, Karen L. et al., (2002) Peroxisome proliferator-activated receptor gamma (PPARgamma) and its ligands: a review. Domestic Animal Endocrinology 22(1):1-23.

Jonsson, Kent-Olov et al., (2001) Effects of homologues and analogues of palmitoylethanolamide upon the inactivation of the endocannabinoid anandarnide. British Journal Pharmacology 133(8):1263-1275.

Khanolkar, Atmaran D. et al., (1996) Head group analogs of arachidonylethanolamide, the endogenous cannabinoid ligand. J. Med. Chem. 39(22):4515-4519.

Koutek, Bohumir et al., (1994) Inhibitors of arachidonoyl ethanolamide hydrolysis. J. Biol. Chem. 269(37) 22937-22940.

Kozak, Kevin R. et al., (2003) Amino acid determinants in cyclooxygenase-2 oxygenation of the endocannabinoid anandamide. Biochemistry 42(30): 9041-9049.

Lambert, Didier M. et al., (1999) Analogues and homologues of N-palmitoylethanolamide, a putative endogenous CB2 cannabinoid, as potential ligands for the cannabinoid receptors. Biochimica at Biophysica Acta 1440(2-3):266-274.

Lambert, Didier M. et al., (2002) The palmitoylethanolamide family: a new class of anti-inflammatory agents? Current Medicinal Chemistry 9(6):663-674.

Lang, Wensheng et al., (1999) Substrate Specificity and Stereoselectivity of Rat Brain Microsomal Anandamide Amidohydrolase. J. Med. Chem. 42(5):896-902.

Ligresti, Alessia et al., (2004) Further evidence for the existence of a specific process for the membrane transport of anandamide. Biochem. J. 380(1):265-272.

Lin, Sonyuan et al., (1998) Novel analogues of arachidonylethanolamide (anandamide): affinities for the CB1 and CB2 cannabinoid receptors and metabolic stability. J. Med. Chem. 41(27):5353-5361.

Lo Verme, J. et al., (2005) Regulation of food intake by oleoylethanolamide. Cellular and Molecular Life Sciences 62 (6):708-716.

Ortar, Giorgio et al., (2003) Novel selective and metabolically stable inhibitors of anandamide cellular uptake. Biochem. Pharmacol. 65(9):1473-1481.

Parkkari, Teija et al., (2004) Synthesis and CB1 receptor activities of novel arachidonyl alcohol derivatives. Bioorganic & Medicinal Chemistry Letters 14(12):3231-3234.

Qin, Ce et al., (1998) Determination of anandamide amidase activity using ultraviolet-active amine derivatives and reverse-phase high-performance liquid chromatography. Analytical Biochemistry 261(1):8-15.

Ryan, William J. et al., (1997) Potent anandamide analogs: the effect of changing the length and branching of the end pentyl chain. J. Med. Chem. 40(22):3617-3625.

Schiano Moriello, Aniello et al., (2006) Development of the first potential covalent inhibitors of anandamide cellular uptake. J. Med. Chem. 49(7)2320-2332.

Sheskin, Tzviel et al., (1997) Structural requirements for binding of anandamide-type compounds to the brain cannabinoid receptor. J. Med. Chem. 40(5):659-667.

Sugiura, Takayuki et al., (1995) 2-Arachidonoylglycerol: a possible endogenous cannabinoid receptor ligand in brain. Biochem. Biophys. Res. Commun. 215(1):89-97.

Wolf, Anne M. & Colditz, Graham A. (1998) Current estimates of the economic cost of obesity in the United States. Obesity Research 6(2):97-106.

Database CA [Online] Chemical Abstracts Service, Columbus, Ohio, US; Achinami, Kazuo et al: "Preparation of pyrrolidines and their use as pharmaceuticals" XP002537770 retrieved from STN Database accession No. 1991:143131 & JP 02 235862 A (Sapporo Breweries Ltd., Japan) Sep. 18, 1990.

Database CA [Online] Chemical Abstracts Service, Columbus, Ohio, US; Weil, J. K. et al: "Tallow alkanolamides. Preparation and effect on surfactant solutions" XP002550980 retrieved from STN Database accession No. 1972:87536 & Journal of the American Oil Chemists' Society, 48(11), 674-7 CODEN: JAOCA7; ISSN: 0003-021X, 1971.

Database CA [Online] Chemical Abstracts Service, Columbus, Ohio, US; Ben-Bassat, Albert A. et al: "Quantitative monitoring of stearic acid monoalkanolamide syntheses by HPLC" XP002550981 retrieved from STN Database accession No. 1986:417544 & Journal of Liquid Chromatography, 9(1), 89-101 CODEN: JLCHD8; ISSN: 0148-3919, 1986.

Database CA [Online] Chemical Abstracts Service, Columbus, Ohio, US; Ziedler, Juergen et al: "Synthesis of heterocyclic platelet activating factor analogs" XP002550982 retrieved from STN Database accession No. 1995:471236 & Chemistry and Physics of Lipids, 75(2), 183-91 CODEN: CPLIA4; ISSN: 0009-3084, 1995.

Database CA [Online] Chemical Abstracts Service, Columbus, Ohio, US; Van Overloop, Helena et al: "Further characterization of mammalian ceramide kinase: substrate delivery and (stereo)specificity, tissue distribution, and subcellular localization studies" XP002550983 retrieved from STN Database accession No. 2006:132163 & Journal of Lipid Research, 47(2), 268-283 CODEN: JLPRAW; ISSN: 0022-2275, 2006.

Database CA [Online] Chemical Abstracts Service, Columbus, Ohio, US; Mazzeo, Jeffrey R. et al: "Chiral surfactants and methods for their use in chiral separations" XP002550984 retrieved from STN Database accession No. 1995:957946 & WO 95/08529 A1 (Waters Corp., USA) Mar. 30, 1995.

ISR of PCT/IL2009/000247 mailed Nov. 11, 2009.

IUPAC, Compendium of Chemical Terminology, 2nd ed. (the "Gold Book"). Compiled by A. D. McNaught and A. Wilkinson. Blackwell Scientific Publications, Oxford (1997). Excerpt from updated online version.

Beers et al., "236/Menopause", The Merck Manual of Diagnosis and Therapy, 17th Edition, 1999, Merck Research Laboratories, Whitehouse Station N.J., pp. 1942-1944.

(56) References Cited

OTHER PUBLICATIONS

Avraham et al., "Novel Acylethanolamide Derivatives That Modulate Body Weight through Enhancement of Hypothalamic Pro-Opiomelanocortin (POMC) and/or Decreased Neuropeptide Y (NPY)", J. Medicinal Chemistry, vol. 56, pp. 1811-1829, (2013).

Crupi et al., "N-palmitoylethanolarnide Treatment Exhibits Antidepressant Effects in a Mouse Model of Anxiety/Depressive Like Behavior", FASEB Journal, vol. 26, one page, (2012).

Guida et al., "Palmitoylethanolamide (Normast(R)) in chronic neuropathic pain by compressive type lumbosciatalgia: Multicentric clinical study", Database accession No. EMB-2010313306, Dolor 2010 Publicaciones Permanyer ESP, vol. 25, No. 1, pp. 35-42, (2010).

Garza et al., "Leptin restores adult hippocampal neurogenesis suppressed by chronic unpredictable stress and reverses glucocorticoid-induced inhibition of GSK3β/β-catenin signaling", Mol Psychiatry, Jul. 2012, vol. 17, No. 8, pp. 790-808.

Zhang et al., "The Mechanism of Action of Thyroid Hormones", Annu. Rev. Physiol., 2000, vol. 62, pp. 439-466.

Merenlender-Wagner et al., "The β-Endorphin Role in Stress-Related Psychiatric Disorders", Current Drug Targets, 2009, vol. 10, pp. 1096-1108.

Avraham et al., "Management of Obesity in Menopause: Lifestyle Modification, Medication, Bariatric Surgery and Personalized Treatment", Current Topics in Menopause, Chapter 7, pp. 143-162, (2012).

International Preliminary Report on Patentability for International Application No. PCT/IL2013/050618, eleven pages, issued Jan. 20, 2015.

* cited by examiner

COMPOUNDS AND METHODS OF TREATING OBESITY

FIELD OF THE INVENTION

The present invention relates to a novel family of fatty acid derivatives which regulate food consumption and body weight as well as improve cognitive function. The compounds of the invention are therefore useful in methods of treating or reducing the severity of obesity or a complication of obesity, increasing or facilitating weight loss, inhibiting or reducing appetite, decreasing food consumption and body mass index (BMI), and improving cognitive function.

BACKGROUND OF THE INVENTION

Obesity is a nutritional disorder in western societies, and is a serious health concern because of its association with diseases and conditions such as adult-onset diabetes, hypertension, and heart disease. Obesity is currently described by the World Health Organization (WHO) as an epidemic in many industrialized nations, and it has recently been reported by the Worldwatch Institute in Washington D.C., that over 1 billion people worldwide are now suffering from the health consequences of over-consumption. In the United States alone, where more than one in three adults are classified as obese, the condition is estimated to cause 300,000 premature deaths each year. The costs associated with obesity and its related illnesses causes a significant debt in the US economy—both from the direct cost of treating conditions triggered by obesity, and from the lost in economic productivity (Wolf, A. M. & Colditz, G. A. *Obes. Res.* 6, 97-106 (1998)).

Previous studies have shown that cannabinoids and their antagonists may regulate feeding and body weight through activation or inhibition of cannabinoid receptor type 1 (CB1) like Anandamide or Rimonabant (SR141716A) respectively, or by activation of PPAR-α (peroxisome proliferator activate receptor alpha), a key regulator of lipid metabolism and energy balance in mammals. Oleoylethanolamide (OEA) is a naturally occurring lipid amide that reduces food intake, promotes lipolysis and decreases body weight gain in rodents by activating PPAR-α. The biological deactivation of OEA is not fully understood but is likely to involve the enzymatic hydrolysis of this lipid amide to oleic acid and ethanolamine. Two structurally distinct OEA-hydrolyzing enzymes have been characterized: fatty-acid amide hydrolase (FAAH), an intracellular membrane-bound serine hydrolase, and N-acetylethanoamine-hydrolyzing acid amidase, a lysosomal cysteine hydrolase. Giuseppe et al. (*J. Pharm. Exper. Therap.* 318 (2), pp. 563-570, 2006), describe OEA analogs that resist enzymatic hydrolysis, activate PPAR-α, and reduce feeding when administered to rodents in vivo either parenterally or orally. The most potent of these compounds, (Z)—(R)-9-octadecenamide, N-2(hydroxyethyl,1-methyl) (KDS-5104), is reported to stimulate transcriptional activity of PPAR-α with an EC50 of 100 nm.

Obesity, if left unabated, can have dire health consequences, such as adult-onset diabetes (Type II diabetes), dyslipidemia, hyperinsulinemia, hypertension, heart disease (e.g., coronary heart disease, hear attack, heart failure or heart arrhythmias), thromboembolism, osteoarthritis, gout, varicose veins, increased incidence of stroke, low self esteem, hirsutism, sweating, hypoventilation, sleep apnea, respiratory problems, breathlessness, cancer (including breast cancer, cancer of the colon, cancer of the uterus and cancer of the pancreas), kidney disease, gallstones, gallbladder disease, infertility, problems with pregnancy, menorrhagia, and accelerated morbidity and mortality. Innovative approaches are urgently needed at both the basic science and clinical levels to treat obesity.

SUMMARY OF THE INVENTION

The present invention relates to a novel family of fatty acid derivatives (e.g., oleoyl ethanolamide derivatives and related structures), which regulate food consumption and body weight. The compounds of the invention are useful in methods of treating or reducing the severity of obesity or a complication of obesity, increasing or facilitating weight loss, inhibiting or reducing appetite, and decreasing food consumption and body mass index (BMI). The compounds of the invention also improve cognitive function and are thus useful in the treatment of diseases and conditions associated with decreased cognitive function.

As demonstrated herein, the applicants identified novel fatty acid derivatives, e.g., oleoyl-valinol ((Z-Octadec)-9-enoic acid 1-hydroxymethyl-2-methyl-propyl)-amide, designated herein "Compound X"), which regulate food consumption, body weight, and improve cognitive function. Compound X has been shown to cause immediate decrease in body weight, which was related to a decrease in food consumption, increased activity, decreased brain 2-Arachidonoyl glycerol (2-AG) levels and increased Serotonin (5-HT) levels in the hypothalamus. Treatment with Compound X also resulted in significant improvement in cognitive function as evaluated by an 8 arm maze, and this correlated with the increase in norepinephrine (NE) levels in the hippocampus and hypothalamus. The effect of Compound X resembles the effect of moderate caloric restriction (to 60%) which has previously been shown to be beneficial (Avraham Y., Bonne O B, Berry E. M., 1996. Behavioral and neurochemical alterations caused by diet restriction—The effect of tyrosine administration in mice. *Brain Research* 732, 133-144). Compound X has superior activity and reduced side effects as compared with Rimonabant, another anti-obesity drug formerly on the market.

The compounds of the invention are derived from fatty acids (e.g., oleic acid) or their amino or alcohol derivatives (e.g., oleyl amine or oleyl alcohol respectively), and hydroxy amino acids derived from natural or unnatural amino acids, or substituted amino alcohols. The compounds are represented by general formula (I):

FA-A-B    (I)

wherein
A is:

1)

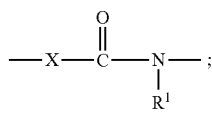

2)

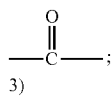

3)

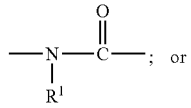 ; or

4)

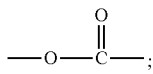

B is

1)

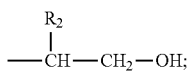

2)

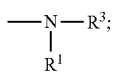

3)

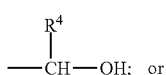

or

4)

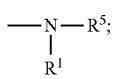

FA is a residue of a fatty acid selected from the group consisting of oleic acid (oleoyl), elaidic acid (elaidoyl), linoleic acid (linoleoyl), gamma-linoleic acid (gamma-linoleoyl), alpha-linoleic acid (alpha-linoleoyl), eicosapentaenoic acid (eicosapentaenoyl), docosahexaenoic acid (docosahexaenoyl), arachidonic acid (arachidonyl), palmitic acid (palmitoyl), palmitoleic acid (palmitoleoyl), stearic acid (stearoyl), myristic acid (myristoyl), lauric acid (lauroyl), and tetradec-7-enoic acid (tetradec-7-enoyl), or the residue of an amine or alcohol derivative of any of the foregoing fatty acids;

X is O, $NR^1$ or a bond;

$R^1$ is independently at each occurrence H or $CH_3$;

$R^2$ is selected from the group consisting of:

1) the residue of an (L)- or (D)-amino acid when $R^1$ is H, or of an (L)- or (D)-N-methyl amino acid when $R^1$ is $CH_3$, provided that, for compounds wherein A is

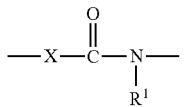

and B is

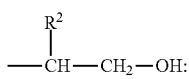

(i) when X is a bond, $R^1$ is H and FA is the residue of oleic acid, the amino acid is not glycine, alanine, serine, tyrosine, phenylalanine or cysteine;
(ii) when X is a bond, $R^1$ is H and FA is the residue of arachidonic acid, the amino acid is not glycine, alanine, tyrosine or phenylalanine;
(iii) when X is a bond, $R^1$ is H and FA is the residue of palmitic acid, myristic acid or stearic acid, the amino acid is not glycine;
(iv) when X is a bond, $R^1$ is H and FA is the residue of linoleic acid, the amino acid is not glycine or alanine;
(v) when X is a bond, $R^1$ is H and FA is the residue of elaidic acid, the amino acid is not glycine or serine; and
(vi) when X is a bond, $R^1$ is $CH_3$ and FA is the residue of oleic acid, the N-methyl amino acid is not sarcosine;

2) when $R^1$ is H, the residue of an unnatural amino acid selected from the group consisting of Dap, dimethyl Dap, dimethylamino lysine, Dab, 2-pyridyl alanine, 3-pyridyl alanine, 1-naphthyl alanine, 2-naphthyl alanine, homoarginine, citrulline, phenylglycine, norleucine, ornithine, Abu, Apn, Ahx, 4-halo phenyl alanine, 4-amino phenyl alanine and 4-nitro phenylalanine; or when $R^1$ is $CH_3$, the N-methyl derivatives of the any of the foregoing amino acids, provided that, for compounds wherein A is

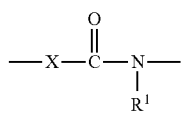

and B is

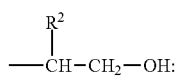

(i) when X is a bond, and FA is the residue of oleic acid or arachidonic acid, the amino acid is not phenylglycine; and
(ii) when X is a bond and FA is the residue of elaidic acid, the amino acid is not Ahx;

or $R^1$ and $R^2$, together with the nitrogen and carbon to which they are respectively attached, can form a heterocycle selected from:

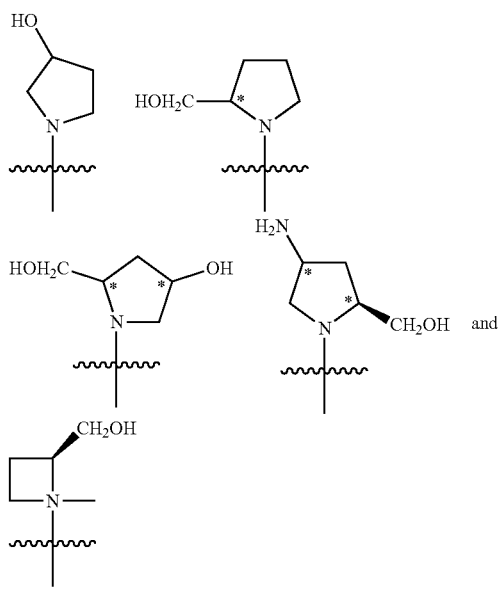

provided that when FA is the residue of oleic acid or arachidonic acid and X is a bond, R¹ and R² together with the nitrogen and carbon to which they are respectively attached are not

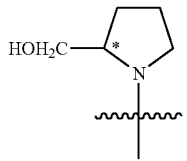

R³ is selected from the group consisting of:

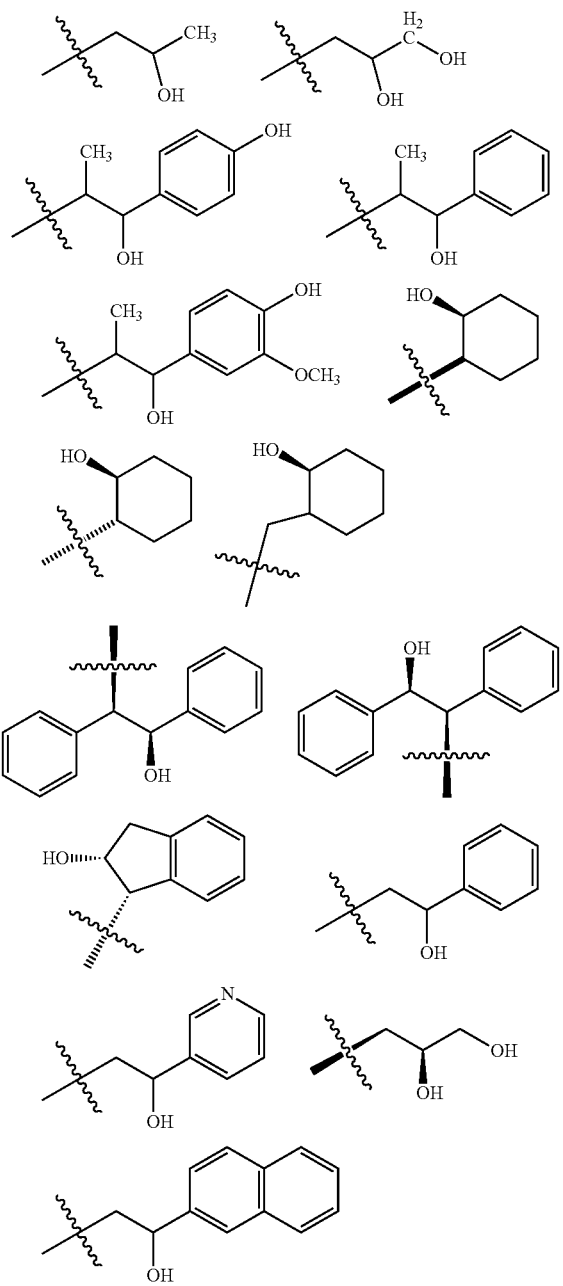

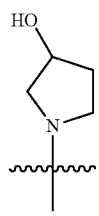 [SMILES: *N1CCC(O)C1]

and

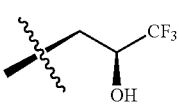

or R¹ and R³, together with the nitrogen to which they are attached, can form a group represented by the structure:

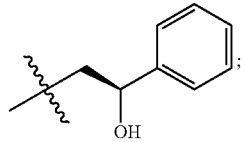 [SMILES: *C[C@H](O)c1ccccc1]

provided that, for compounds wherein A is

and B is

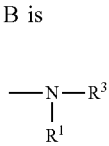

(i) when FA is the residue of oleic acid or arachidonic acid and R¹ is H, R³ is not

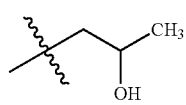 [SMILES: *CC(C)O]

and (ii) when FA is the residue of arachidonic acid and R¹ is H, R³ is not

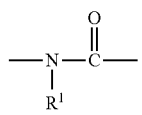

R⁴ the residue of an (L)- or (D)-amino acid, provided that, for compounds wherein A is

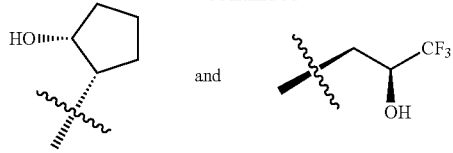

and B is

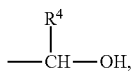

R¹ is H and FA is the residue of oleic acid, the amino acid is not glycine or alanine; and R⁵ is selected from the group consisting of:

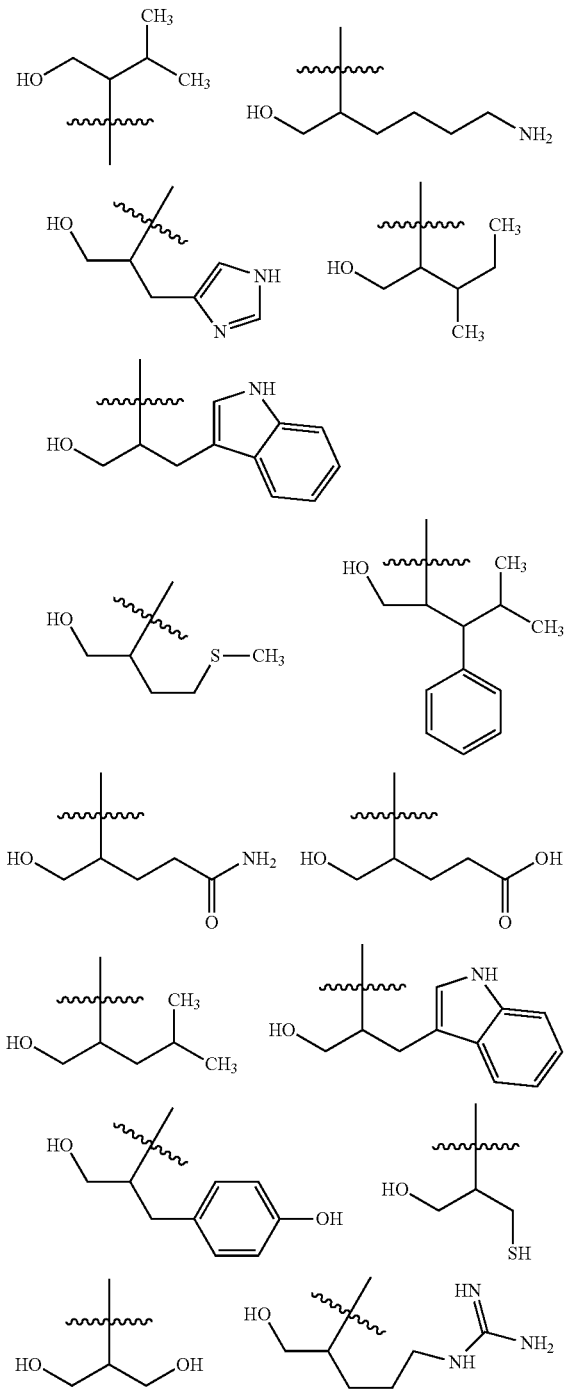

-continued

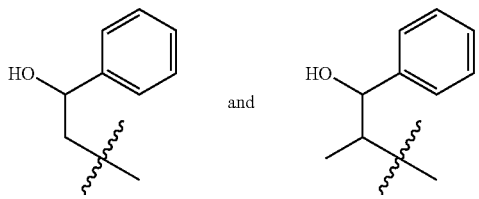

or R¹ and R⁵, together with the nitrogen to which they are attached, can form a heterocycle selected from:

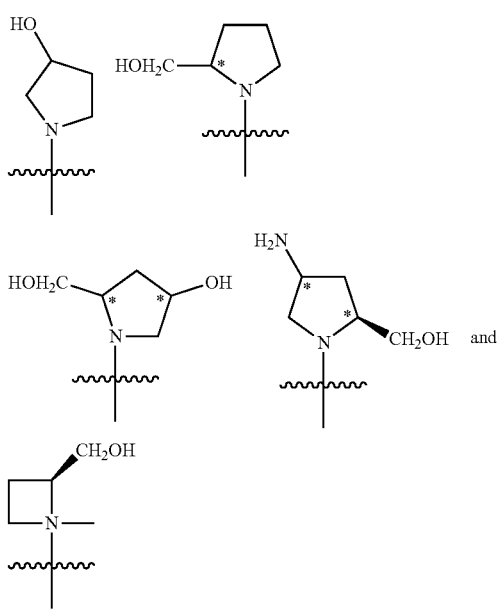

including salts, hydrates, solvates, polymorphs, optical isomers, geometrical isomers, enantiomers, diastereomers, and mixtures thereof.

In several embodiments, the compounds of general formula (I) are represented by any one or more of the following structures:

A)

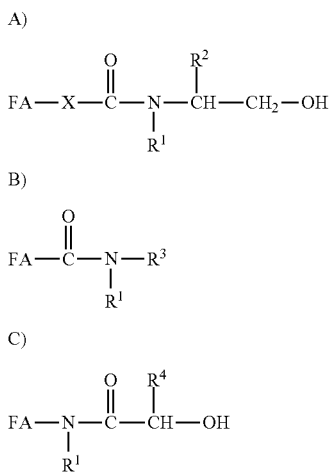

B)

C)

-continued

D) 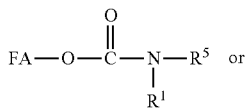

E) 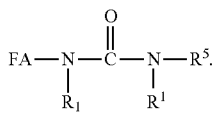

including salts, hydrates, solvates, polymorphs, optical isomers, geometrical isomers, enantiomers, diastereomers, and mixtures thereof.

In one embodiment, FA is the residue of oleic acid (9Z-octadecenoic acid), referred to herein as "oleoyl". In another embodiment, FA is the residue of elaidic acid (9E-octadecenoic acid), referred to hereinafter as "elaidoyl". In another embodiment, FA is the residue of linoleic acid (9Z,12Z-octadecadienoic acid or (9E,12E-octadecadienoic acid), referred to herein as "linoleoyl". In another embodiment, FA is a residue of gamma-linoleic acid (all-Z-6,9,12-octadecatrienoic acid or all-E-6,9,12-octadecatrienoic acid), referred to herein as "gamma-linoleoyl". In another embodiment, FA is a residue of alpha-linoleic acid (all-cis-9,12,15-octadecatrienoic acid), referred to herein as "alpha-linoleoyl". In another embodiment, FA is a residue of eicosapentaenoic acid ((5Z,8Z,11Z,14Z,17Z)-icosa-5,8,11,14,17-pentaenoic acid) or ((5E,8E,11E,14E,17E)-icosa-5,8,11,14,17-pentaenoic acid), referred to herein as "eicosapentaenoyl". In another embodiment, FA is a residue of docosahexaenoic acid ((4Z,7Z,10Z,13Z,16Z,19Z)-docosa-4,7,10,13,16,19-hexaenoic acid) or ((4E,7E,10E,13E,16E,19E)-docosa-4,7,10,13,16,19-hexaenoic acid), referred to herein as "docosahexaenoyl". In another embodiment, FA is a residue of stearic acid (octadecanoic acid), referred to herein as "stearoyl". In another embodiment, the FA is a residue of palmitic acid (hexadecanoic acid), referred to herein as "palmitoyl". In another embodiment, FA is the residue of arachidonic acid (all-Z-5,8,11,14-eicosatetraenoic acid) or all E-5,8,11,14-eicosatetraenoic acid, referred to herein as "arachidonoyl". In another embodiment, FA is the residue of myristic acid (tetradecanoic acid), referred to herein as "myristoyl". In another embodiment, FA is the residue of Z- or E-tetradec-7-enoic acid. In another embodiment, FA is an amine derivative of any of the foregoing acids (e.g., oleyl amine when FA is oleic acid; linoleyl amine when FA is linoleic acid etc.). In another embodiment, FA is an alcohol derivative of any of the foregoing acids (e.g., oleyl alcohol when FA is oleic acid; linoleyl alcohol when FA is linoleic acid etc.).

In one particular embodiment, the present invention provides a compound of the formula:

A) 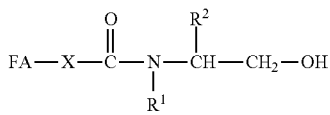

wherein X, $R^1$ and $R^2$ are defined above. In one embodiment, X in Formula A is a bond, and the compound is represented by the structure:

A1) 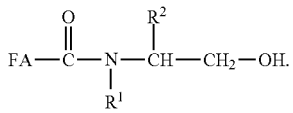

In accordance with this embodiment, the compound is derived from a residue of a fatty acid as described above, bonded by its carboxyl moiety to the amino group of a substituted amino alcohol. In one aspect of the aforementioned embodiment, $R^1$ in H. In accordance with this embodiment, $R^2$ can be the residue of a naturally occurring (L)-amino acid or the residue of a (D)-amino acid. Non-limiting examples of such amino acids include glycine ($R^2$=H), alanine ($R^2$=$CH_3$), cysteine ($R^2$=$CH_2SH$), tyrosine ($R^2$=$CH_2$-4-hydroxyphenyl), phenylalanine ($R^2$=$CH_2$-phenyl), serine ($R^2$=$CH_2OH$), homoserine ($R^2$=$CH_2CH_2OH$), glutamic acid ($R^2$=$CH_2CH_2COOH$), valine ($R^2$=$CH(CH_3)_2$), arginine ($R^2$=$CH_2CH_2CH_2NHC(=NH)NH_2$), ornithine ($R^2$=$CH_2CH_2CH_2NH_2$), lysine ($R^2$=$CH_2CH_2CH_2CH_2NH_2$), threonine ($R^2$=$CH(CH_3)(OH)$), methionine ($R^2$=$CH_2CH_2SCH_3$), tryptophan ($R^2$=$CH_2$-1H-indol-3-yl)), histidine ($R^2$=$CH_2$-imidazolyl), aspartic acid ($R^2$=$CH_2COOH$) and isoleucine ($R^2$=$CH(CH_3)CH_2CH_2CH_3$). In a currently preferred embodiment, $R^2$ is the residue of (L)-valine. In one particular embodiment when $R^1$ in H and FA is the residue of oleic acid, the amino acid is not glycine, alanine, serine, tyrosine, phenylalanine or cysteine. In another particular embodiment when $R^1$ in H and FA is the residue of arachidonic acid, the amino acid is not glycine, alanine, tyrosine or phenylalanine. In another embodiment when $R^1$ in H and FA is the residue of palmitic acid, myristic acid or stearic acid, the amino acid is not glycine. In another embodiment when $R^1$ in H and FA is the residue of linoleic acid, the amino acid is not glycine or alanine. In another embodiment when $R^1$ is H and FA is the residue of elaidic acid, the amino acid is not glycine or serine.

In another embodiment, $R^1$ is $CH_3$. In accordance with this embodiment, $R^2$ can be the residue of an N-methyl(L)-amino acid or the residue of an N-methyl(D)-amino acid. Non-limiting examples of such N-methyl amino acids include N-methyl serine ($R^2$=$CH_2OH$), N-methyl alanine ($R^2$=$CH_3$), N-methyl leucine ($R^2$=$CH_2CH(CH_3)_2$); N-methyl isoleucine ($R^2$=$CH(CH_3)CH_2CH_3$), sarcosine ($R^2$=H), N-methyl phenylalanine ($R^2$=$CH_2$-phenyl), and N-methyl aspartic acid ($R^2$=$CH_2COOH$). In one embodiment when $R^1$ is $CH_3$ and FA is the residue of oleic acid, the N-methyl amino acid is not sarcosine ($R^2$=H).

In another embodiment, when $R^1$ is H, $R^2$ is the residue of an unnatural amino acid. Non-limiting examples of such amino acids or residues thereof include Dap ($R^2$=$CH_2NH_2$), dimethyl Dap ($R^2$=$CH_2N(CH_3)_2$), dimethylamino lysine ($R^2$=$(CH_2)_4$—$N(CH_3)_2$), Dab ($R^2$=$CH_2CH_2NH_2$), 2-pyridyl alanine ($R^2$=$CH_2$-2-pyr), 3-pyridyl alanine ($R^2$=$CH_2$-3-pyr), 1-napthyl alanine ($R^2$=$CH_2$-1-napthyl), 2-naphthyl alanine ($R^2$=$CH_2$-2-naphthyl), homoarginine ($R^2$=$(CH_2)_4$—NH—C(N=H)$NH_2$), citrulline ($R^2$=$(CH_2)_4$—NH—C(=O)$NH_2$), phenylglycine ($R^2$=phenyl), norleucine ($R^2$=$(CH_2)_3$—$CH_3$), ornithine ($R^2$=($CH_2$)$_3$—$NH_2$), Abu ($R^2$=$CH_2CH_3$), Apn ($R^2$=$CH_2CH_2CH_3$), Ahx ($R^2$=($CH_2$)$_3$—$CH_3$), 4-halo phenyl alanine (e.g., 4-fluoro, bromo, chloro or iodo phenylalanine wherein $R^2$=$CH_2$-4-halophenyl), 4-amino phenylalanine ($R^2$=$CH_2$-4-$NH_2$-phenyl) and 4-nitro phenylalanine ($R^2$=$CH_2$-4-$NO_2$-phenyl). In one embodiment wherein $R^1$ is H and FA is the residue of oleic acid or arachidonic acid, the amino acid is not phenylglycine. In another embodiment wherein $R^1$ is H and FA is the residue of elaidic acid, the amino acid is not Ahx. In another embodiment, when $R^1$ is $CH_3$, $R^2$ can be the residue of N-methyl amino acid having any of the aforementioned residues.

In another embodiment, $R^1$ and $R^2$, together with the nitrogen and carbon to which they are respectively attached, can form a proline residue or a derivative thereof, represented by any one or more of the structures:

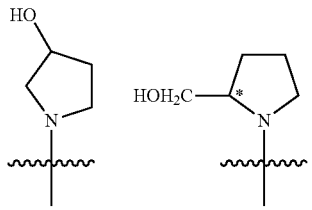

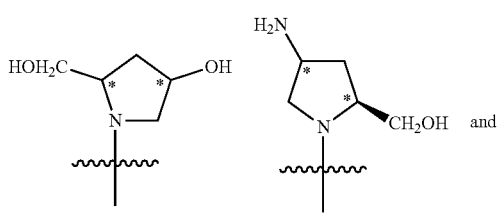

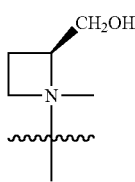

In one embodiment wherein $R^1$ is H and FA is the residue of oleic acid or arachidonic acid, $R^1$ and $R^2$ together with the nitrogen and carbon to which they are respectively attached are not

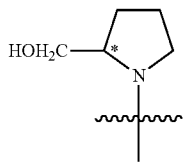

In one particularly preferred embodiment $R^1$ is H, and $R^2$ is the residue of (L)-valine. This compound is designated herein "Compound X", and its chemical name is ((Z-Octadec)-9-enoic acid 1-hydroxymethyl-2-methyl-propyl)-amide.

In another embodiment, X in Formula A is O, and the compound is represented by the structure:

A2)
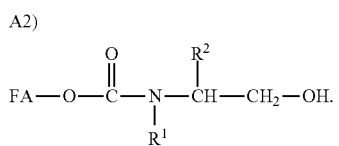

In another embodiment, X in Formula A is $NR^1$, and the compound is represented by the structure:

A3)
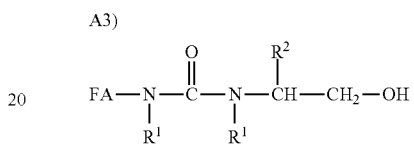

In another embodiment, the compound of the invention is represented by the formula—

B)
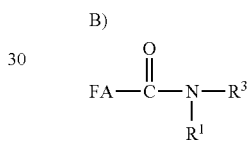

wherein $R^3$ is shown below.

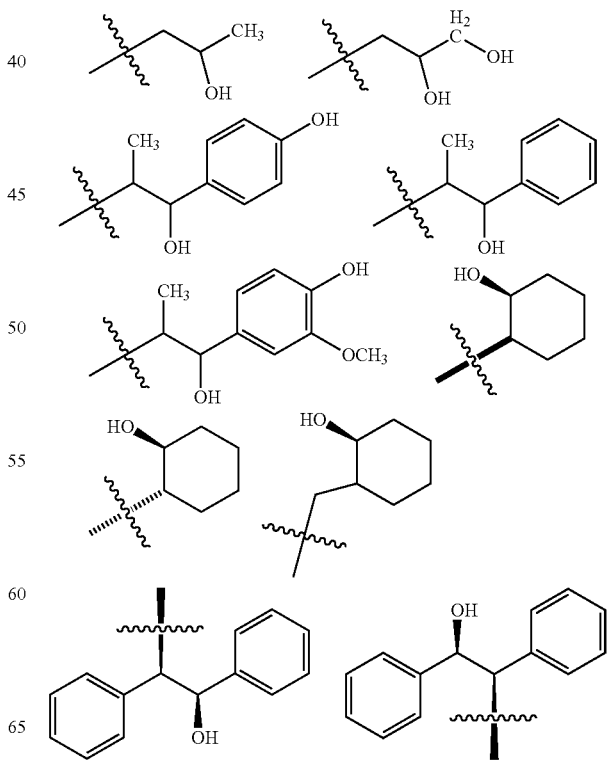

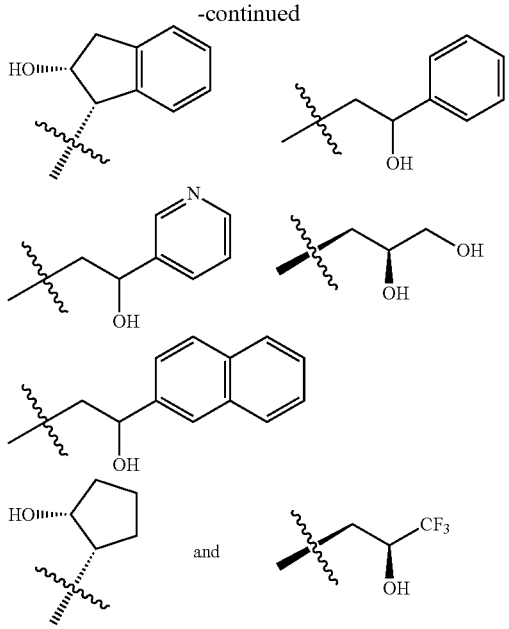

In accordance with this embodiment, the compound is derived from a residue of a fatty acid as described above, bonded by its carboxyl moiety to the amino group of a substituted amino alcohol.

In one embodiment, $R^1$ and $R^3$, together with the nitrogen to which they are respectively attached, can form a group represented by the structure:

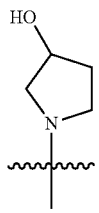

In one embodiment when FA is the residue of oleic acid or arachidonic acid, $R^3$ is not

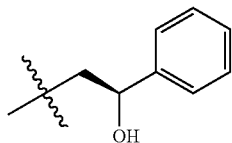 [SMILES: *C[C@H](O)c1ccccc1]

In another embodiment, when FA is the residue of arachidonic acid and $R^1$ is H, $R^3$ is not

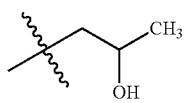 [SMILES: *CC(C)O]

In another embodiment, the compound of the invention is represented by the formula:

C)

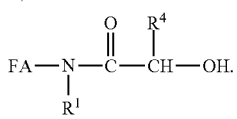

wherein $R^1$ and $R^4$ are as defined above. In accordance with this embodiment, the compound is derived from an amine derivative of a fatty acid as described above (e.g., oleyl amine), bonded by its amino moiety to the carboxyl group of an alpha-hydroxy acid. The term "amine derivative of a fatty acid" refers to a compound wherein the carboxyl group of the fatty acid has been converted to an amine (e.g., $NH_2$). For example, when the fatty acid is oleic acid, the corresponding amine derivative is oleylamine (i.e., $CH_3(CH_2)_7$—CH=CH—$(CH_2)_8$—$NH_2$). In one embodiment, $R^4$ is the residue of an (L)-amino acid. In another embodiment, $R^4$ is the residue of a (D)-amino acid. Non-limiting examples of such amino acids include glycine, alanine, homoserine, glutamic acid, valine, serine, arginine, ornithine, lysine, threonine, methionine, tryptophan, histidine, tyrosine, phenylalanine, aspartic acid, cysteine and isoleucine. In one embodiment when $R^1$ is H and FA is the residue of oleic acid, the amino acid is not glycine or alanine.

In another embodiment, the compound of the invention is represented by the structure:

D)

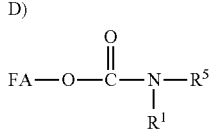

wherein $R^5$ is selected from:

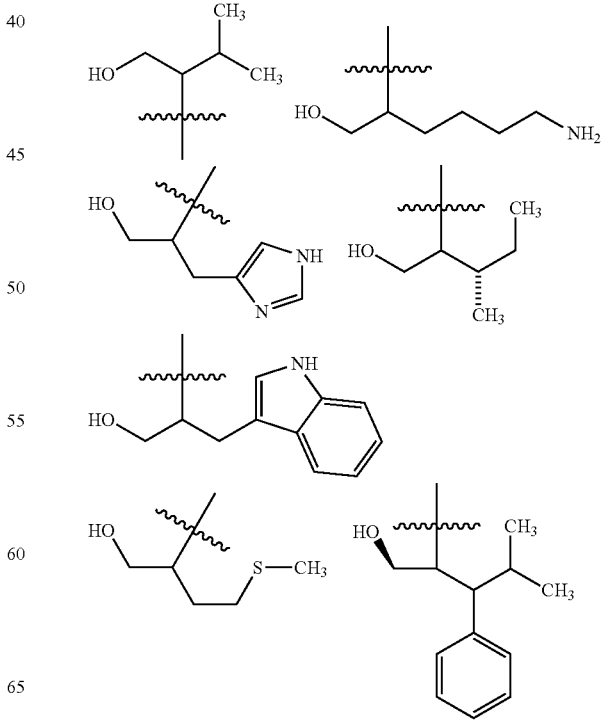

-continued

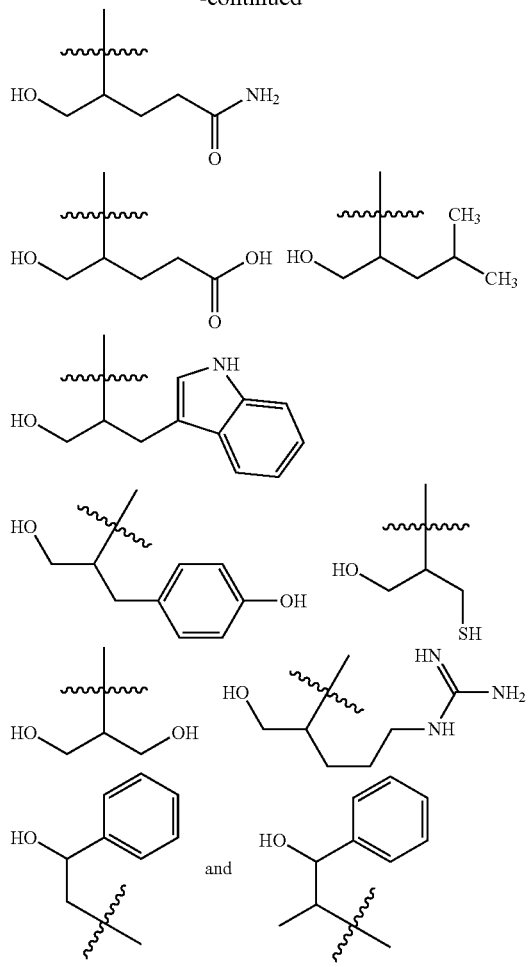

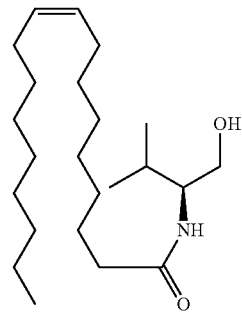
(10)

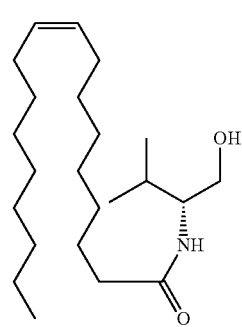
(11)

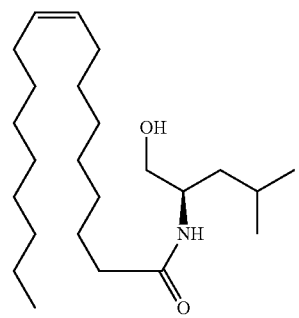
(13)

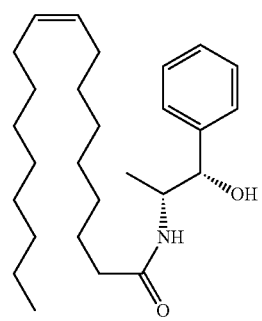
(14)

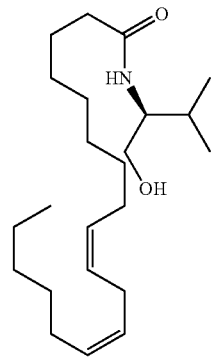
(17)

In accordance with this embodiment, the compound (a carbamate derivative) is derived from an alcohol-(C=O)— derivative of a fatty acid as described above, bonded by the carbonyl moiety to the amino group of a substituted ethanolamine. The term "alcohol derivative of a fatty acid" refers to a compound wherein the carboxyl group of the fatty acid has reduced to a hydroxyl group (e.g., OH). For example, when the fatty acid is oleic acid, the corresponding alcohol derivative is oleyl alcohol (i.e., $CH_3(CH_2)_7$—CH=CH—$(CH_2)_8$—$NH_2$).

In another embodiment, is the compound of the invention is represented by the structure:

E)

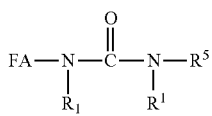

wherein $R^1$ and $R^5$ are as defined above. In accordance with this embodiment, the compound (a urea derivative) is derived from a fatty acid amine-(C=O)— derivative as described above, bonded by the carbonyl moiety to the amino group of a substituted ethanolamine.

In another embodiment, the present invention provides a compound selected from the group consisting of:

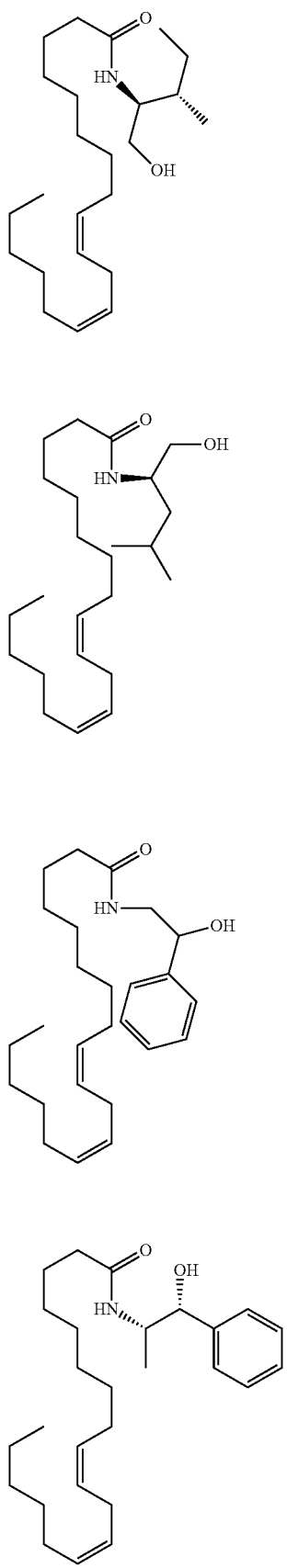
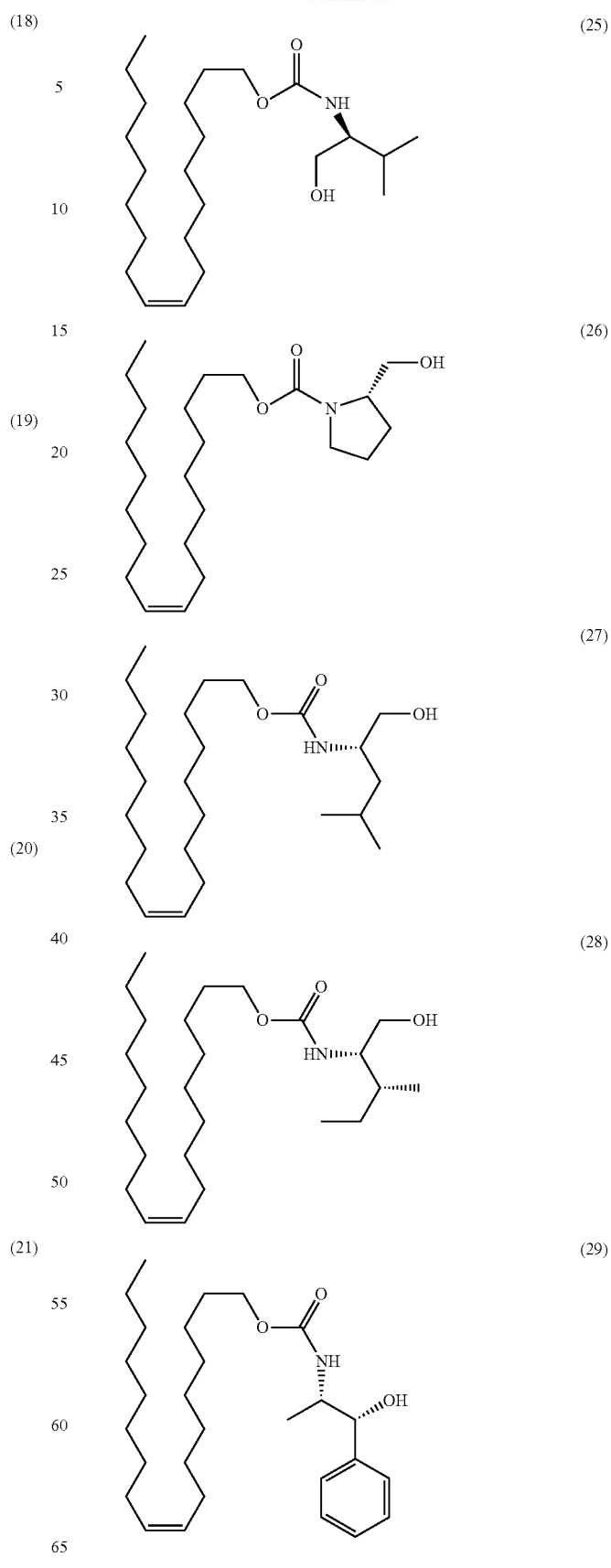

-continued

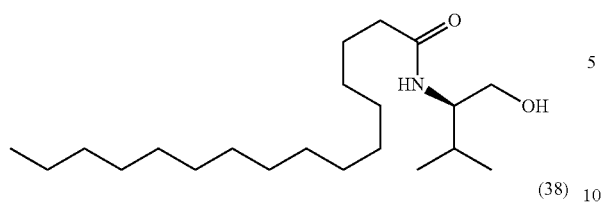
(37)

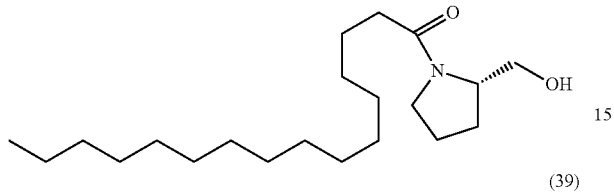
(38)

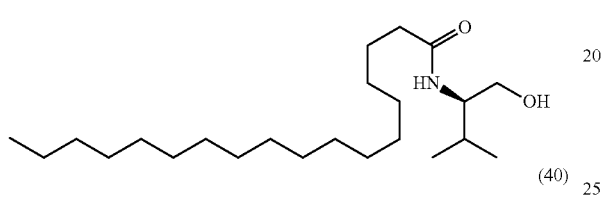
(39)

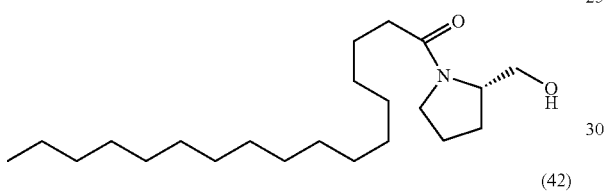
(40)

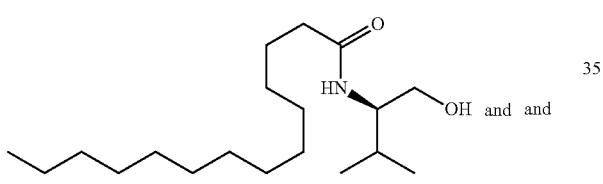
(42)

OH and and

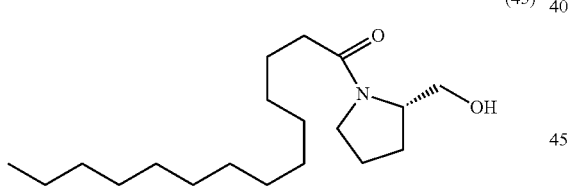
(45)

The present invention also contemplates pharmaceutical compositions that include a pharmaceutically acceptable carrier and, as an active ingredient, one or more of the compounds of the invention, represented by general formula I, as described above.

The pharmaceutical compositions of the present invention can be provided in any form known in the art, for example in a form suitable for oral administration (e.g., a solution, a suspension, a syrup, an emulsion, a dispersion, a suspension, a tablet, a pill, a capsule, a pellet, granules and a powder), for parenteral administration (e.g., intravenous, intramuscular, intraarterial, transdermal, subcutaneous or intraperitoneal), for topical administration (e.g., an ointment, a gel, a cream), for administration by inhalation or for administration via suppository.

In another embodiment the invention provides a method for treating or reducing the severity of obesity or a complication of obesity, increasing or facilitating weight loss, suppressing, inhibiting or reducing appetite, decreasing body mass index (BMI), decreasing food consumption, or improving cognitive function in a subject, comprising the step of administering to the subject a compound formula (I-A):

FA-A-B    (I-A)

wherein
A is:

1)
$$-X-\overset{O}{\underset{}{C}}-\underset{R^1}{N}-;$$

2)
$$-\overset{O}{\underset{}{C}}-;$$

3)
$$-\underset{R^1}{N}-\overset{O}{\underset{}{C}}-; \text{ or}$$

4)
$$-O-\overset{O}{\underset{}{C}}-;$$

B is

1)
$$-\underset{}{\overset{R^2}{CH}}-CH_2-OH;$$

2)
$$-\underset{R^1}{N}-R^3;$$

3)
$$-\underset{}{\overset{R^4}{CH}}-OH; \text{ or}$$

4)
$$-\underset{R^1}{N}-R^5;$$

FA is a residue of a fatty acid selected from the group consisting of oleic acid (oleoyl), elaidic acid (elaidoyl), linoleic acid (linoleoyl), gamma-linoleic acid (gamma-linoleoyl), alpha-linoleic acid (alpha-linoleoyl), eicosapentaenoic acid (eicosapentaenoyl), docosahexaenoic acid docosahexaenoyl), arachidonic acid arachidonyl), palmitic acid (palmitoyl), palmitoleic acid (palmitoleoyl), stearic acid (stearoyl), lauric acid (lauroyl), myristic acid (myristoyl), and tetradec-7-enoic acid (tetradec-7-enoyl), or the residue of an amine or alcohol derivative of any of the foregoing fatty acids;

X is O, $NR^1$ or a bond;

$R^1$ is independently at each occurrence H or $CH_3$;

$R^2$ is selected from the group consisting of:

1) the residue of an (L)- or (D)-amino acid when $R^1$ is H, or of an (L)- or (D)-N-methyl amino acid when $R^1$ is $CH_3$, provided that, for compounds wherein A is

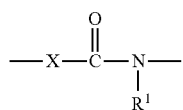

and B is

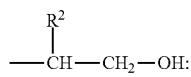

(i) when X is a bond, R¹ is H and FA is the residue of oleic acid, the amino acid is not glycine or alanine;

(ii) when X is a bond, R¹ is H and FA is the residue of elaidic acid, the amino acid is not glycine; and (iii) when X is a bond, R¹ is CH$_3$ and FA is the residue of oleic acid, the N-methyl amino acid is not sarcosine;

2) when R¹ is H, the residue of an unnatural amino acid selected from the group consisting of Dap, dimethyl Dap, dimethylamino lysine, Dab, 2-pyridyl alanine, 3-pyridyl alanine, 1-napththyl alanine, 2-naphthyl alanine, homoarginine, citrulline, phenylglycine, norleucine, ornithine, Abu, Apn, Ahx, 4-halo phenyl alanine, 4-amino phenyl alanine and 4-nitro phenylalanine; or when R¹ is CH$_3$, the N-methyl derivatives of the any of the foregoing amino acids;

or R¹ and R², together with the nitrogen and carbon to which they are respectively attached, can form a heterocycle selected from:

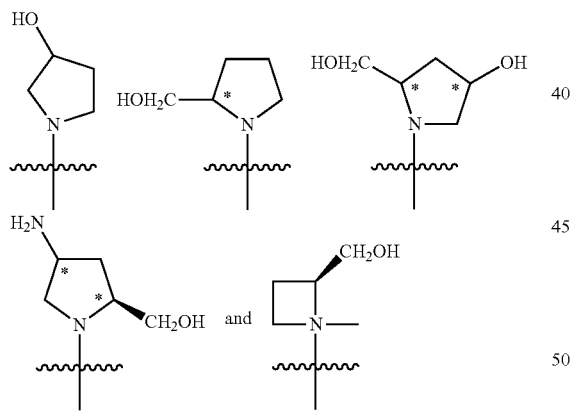

R³ is selected from the group consisting of:

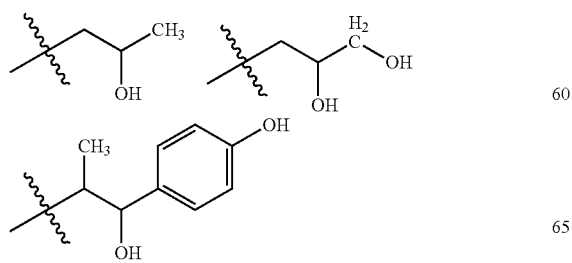

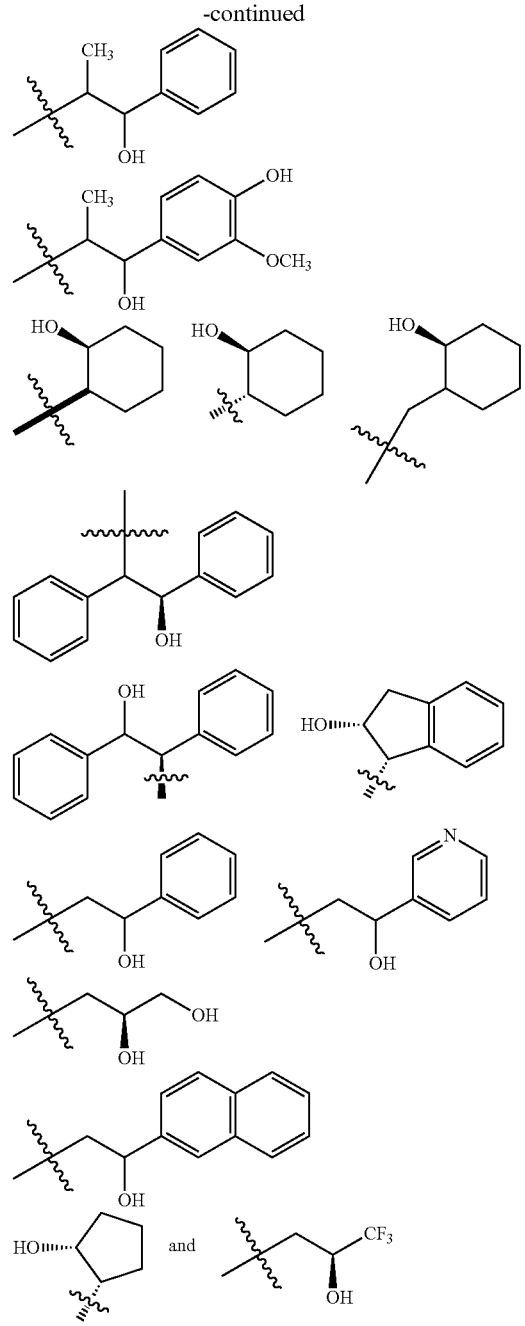

or R¹ and R³, together with the nitrogen to which they are respectively attached, can form a group represented by the structure:

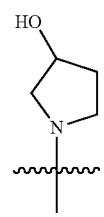

$R^4$ the residue of an (L)- or (D)-amino acid; and
$R^5$ is selected from the group consisting of:

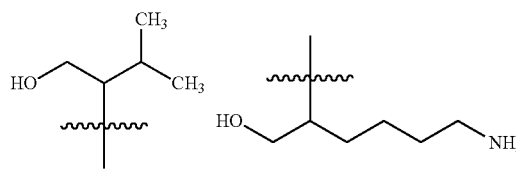

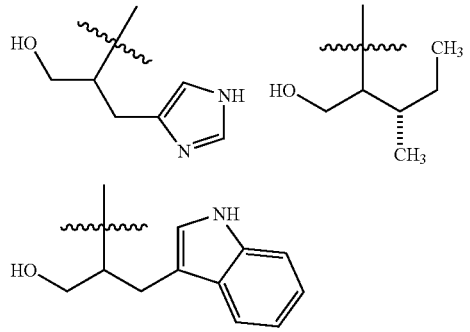

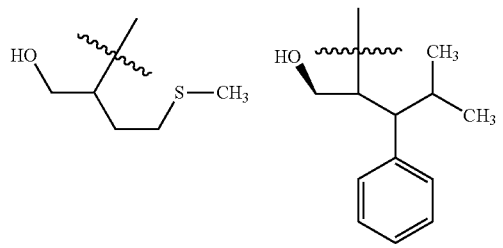

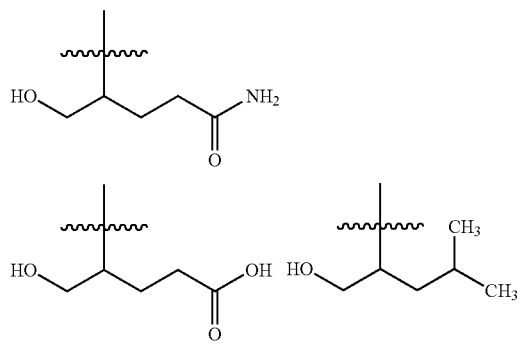

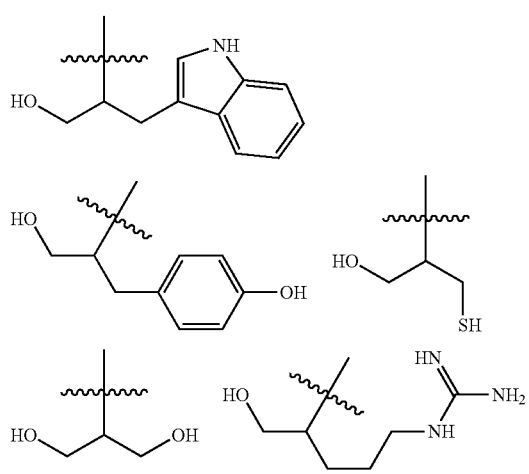

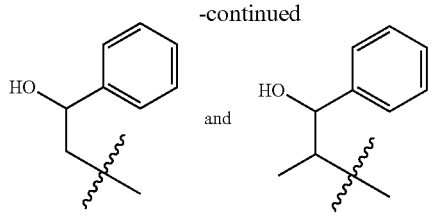

or $R^1$ and $R^5$, together with the nitrogen to which they are attached, can form a heterocycle selected from:

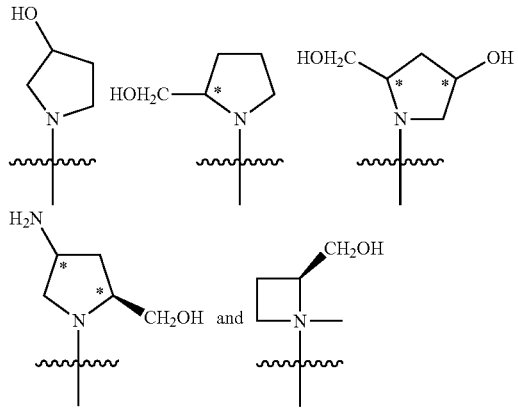

including salts, hydrates, solvates, polymorphs, optical isomers, geometrical isomers, enantiomers, diastereomers, and mixtures thereof.

The present invention further relates to a method for treating or reducing the severity of obesity in a subject, comprising the step of administering to the subject a compound of formula (I) or (I-A) according to the present invention, in an amount effective to treat or reduce the severity of obesity in the subject.

In another embodiment, the invention provides a method for treating or reducing the severity of a complication of obesity a subject, comprising the step of administering to the subject a compound of formula (I) or (I-A) according to the present invention, in an amount effective to treat or reduce the severity of the obesity complication in the subject.

In another embodiment, the invention provides a method for promoting, increasing or facilitating weight loss in a subject, comprising the step of administering to the subject a compound of formula (I) or (I-A) according to the present invention, in an amount effective to promote, increase or facilitate weight loss in the subject.

In another embodiment, the invention provides a method of suppressing, inhibiting or reducing appetite of a subject, comprising the step of administering to the subject a compound of formula (I) or (I-A) according to the present invention, in an amount effective to suppress, inhibit or reduce the appetite of the subject.

In another embodiment, the invention provides a method of decreasing body mass index (BMI) in a subject, comprising the step of administering to the subject a compound of formula (I) or (I-A) according to the present invention, in an amount effective to decrease BMI in the subject.

In another embodiment, the invention provides a method of decreasing food consumption in a subject, comprising the step of administering to the subject a compound of formula (I) or (I-A) according to the present invention, in an amount effective to decrease food consumption in the subject.

In another embodiment, the invention provides a method of improving cognitive function in a subject, comprising the step of administering to the subject a compound of formula (I) or (I-A) according to the present invention, in an amount effective to improve cognitive function in the subject.

In another embodiment, the present invention relates to the use of a compound of formula (I) or (I-A), for the manufacture of a medicament for treating or reducing the severity of obesity or a complication of obesity, increasing or facilitating weight loss, suppressing, inhibiting or reducing appetite, decreasing body mass index (BMI), decreasing food consumption, or improving cognitive function.

BRIEF DESCRIPTION OF THE DRAWINGS

FIG. 1: shows the effect of 1 mg/kg Compound X on body weight in mice.

DETAILED DESCRIPTION OF THE PRESENT INVENTION

Figure 1A:
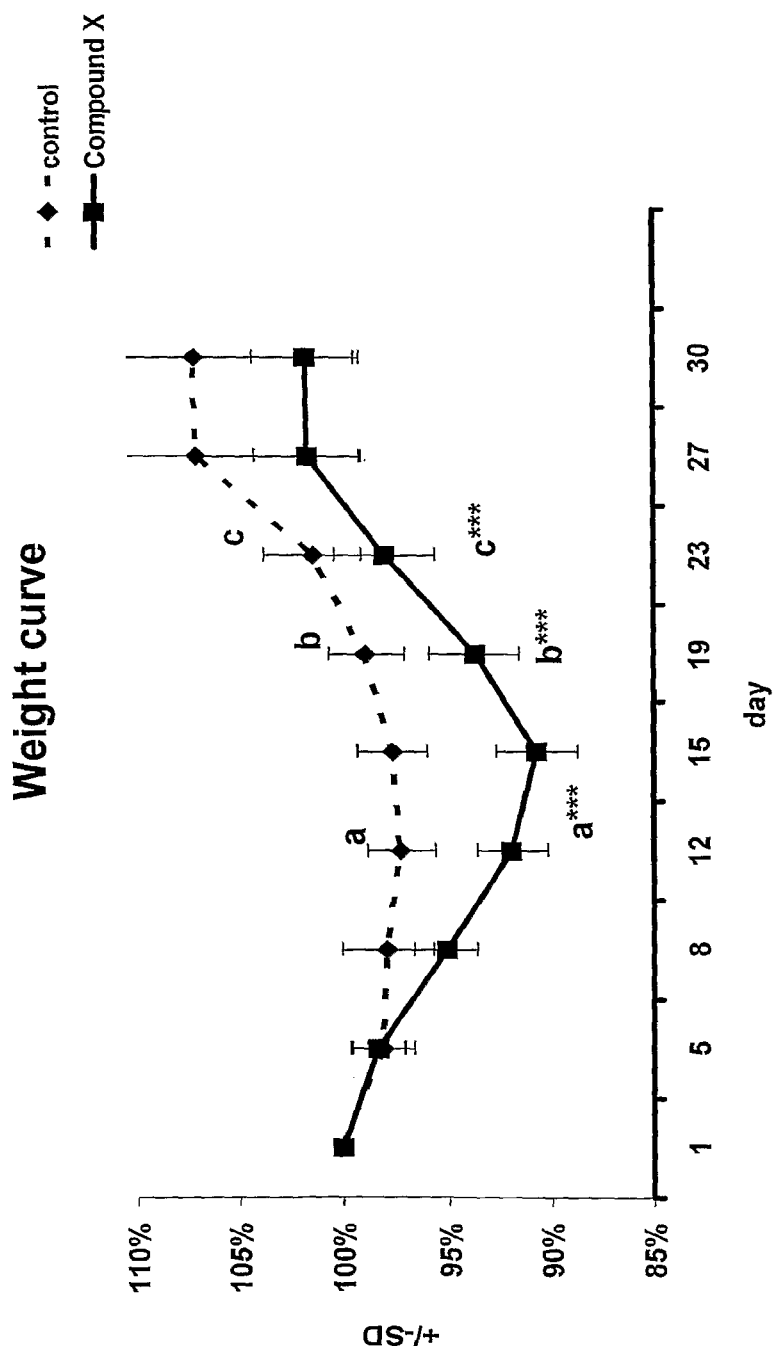
FIG. 1A: Intra Peritoneal administration.

The present invention relates to a novel family of fatty acid derivatives (e.g., oleyl ethanolamide derivatives and related structures), which regulate food consumption and body weight. The compounds of the invention are useful in methods of treating or reducing the severity of obesity or a complication of obesity, increasing or facilitating weight loss, inhibiting or reducing appetite, and decreasing food consumption and body mass index (BMI). The compounds of the invention also improve cognitive function and are thus useful in the treatment of diseases and conditions associated with decreased cognitive function.

Compounds

The compounds of the invention are derived from fatty acids (e.g., oleic acid or oleoyl) or their amino or alcohol derivatives (e.g., oleyl amine or oleyl alcohol respectively), and hydroxy amino acids derived from natural or unnatural amino acids. The compounds are represented by any one or more of the following structures:

The compounds are represented by general formula (I):

FA-A-B  (I)

wherein
A is:

1)

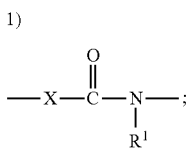

2)

3)

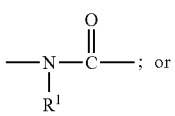; or

4)

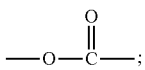;

B is

1)

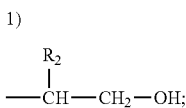

2)

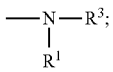;

3)

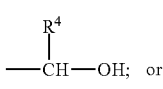; or

4)

FA is a residue of a fatty acid selected from the group consisting of oleic acid (oleoyl), elaidic acid (elaidoyl), linoleic acid (linoleoyl), gamma-linoleic acid (gamma-linoleoyl), alpha-linoleic acid (alpha-linoleoyl), eicosapentaenoic acid (eicosapentaenoyl), docosahexaenoic acid (docosahexaenoyl), arachidonic acid (arachidonyl), palmitic acid (palmitoyl), palmitoleic acid (palmitoleoyl), stearic acid (stearoyl), myristic acid (myristoyl), lauric acid (lauroyl), and tetradec-7-enoic acid (tetradec-7-enoyl), or the residue of an amine or alcohol derivative of any of the foregoing fatty acids;

X is O, NR¹ or a bond;
R¹ is independently at each occurrence H or CH₃;
R² is selected from the group consisting of:
1) the residue of an (L)- or (D)-amino acid when R¹ is H, or of an (L)- or (D)-N-methyl amino acid when R¹ is CH₃, provided that, for compounds wherein A is

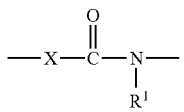

and B is

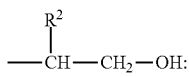

(i) when X is a bond, R¹ is H and FA is the residue of oleic acid, the amino acid is not glycine, alanine, serine, tyrosine, phenylalanine or cysteine;
(ii) when X is a bond, R¹ is H and FA is the residue of arachidonic acid, the amino acid is not glycine, alanine, tyrosine or phenylalanine;
(iii) when X is a bond, R¹ is H and FA is the residue of palmitic acid, myristic acid or stearic acid, the amino acid is not glycine;
(iv) when X is a bond, R¹ is H and FA is the residue of linoleic acid, the amino acid is not glycine or alanine;
(v) when X is a bond, R¹ is H and FA is the residue of elaidic acid, the amino acid is not glycine or serine; and
(vi) when X is a bond, R¹ is CH₃ and FA is the residue of oleic acid, the N-methyl amino acid is not sarcosine;
2) when R¹ is H, the residue of an unnatural amino acid selected from the group consisting of Dap, dimethyl Dap, dimethylamino lysine, Dab, 2-pyridyl alanine, 3-pyridyl alanine, 1-napththyl alanine, 2-naphthyl alanine, homoarginine, citrulline, phenylglycine, norleucine, ornithine, Abu, Apn, Ahx, 4-halo phenyl alanine, 4-amino phenyl alanine and 4-nitro phenylalanine; or when R¹ is CH₃, the N-methyl derivatives of the any of the foregoing amino acids, provided that, for compounds wherein A is

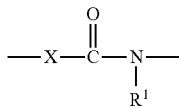

and B is

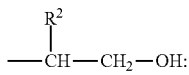

(i) when X is a bond, and FA is the residue of oleic acid or arachidonic acid, the amino acid is not phenylglycine; and
(ii) when X is a bond and FA is the residue of elaidic acid, the amino acid is not Ahx;

or R¹ and R², together with the nitrogen and carbon to which they are respectively attached, can form a heterocycle selected from

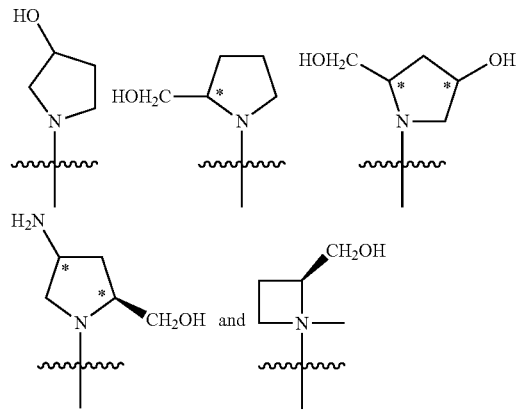

provided that when FA is the residue of oleic acid or arachidonic acid and X is a bond, R¹ and R² together with the nitrogen and carbon to which they are respectively attached are not

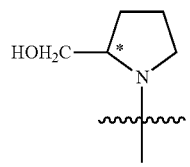 [SMILES: *N1CCCC1CO]

R³ is selected from the group consisting of:

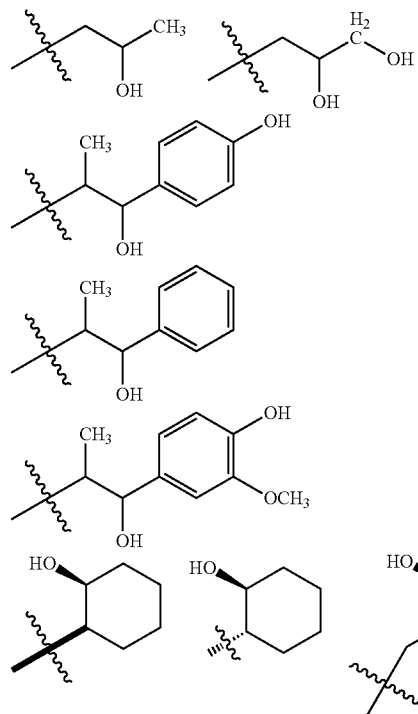

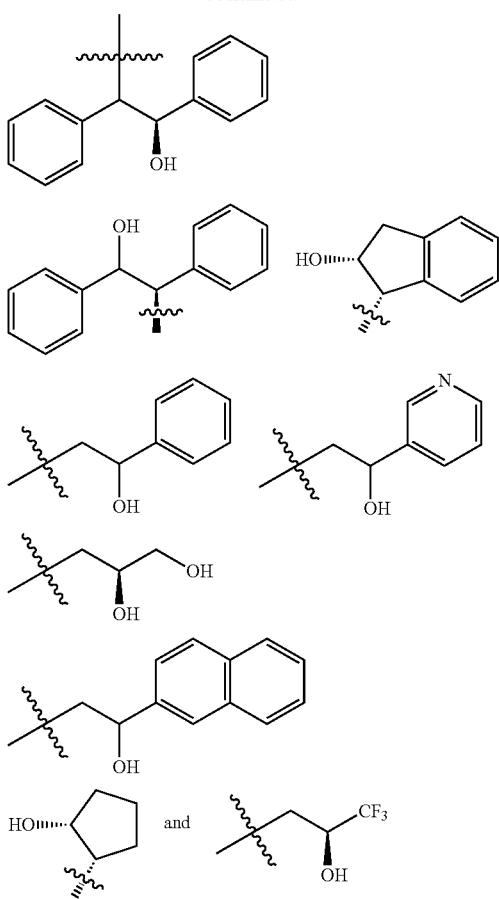

or R$^1$ and R$^3$, together with the nitrogen to which they are attached, can form a group represented by the structure:

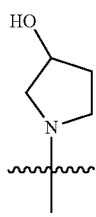

provided that, for compounds wherein A is

and B is

(i) when FA is the residue of oleic acid or arachidonic acid and R$^1$ is H, R$^3$ is not

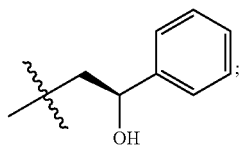 [SMILES: *C[C@H](O)c1ccccc1]

and (ii) when FA is the residue of arachidonic acid and R$^1$ is H, R$^3$ is not

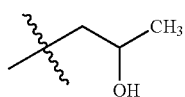 [SMILES: *CC(C)O]

R$^4$ the residue of an (L)- or (D)-amino acid, provided that, for compounds wherein A is

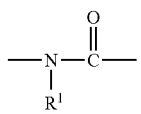

and B is

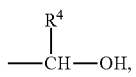

R$^1$ is H and FA is the residue of oleic acid, the amino acid is not glycine or alanine; and R$^5$ is selected from the group consisting of:

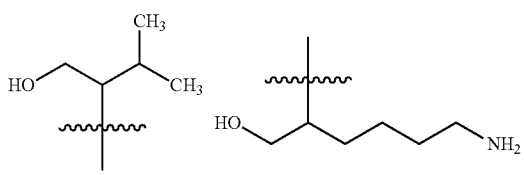

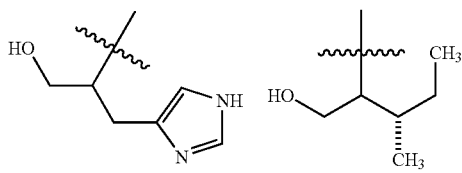

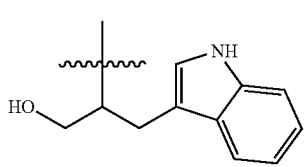

-continued

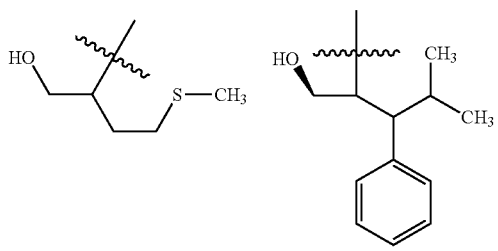

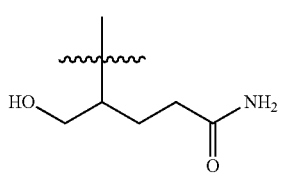

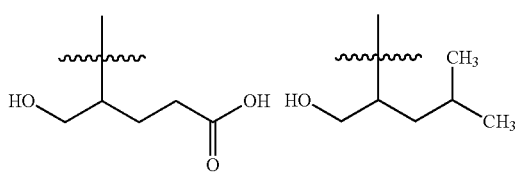

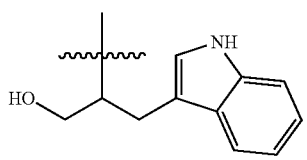

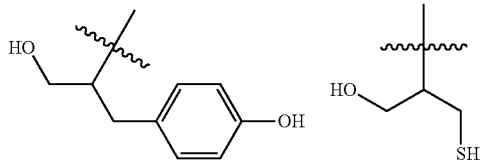

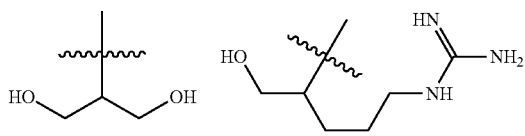

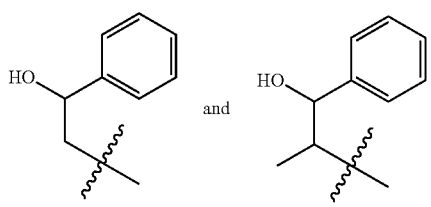

and or R¹ and R⁵, together with the nitrogen to which they are attached, can form a heterocycle selected from:

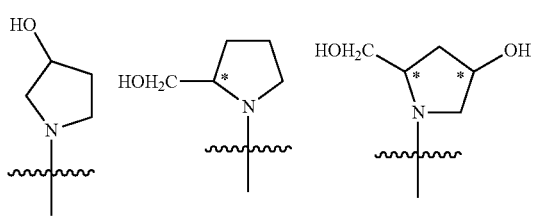

-continued

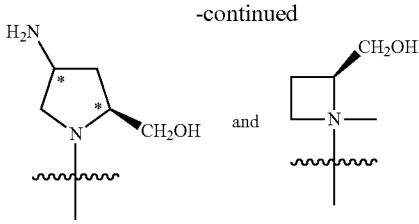 and including salts, hydrates, solvates, polymorphs, optical isomers, geometrical isomers, enantiomers, diastereomers, and mixtures thereof.

In several embodiments, the compounds of general formula (I) are represented by any one or more of the following structures:

A)

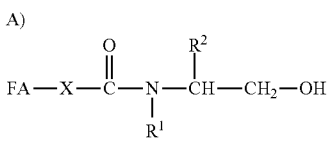

B)

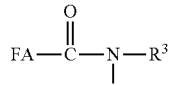

C)

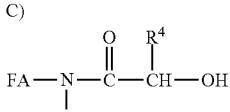

D)

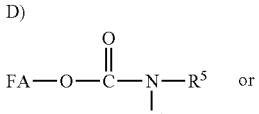 or

E)

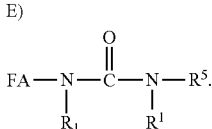

including salts, hydrates, solvates, polymorphs, optical isomers, geometrical isomers, enantiomers, diastereomers, and mixtures thereof.

Amino Acids

The terms "natural and unnatural amino acids" (α-amino acid) refers to both the naturally occurring amino acids and other unnaturally amino acids including both optically active (D and L) forms as well as racemic derivatives. As contemplated herein, the amino acids are conjugated to the fatty acid derivatives by forming an amide bond between the carboxyl group of the fatty acid and the amino group of the amino acid. The naturally occurring amino acids are, e.g., glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of unnatural α-amino acids include α-aminoisobutyric acid, α-aminobutyric acid, γ-aminobutyric acid, citrulline, N-methyl derivatives of any of the natural amino acids listed above (e.g., N-methyl-alanine, N-methyl-glycine (sarcosine), N-methyl-glutamic acid, N-methyl serine, N-methyl leucine, N-methyl isoleucine, N-methyl phenylalanine and N-methyl aspartate), homocitrulline, homoproline, homoserine, hydroxyproline, norleucine, 4-aminophenylalanine, 4-halo phenyl alanine (e.g., 4-fluoro, bromo, chloro or iodo phenylalanine wherein), 4-nitro phenylalanine, statine, hydroxylysine, kynurenine, 3-(2'-naphthypalanine, 3-(1'-naphthyl)alanine, methionine sulfone, (t-butyl)alanine, (t-butyl)glycine, 4-hydroxyphenylglycine, aminoalanine, phenylglycine, vinylalanine, propargyl-glycine, 1,2,4-triazolo-3-alanine, thyronine, 6-hydroxytryptophan, 5-hydroxytryptophan, 3-hydroxykynurenine, 3-aminotyrosine, trifluoromethyl-alanine, 2-thienylalanine, (2-(4-pyridyl)ethyl) cysteine, 3,4-dimethoxyphenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, elastatinal, norleucine, norvaline, alloisoleucine, homoarginine, thioproline, dehydroproline, hydroxyproline, homoproline, α-amino-n-butyric acid, cyclohexylalanine, 2-amino-3-phenylbutyric acid, β-2- and 3-thienylalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-(sulfo)tyrosine, 3-(carboxy)tyrosine, 3-(phospho)tyrosine, the 4-methane sulfonic acid ester of tyrosine, 4-methane phosphonic acid ester of tyrosine, 3,5-diiodotyrosine, 3-nitrotyrosine, s-alkyl lysine, and δ-alkyl ornithine, Dap (i.e., the residue is $CH_2NH_2$), dimethyl Dap (i.e., the residue is $CH_2N(CH_3)_2$), dimethylamino lysine (i.e., the residue is $(CH_2)_4$—$N(CH_3)_2$), Dab (i.e., the residue is $CH_2CH_2NH_2$), Abu (i.e., the residue is $CH_2CH_3$), Apn (i.e., the residue is $CH_2CH_2CH_3$), and Ahx (i.e., the residue is $(CH_2)_3$—$CH_3$).

The term "residue of an amino acid" refers to the substituent on the alpha carbon of an amino acid (whether natural or unnatural) or a derivative of such an amino acid. A "derivative of an amino acid" is a molecule which is derived from an amino acid by reaction such as reduction or substitution. For example, for the purpose of illustration and not for limitation, an alpha hydroxy acid is an amino acid derivative in which the amino group has been substituted by a hydroxyl group. A substituted amino alcohol is an amino acid derivative in which the carboxyl group has been reduced to an alcohol (Scheme 1)

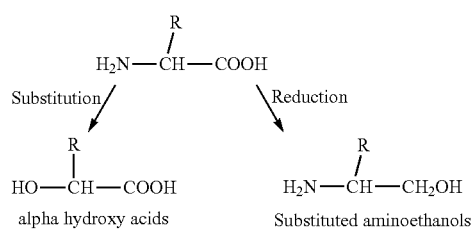

Scheme 1

Fatty Acids

The fatty acid can be any fatty acid known in the art, whether or not naturally occurring, and can be derived from a natural product, semi-synthetic or synthetic. The fatty acid preferably includes greater than 12 carbon atoms, for example between 12 to 24 carbon atoms. The alkyl chain of the fatty acid can be a straight chain, a branched chain, or cyclic chain, all of which can be, saturated, mono- or polyunsaturated, (conjugated or non-conjugated), and combinations thereof.

In one embodiment, FA is the residue of oleic acid (9Z)-octadecenoic acid), referred to herein as "oleoyl". In one embodiment, FA is the residue of elaidic acid (9E)-octadecenoic acid), referred to herein as "elaidoyl". In another embodiment, FA is the residue of linoleic acid (9Z,12Z-octadecadienoic acid or (9E,12E-octadecadienoic acid), referred to herein as "linoleoyl". In another embodiment, FA is a residue of gamma-linoleic acid (all-Z-6,9,12-octadecatrienoic acid or all-E-6,9,12-octadecatrienoic acid), referred to herein as "gamma-linoleoyl". In another embodiment, FA is a residue of alpha-linoleic acid (all-cis-9,12,15-octadecatrienoic acid), referred to herein as "alpha-linoleoyl". In another embodiment, FA is a residue of eicosapentaenoic acid ((5Z,8Z,11Z,14Z,17Z)-icosa-5,8,11,14,17-pentaenoic acid) or ((5E,8E,11E,14E,17E)-icosa-5,8,11,14,17-pentaenoic acid), referred to herein as "eicosapentaenoyl". In another embodiment, FA is a residue of docosahexaenoic acid ((4Z,7Z,10Z,13Z,16Z,19Z)-docosa-4,7,10,13,16,19-hexaenoic acid) or ((4E,7E,10E,13E,16E,19E)-docosa-4,7,10,13,16,19-hexaenoic acid), referred to herein as "docosahexaenoyl". In another embodiment, FA is a residue of stearic acid (octadecanoic acid), referred to herein as "stearoyl". In another embodiment, the FA is a residue of palmitic acid (hexadecanoic acid), referred to herein as "palmitoyl". In another embodiment, FA is the residue of arachidonic acid (all-Z-5,8,11,14-eicosatetraenoic acid) or all E-5,8,11,14-eicosatetraenoic acid, referred to herein as "arachidonoyl". In another embodiment, FA is the residue of myristic acid (tetradecanoic acid), referred to herein as "myristoyl". In another embodiment, FA is the residue of Z- or E-tetradec-7-enoic acid.

In other embodiments, the fatty acid includes omega-3 long chain polyunsaturated fatty acids. Additional examples of fatty acids for use in the present invention include, but are not restricted to: lauric acid (n-dodecanoic acid), arachidic acid (n-eicosanoic acid), behenic acid (n-docosanoic acid), lignoceric acid (n-tetracosanoic acid), linolenic acid (All-Z-9,12,15,-octadecatrienoic acid; Z,E,Z-9,11,13-octadecatrienoic acid; Z,E,E-9,11,13-octadecatrienoic acid, and E,E,Z-9,11,13-octadecatrienoic acid).

In one embodiment, FA is an amine derivative of any of the foregoing acids. Such amine derivatives include, but are not limited to oleyl amine, linoleyl amine, gamma-lineoleyl amine, alpha linoleyl amine, eicosapentaenoyl amine, docosahexaenoyl amine, stearyl amine, palmityl amine, arachidonyl amine, myristyl amine, and Z- or E-tetradec-7-enoyl amine.

In another embodiment, FA is an alcohol derivative of any of the foregoing acids. Such alcohol derivatives include, but are not limited to oleyl alcohol, linoleyl alcohol, gamma-lineoleyl alcohol, alpha linoleyl alcohol, eicosapentaenoyl alcohol, docosahexaenoyl alcohol, stearyl alcohol, palmityl alcohol, arachidonyl alcohol, myristyl alcohol, and Z- or E-tetradec-7-enoyl alcohol.

In one particular embodiment, the present invention provides a compound of the formula:

A)

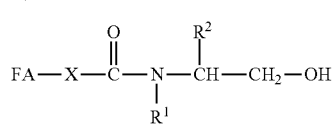

wherein X, $R^1$ and $R^2$ are defined above. In one embodiment, X in Formula A is a bond, and the compound is represented by the structure:

A1)

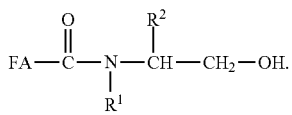

In accordance with this embodiment, the compound is derived from a residue of a fatty acid as described above, bonded by its carboxyl moiety to the amino group of a substituted amino alcohol. In one aspect of the aforementioned embodiment, $R^1$ in H. In accordance with this embodiment, $R^2$ can be the residue of a naturally occurring (L)-amino acid or the residue of a (D)-amino acid. Non-Limiting examples of such amino acids include glycine ($R^2$=H), alanine ($R^2$=CH$_3$), cysteine ($R^2$=CH$_2$SH), tyrosine ($R^2$=CH$_2$-4-hydroxyphenyl), phenylalanine ($R^2$=CH$_2$-phenyl), serine ($R^2$=CH$_2$OH), homoserine ($R^2$=CH$_2$CH$_2$OH), glutamic acid ($R^2$=CH$_2$CH$_2$COOH), valine ($R^2$=CH(CH$_3$)$_2$), arginine ($R^2$=CH$_2$CH$_2$CH$_2$NHC(=NH)NH$_2$), ornithine ($R^2$=CH$_2$CH$_2$CH$_2$NH$_2$), lysine ($R^2$=CH$_2$CH$_2$CH$_2$CH$_2$NH$_2$), threonine ($R^2$=CH(CH$_3$)(OH)), methionine ($R^2$=CH$_2$CH$_2$SCH$_3$), tryptophan ($R^2$=CH$_2$-1H-indol-3-yl)), histidine ($R^2$=CH$_2$-imidazolyl), aspartic acid ($R^2$=CH$_2$COOH) and isoleucine ($R^2$=CH(CH$_3$)CH$_2$CH$_2$CH$_3$). In a currently preferred embodiment, $R^2$ is the residue of (L)-valine. In one particular embodiment when $R^1$ in H and FA is the residue of oleic acid, the amino acid is not glycine, alanine, serine, tyrosine, phenylalanine or cysteine. In another particular embodiment when $R^1$ in H and FA is the residue of arachidonic acid, the amino acid is not glycine, alanine, tyrosine or phenylalanine. In another embodiment when $R^1$ in H and FA is the residue of palmitic acid, myristic acid or stearic acid, the amino acid is not glycine. In another embodiment when $R^1$ in H and FA is the residue of linoleic acid, the amino acid is not glycine or alanine. In another embodiment when $R^1$ is H and FA is the residue of elaidic acid, the amino acid is not glycine or serine.

In another embodiment, $R^1$ is CH$_3$. In accordance with this embodiment, $R^2$ can be the residue of an N-methyl(L)-amino acid or the residue of an N-methyl(D)-amino acid. Non-limiting examples of such N-methyl amino acids include N-methyl serine ($R^2$=CH$_2$OH), N-methyl alanine ($R^2$=CH$_3$), N-methyl leucine ($R^2$=CH$_2$CH(CH$_3$)$_2$); N-methyl isoleucine ($R^2$=CH(CH$_3$)CH$_2$CH$_3$), sarcosine ($R^2$=H), N-methyl phenylalanine ($R^2$=CH$_2$-phenyl), and N-methyl aspartic acid ($R^2$=CH$_2$COOH). In one embodiment when $R^1$ is CH$_3$ and FA is the residue of oleic acid, the N-methyl amino acid is not sarcosine ($R^2$=H).

In another embodiment, when $R^1$ is H, $R^2$ is the residue of an unnatural amino acid. Non-limiting examples of such amino acids or residues thereof include Dap ($R^2$=CH$_2$NH$_2$), dimethyl Dap ($R^2$=CH$_2$N(CH$_3$)$_2$), dimethylamino lysine ($R^2$=(CH$_2$)$_4$—N(CH$_3$)$_2$), Dab ($R^2$=CH$_2$CH$_2$NH$_2$), 2-pyridyl alanine ($R^2$=CH$_2$-2-pyr), 3-pyridyl alanine ($R^2$=CH$_2$-3-pyr), 1-naphthyl alanine ($R^2$=CH$_2$-1-napthyl), 2-naphthyl alanine ($R^2$=CH$_2$-2-naphthyl), homoarginine ($R^2$=(CH$_2$)$_4$—NH—C(N=H)NH$_2$), citrulline ($R^2$=(CH$_2$)$_4$—NH—C(=O)NH$_2$), phenylglycine ($R^2$=phenyl), norleucine ($R^2$=(CH$_2$)$_3$—CH$_3$), ornithine ($R^2$=(CH$_2$)$_3$—NH$_2$), Abu ($R^2$=CH$_2$CH$_3$), Apn ($R^2$=CH$_2$CH$_2$CH$_3$), Ahx ($R^2$=(CH$_2$)$_3$—CH$_3$), 4-halo phenyl alanine (e.g., 4-fluoro, bromo, chloro or iodo phenylalanine wherein $R^2$=CH$_2$-4-halophenyl), 4-amino phenylalanine ($R^2$=CH$_2$-4-NH$_2$-phenyl) and 4-nitro phenylalanine ($R^2$=CH$_2$-4-NO$_2$-phenyl). In one embodiment wherein $R^1$ is H and FA is the residue of oleic acid or arachidonic acid, the amino acid is not phenylglycine. In another embodiment wherein $R^1$ is H and FA is the residue of elaidic acid, the amino acid is not Ahx. In another embodiment, when $R^1$ is CH$_3$, $R^2$ can be the residue of N-methyl amino acid having any of the aforementioned residues.

In another embodiment, $R^1$ and $R^2$, together with the nitrogen and carbon to which they are respectively attached, can form a proline residue or a derivative thereof, represented by any one or more of the structures:

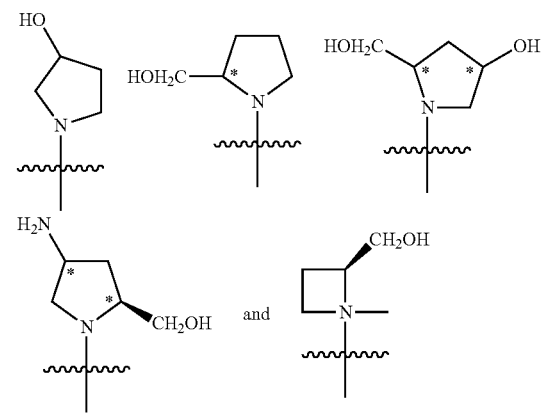

In one embodiment wherein $R^1$ is H and FA is the residue of oleic acid or arachidonic acid, $R^1$ and $R^2$ together with the nitrogen and carbon to which they are respectively attached are not

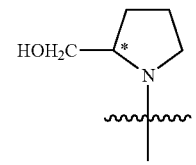 [SMILES: *N1CCCC1CO]

In one particularly preferred embodiment $R^1$ is H, and $R^2$ is the residue of (L)-valine. This compound is designated herein "Compound X", and its chemical name is ((Z-Octadec)-9-enoic acid 1-hydroxymethyl-2-methyl-propyl)-amide (also designated Oleyl-L-Valinol amide).

Compound-X

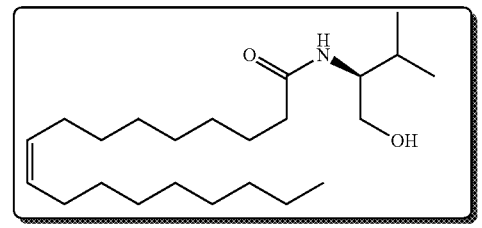

Oleoyl-L-Valinol amide[((Z-Octadec)-9-enoic acid 1-hydroxymethyl-2-methyl-propyl)-amide]

In another embodiment, X in Formula A is O, and the compound is represented by the structure:

A2)

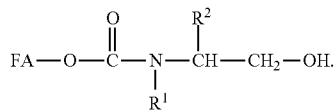

In another embodiment, X in Formula A is NR$^1$, and the compound is represented by the structure:

A3)

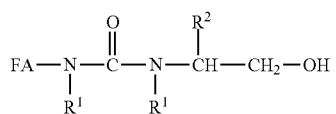

In another embodiment, the compound of the invention is represented by the formula—

B)

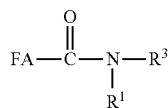

wherein R$^3$ is shown below.

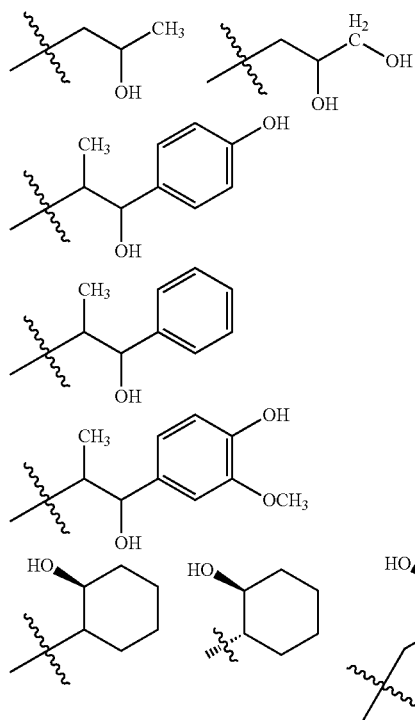

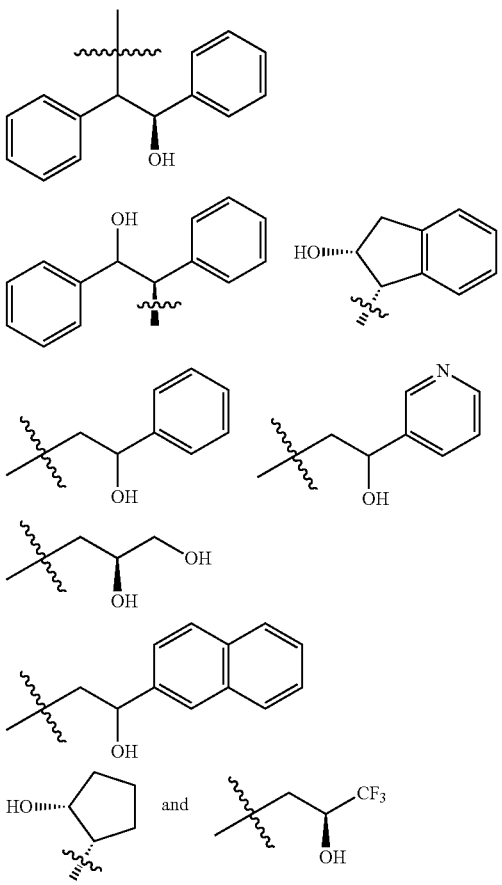

In accordance with this embodiment, the compound is derived from a residue of a fatty acid as described above, bonded by its carboxyl moiety to the amino group of a substituted amino alcohol.

In one embodiment, R$^1$ and R$^3$, together with the nitrogen to which they are respectively attached, can form a group represented by the structure:

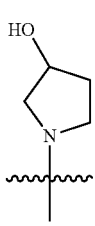

In one embodiment when FA is the residue of oleic acid or arachidonic acid, R$^3$ is not

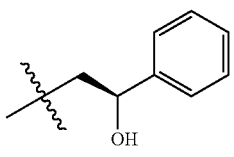 [SMILES: *C[C@H](O)c1ccccc1]

In another embodiment, when FA is the residue of arachidonic acid and $R^1$ is H, $R^3$ is not

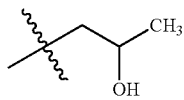

In another embodiment, the compound of the invention is represented by the formula:

C)

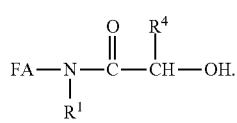

wherein $R^1$ and $R^4$ are as defined above. In accordance with this embodiment, the compound is derived from an amine derivative of a fatty acid as described above (e.g., oleyl amine), bonded by its amino moiety to the carboxyl group of an alpha-hydroxy acid. The term "amine derivative of a fatty acid" refers to a compound wherein the carboxyl group of the fatty acid has been converted to an amine (e.g., $NH_2$). For example, when the fatty acid is oleic acid, the corresponding amine derivative is oleylamine (i.e., $CH_3(CH_2)_7$—CH=CH—$(CH_2)_8$—$NH_2$). In one embodiment, $R^4$ is the residue of an (L)-amino acid. In another embodiment, $R^4$ is the residue of a (D)-amino acid. Non-limiting examples of such amino acids include glycine, alanine, homoserine, glutamic acid, valine, serine, arginine, ornithine, lysine, threonine, methionine, tryptophan, histidine, tyrosine, phenylalanine, aspartic acid, cysteine and isoleucine. In one embodiment when $R^1$ is H and FA is the residue of oleic acid, the amino acid is not glycine or alanine.

In another embodiment, the compound of the invention is represented by the structure:

D)

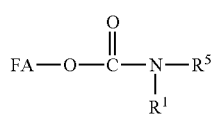

wherein $R^5$ is selected from:

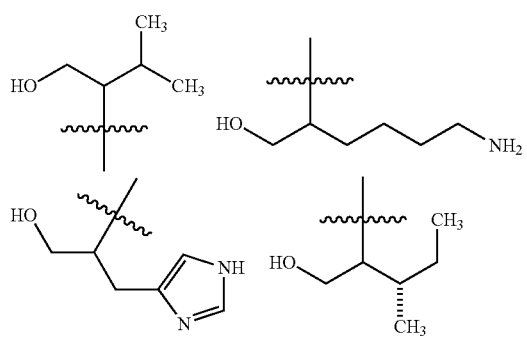

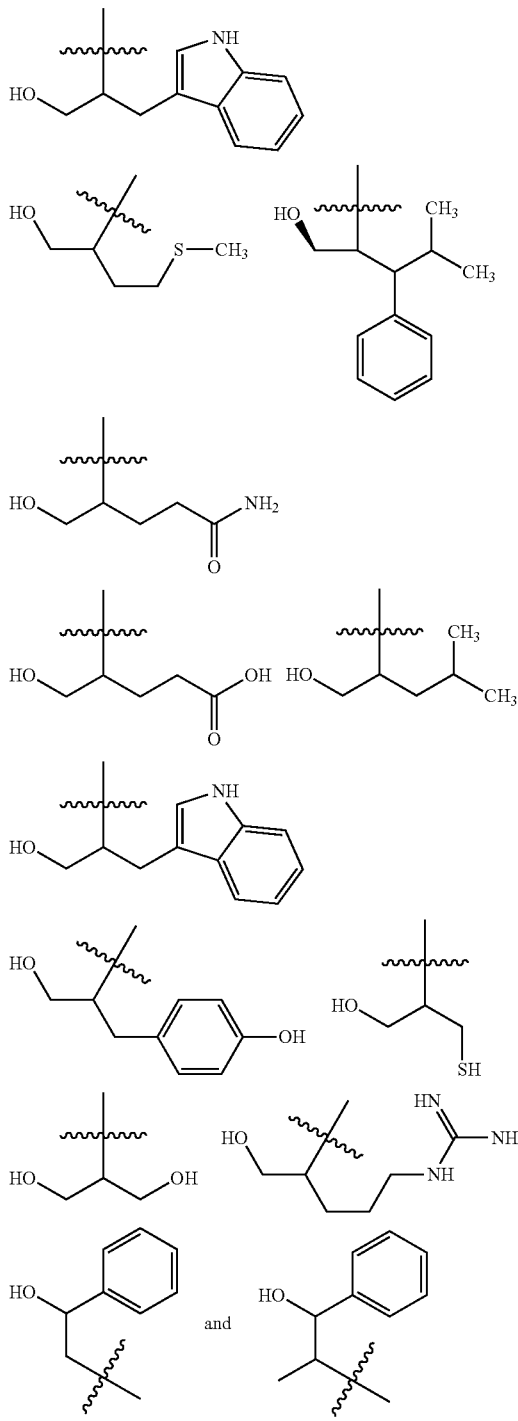

In accordance with this embodiment, the compound (a carbamate derivative) is derived from an alcohol-(C=O)— derivative of a fatty acid as described above, bonded by the carbonyl moiety to the amino group of a substituted ethanolamine. The term "alcohol derivative of a fatty acid" refers to a compound wherein the carboxyl group of the fatty acid has reduced to a hydroxyl group (e.g., OH). For example, when the fatty acid is oleic acid, the corresponding alcohol derivative is oleyl alcohol (i.e., $CH_3(CH_2)_7$—CH=CH—$(CH_2)_8$—$NH_2$).

In another embodiment, is the compound of the invention is represented by the structure:

E)

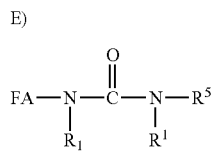

wherein $R^1$ and $R^5$ are as defined above. In accordance with this embodiment, the compound (a urea derivative) is derived from a fatty acid amine-(C=O)— derivative as described above, bonded by the carbonyl moiety to the amino group of a substituted ethanolamine.

In another embodiment, the present invention provides a compound selected from the group consisting of:

(10)

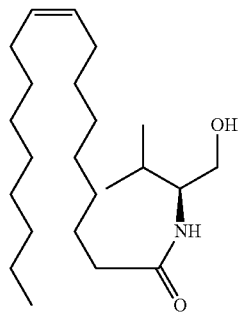

(11)

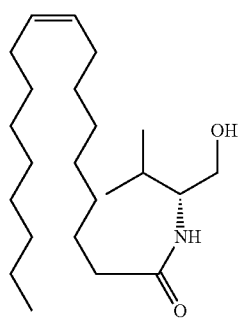

(13)

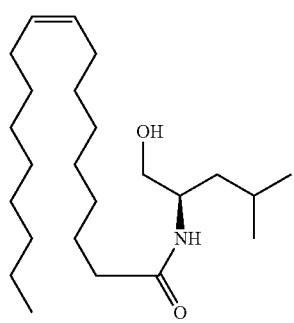

(14)

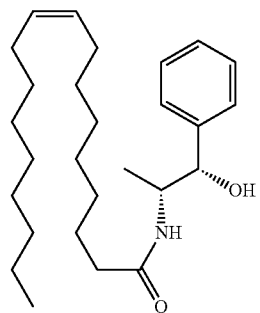

(17)

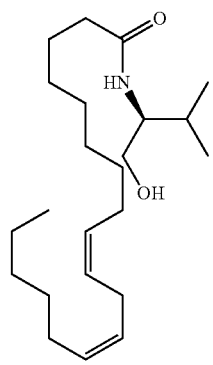

(18)

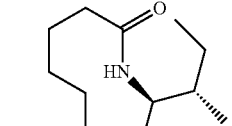

(19)

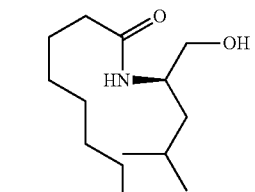

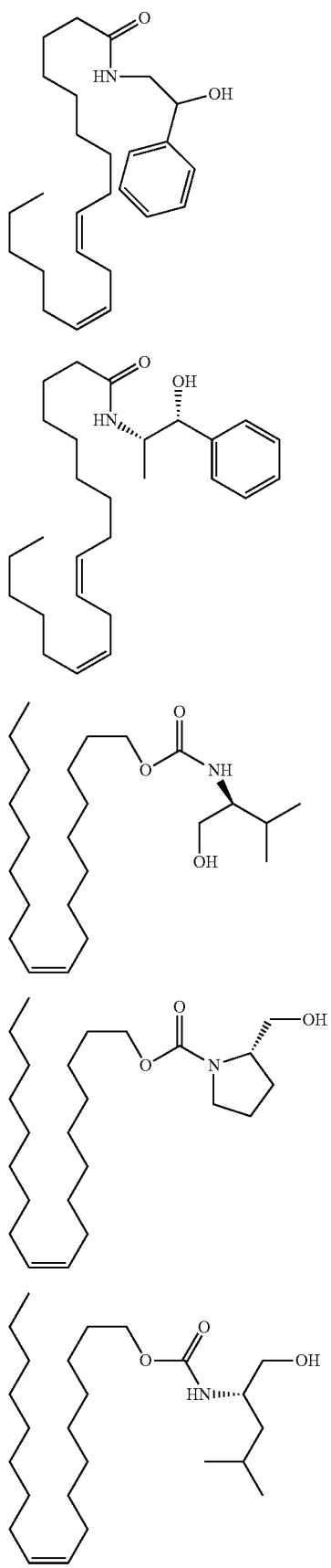
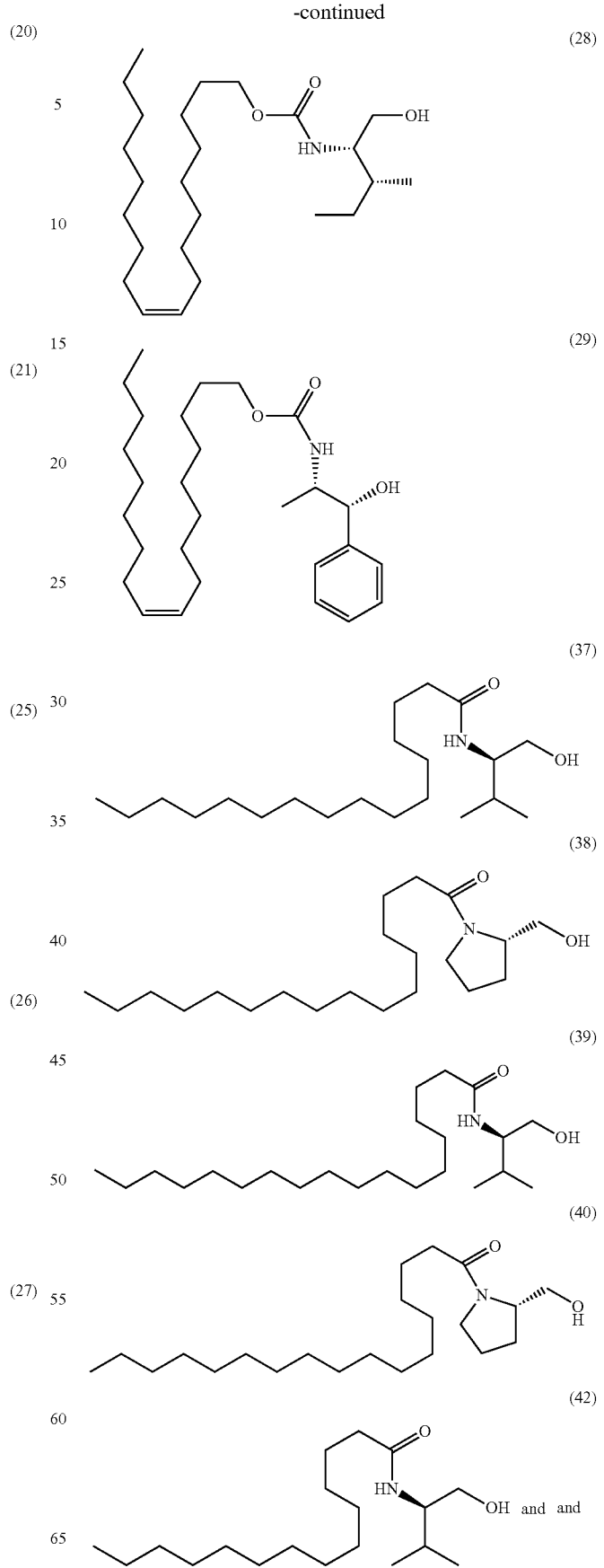

(45)

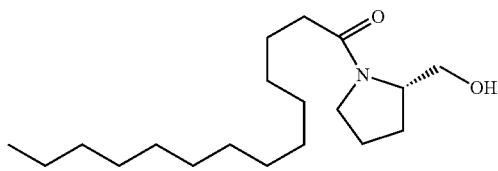

All stereoisomers, optical and geometrical isomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. Compounds comprising amino acid residues include residues of D-amino acids, L-amino acids, or racemic derivatives of amino acids. In addition, several of the compounds of the invention contain one or more double bonds. The present invention intends to encompass all structural and geometrical isomers including cis, trans, E and Z isomers.

One or more of the compounds of the invention, may be present as a salt. The term "salt" encompasses both basic and acid addition salts, including but not limited to acid addition salts with amine nitrogens, and include salts formed with the organic and inorganic anions and cations. Furthermore, the term includes salts that form by standard acid-base reactions with basic groups (such as amino groups) and organic or inorganic acids. Such acids include hydrochloric, hydrofluoric, hydrobromic, trifluoroacetic, sulfuric, phosphoric, acetic, succinic, citric, lactic, maleic, fumaric, cholic, pamoic, mucic, D-camphoric, phthalic, tartaric, salicyclic, methanesulfonic, benzenesulfonic, p-toluenesulfonic, sorbic, picric, benzoic, cinnamic, and like acids.

The term "organic or inorganic cation" refers to counterions for an acid, for example the carboxylate anion of a carboxylate salt. The counter-ions can be chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., *J. Pharm. Sci.*, 66:1-19 (1977), which is incorporated herein by reference. Furthermore, any zwitterionic form of the instant compounds formed by a carboxylic acid and an amino group are also contemplated.

The present invention also includes solvates of the compounds of the present invention and salts thereof "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR spectra, melting point, and the like.

Therapeutic Use

As described herein, the compounds of the present invention are effective at reducing body weight and therefore have utility in the treatment of obesity of complications arising therefrom. The compounds of the invention also improve cognitive function and thus have utility in the treatment of diseases and conditions associated with decreased cognitive function.

The present invention thus relates to a method for treating or reducing the severity of obesity in a subject, comprising the step of administering to the subject a compound according to the present invention, in an amount effective to treat or reduce the severity of obesity in the subject. In another embodiment, the invention provides a method for treating or reducing the severity of a complication of obesity a subject, comprising the step of administering to the subject a compound according to the present invention, in an amount effective to treat or reduce the severity of the obesity complication in the subject. In another embodiment, the invention provides a method for promoting, increasing or facilitating weight loss in a subject, comprising the step of administering to the subject a compound according to the present invention, in an amount effective to promote, increase or facilitate weight loss in the subject. In another embodiment, the invention provides a method of suppressing, inhibiting or reducing appetite of a subject, comprising the step of administering to the subject a compound according to the present invention, in an amount effective to suppress, inhibit or reduce the appetite of the subject. In another embodiment, the invention provides a method of decreasing body mass index (BMI) in a subject, comprising the step of administering to the subject a compound according to the present invention, in an amount effective to decrease BMI in the subject. In another embodiment, the invention provides a method of decreasing food consumption in a subject, comprising the step of administering to the subject a compound according to the present invention, in an amount effective to decrease food consumption in the subject.

In another embodiment, the invention relates to the use of a compound according to the present invention, or a pharmaceutical composition comprising such compound, for the manufacture of a medicament for treating or reducing the severity of obesity or a complication of obesity, increasing or facilitating weight loss, suppressing, inhibiting or reducing appetite, decreasing body mass index (BMI), decreasing food consumption, or improving cognitive function.

In another embodiment, the invention relates to a compound according to the present invention, or to a pharmaceutical composition comprising such compound, for use in treating or reducing the severity of obesity or a complication of obesity, increasing or facilitating weight loss, suppressing, inhibiting or reducing appetite, decreasing body mass index (BMI), decreasing food consumption, or improving cognitive function.

The term "obesity" is defined as an increase in body weight beyond the limitation of skeletal and physical requirement, as the result of excessive accumulation of fat in the body. Obesity can be defined in absolute or relative terms. In practical settings, obesity is typically evaluated in absolute terms by measuring BMI, but also in terms of its distribution through waist circumference or waist-hip circumference ratio measurements.

The term "body mass index" or "BMI" is a simple and widely used method for estimating body fat. BMI is calculated by dividing the subject's weight by the square of his/her height, typically expressed either in metric units (BMI=kg/m$^2$) or US customary units (BMI=lb*703/in$^2$). The current definitions commonly in use establish the following values: A BMI less than 18.5 is considered underweight; a BMI of 18.5 to 24.9 is considered normal weight, a BMI of 30.0-39.9 is considered obese, and a BMI of 40.0 or higher is severely (or morbidly) obese. A BMI of 35.0 or higher in the presence of at lease one other comorbidity is also classified by some bodies as morbid obesity.

Complications of obesity include, but are not limited to, diabetes (Type II diabetes), dyslipidemia, hyperinsulinaemia, hypertension, heart disease, thromboembolism, osteoarthritis, gout, varicose veins, increased incidence of stroke, low self esteem, hirsutism, sweating, hypoventilation, sleep apnea, respiratory problems such as breathlessness, cancer (including breast cancer, cancer of the colon, cancer of the uterus and cancer of the pancreas), kidney disease, gallstones, gallbladder disease, infertility, problems with pregnancy, menorrhagia, and accelerated morbidity and mortality.

The term "diabetes" means a relative or absolute lack of insulin leading to uncontrolled carbohydrate metabolism. Most patients can be clinically classified as having either insulin-dependent diabetes mellitus (IDDM or Type-1 diabetes) or non-insulin-dependent diabetes mellitus (NIDDM or Type-II diabetes).

The term "hyperinsulinaemia" refers to a syndrome with excessively high insulin levels in the blood. It may cause hypoglycemia. The etiology of hyperinsulinism varies, including hypersecretion of a beta cell tumor (insulinoma); autoantibodies against insulin (insulin antibodies); defective insulin receptor (insulin resistance); or overuse of exogenous insulin or hypoglycemic agents.

The term "increased blood pressure" or "hypertension" refers to a repeatedly high blood pressure above 140 over 90 mmHg. Chronically high blood pressure can cause blood vessel changes in the back of the eye, thickening of the heart muscle, kidney failure, and brain damage.

The term "heart disease" refers to a number of abnormal conditions affecting the heart and the blood vessels in the heart. Types of heart disease include:

A) Coronary artery disease (CAD)—the most common type and is the leading cause of heart attacks, and is characterized by hard and narrow arteries, making it difficult for blood to get to the heart. CAD can lead to Angina, which is chest pain or discomfort that happens when the heart does not get enough blood.

B) Heart attack. A heart attack occurs when an artery is severely or completely blocked, and the heart does not get the blood it needs for more than 20 minutes.

C) Heart failure occurs when the heart is not able to pump blood through the body as well as it should and consequently other organs do not receive enough blood.

D) Heart arrhythmias are changes in the beat of the heart. Most people feel dizzy, faint, out of breath or had chest pains at one time.

The term "thromboembolism" refers to formation in a blood vessel of a clot (thrombus) that breaks loose and is carried by the blood stream to plug another vessel. The clot may plug a vessel in the lungs (pulmonary embolism), brain (stroke), gastrointestinal tract, kidneys, or leg. Thromboembolism is an important cause of morbidity (disease) and mortality (death), especially in adults. Treatment may involve anticoagulants (blood thinners), aspirin, or vasodilators (drugs that relax and widen vessels).

The term "osteoarthritis" refers to a non-inflammatory degenerative joint disease occurring chiefly in older people, characterized by degeneration of the articular cartilage, hypertrophy of bones and the margins and changes in the synovial membrane. It is accompanied by pain and stiffness, particularly after prolonged activity.

The term "gout", a disease created by a buildup of uric acid. In this condition, monosodium urate or uric acid crystals are deposited on the articular cartilage of joints, tendons and surrounding tissues due to elevated concentrations of uric acid in the blood stream. This provokes an inflammatory reaction of these tissues.

The term varicose veins, refers to enlarged veins that are swollen and raised above the surface of the skin. They can be dark purple or blue, and look twisted and bulging. Varicose veins are commonly found on the backs of the calves or on the inside of the leg. They develop when valves in the veins that allow blood to flow toward the heart stop working properly. As a result, blood pools in the veins and causes them to get larger.

The term "stroke" refers to damage to nerve cells in the brain due to insufficient blood supply often caused by a bursting blood vessel or a blood clot.

The term "hirsutism" refers to excessive and increased hair growth in women in locations where the occurrence of terminal hair normally is minimal or absent. It refers to a male pattern of body hair (androgenic hair) and it is of cosmetic and psychological concern.

The term "hypoventilation" (also known as respiratory depression) occurs when ventilation is inadequate to perform needed gas exchange. It generally causes an increased concentration of carbon dioxide (hypercapnia) and respiratory acidosis.

The term "sleep apnea" refers to a sleep disorder characterized by pauses in breathing during sleep. These episodes, called apneas, each last long enough so one or more breaths are missed, and occur repeatedly throughout sleep. The standard definition of any apneic event includes a minimum 10 second interval between breaths.

The term "gallbladder disease" includes inflammation, infection, stones, or obstruction of the gallbladder.

The term "cancer" includes all types of neoplasm whether in the form of solid or non-solid tumors, from all origins, and includes both malignant and premalignant conditions as well as their metastasis. For example, this term refers to: carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, invasive ductal carcinoma, papillary adenocarcinoma, ovarian cancer, prostate cancer, squamous cell carcinoma, basal cell carcinoma, adenocarcinoma (well differentiated (wd), moderately differentiated (md), poorly differentiated (pd), undifferentiated (ud)), renal cell carcinoma, hematoma, bile duct carcinoma, melanoma, choriocarcinoma, seminoma, embryonal carcinoma, Wilms' tumor, cervical cancer, testicular tumor, lung carcinoma, small cell, non-small cell and large cell lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, cancer of the thyroid, head and neck cancer, brain cancer, cancer of the peripherial nervous system, cancer of the central nervous system, neuroblastoma, cancer of the endometrium, lymphoproliferative diseases, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, skin cancer, kidney cancer, hypernephroma, hypernephroid adenocarcinoma, bone cancer, liver cancer, melanoma and stomach cancer, as well as metastasis of all the above.

The term "menorrhagia" refers to an abnormally heavy and prolonged menstrual period at regular intervals. Causes may be due to abnormal blood clotting, disruption of normal hormonal regulation of periods or disorders of the endometrial lining of the uterus. Depending upon the cause, it may be associated with abnormally painful periods (dysmenorrhea).

As contemplated herein, the compounds of the present invention, especially Compound X, are useful in improving cognition or cognitive function. Thus, in another embodiment, the invention provides a method of improving cognitive function in a subject, comprising the step of administering to the subject a compound according to the present invention, in an amount effective to improve cognitive function in the subject.

In certain embodiments, the subject is suffering from, or at risk of developing, a cognitive disorder which leads to a decrease in the cognitive function of the individual. For example, the subject may be suffering, or at risk of developing, a cognitive disorder selected from the group consisting of dementia, delirium, amnesia, aphasia, Alzheimer's disease, vascular dementia, multi-infarct dementia, Binswanger's disease, dementia with Lewy bodies (DLB), alcohol-induced persisting dementia, frontotemporal lobar degenerations (FTLD), Pick's disease, frontotemporal dementia, frontal variant FTLD, semantic dementia, temporal variant FTLD, progressive non-fluent aphasia, Creutzfeldt-Jakob disease, Huntington's disease, Parkinson's disease, AIDS dementia complex, an attention disorder, attention-deficit disorder (ADD), attention-deficit hyperactivity disorder (ADHD), age-related cognitive dysfunction and stress-induced cognitive dysfunction including post-traumatic stress disorder.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

A "therapeutic" treatment is a treatment administered to a subject who exhibits signs of pathology for the purpose of diminishing or eliminating those signs. A "therapeutically effective amount" of a compound of the invention is that amount of compound which is sufficient to provide a beneficial effect to the subject to which the compound is administered.

In other embodiments of the use of preparing a medicament, the medicament additionally comprises at least one other therapeutic agent or treatment regimen useful for the treatment of obesity of for promoting weight less and/or reducing BMI. In certain embodiments, the compounds of the invention may be administered alongside with at least one traditional medicine or therapeutic regimen (e.g., exercise and/or diet regimen) that is effective at treating obesity. The administration can be concurrent (either combined in one dosage form or in separate dosage forms) or sequential. If provided sequentially, the compound of the invention can be administered before or after treatment with the additional agent(s). The combination of a compound of the invention and the traditional drug may allow administration of a lower dosage of the traditional drug, and thus the side effects experienced by the subject may be significantly lower, while a sufficient therapeutic effect is nevertheless achieved.

Without wishing to be bound by any particular mechanism or theory, one possible mode of action of the compounds of the invention are by affecting PPAR-α by the same mechanism or a similar mechanism as KDS-5104 (Guiseppe et al.). It is apparent to a person of skill in the art that the mechanism of action of the compounds of the invention in no way limits the broad scope of the invention, including the novel fatty acid derivatives and their therapeutic use.

Pharmaceutical Compositions

Although the fatty acid derivatives of the present invention can be administered alone, it is contemplated that these compounds will be administered in a pharmaceutical composition containing the fatty acid derivative together with a pharmaceutically acceptable carrier or excipient.

The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, or via a suppository. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In another embodiment, the fatty acid derivatives can be added to a person's diet by mixing them with food or drink.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. Adjuvants for topical or gel base forms may include, for example, sodium carboxymethylcellulose, polyacrylates, polyoxyethylene-polyoxypropylene-block polymers, polyethylene glycol and wood wax alcohols.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

A compound of the present invention can be delivered in formulations adapted for immediate release, in a controlled release system adapted to release the compound over a prolonged period of time, or in delayed release formulations adapted to release the active ingredient after a certain delay period.

Furthermore, at times, the pharmaceutical compositions may be formulated for parenteral administration (subcutaneous, intravenous, intraarterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, 0.1 mg/kg to 100 mg/kg and even more preferably 1 mg/kg to 10 mg/kg. Effective doses may be extrapolated from dose-response curves derived from in vitro or animal model test bioassays or systems.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXPERIMENTAL DETAILS SECTION

Example 1

Effect of Compound X on Body Weight and Total Food Consumption

Young female Sabra mice were assigned at random to different groups (untreated controls or treated with 1 mg/kg Compound X Intra Peritoneally) of 10 mice per cage. The weights of the animals were similar at the beginning of the experiment. All cages contained wood-chip bedding and were placed in a temperature-controlled room at 22° C., on a 12-h light/dark cycle (lights on at 07.00 h). The mice had free access to water 24 h a day. The mice were fed ad-libitum, body weight was measured twice a week during the experiment and food consumption was calculated.

As seen in FIG. 1A, there was a significant decrease in body weight (about 10%) shortly after administration of Compound X (1 mg/kg) ($p<0.001$). The decrease in weight lasted about 15 days after administration.

Figure 1B:
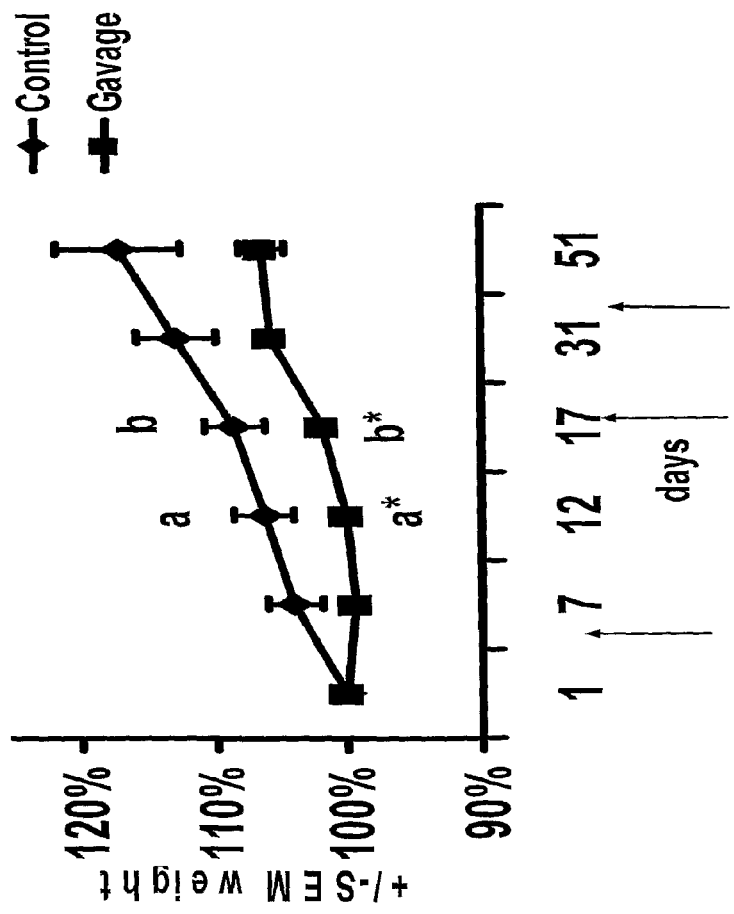
FIG. 1B: Administration by oral gavage.

Compound X may also be given orally. Compound X (gavage) or saline (control) were administered to Sabra mice by oral gavage. A shown in FIG. 1B, there was a significant difference between the weights of the two groups, with compound X significantly decreasing the weight of the animals.

Figure 2A:
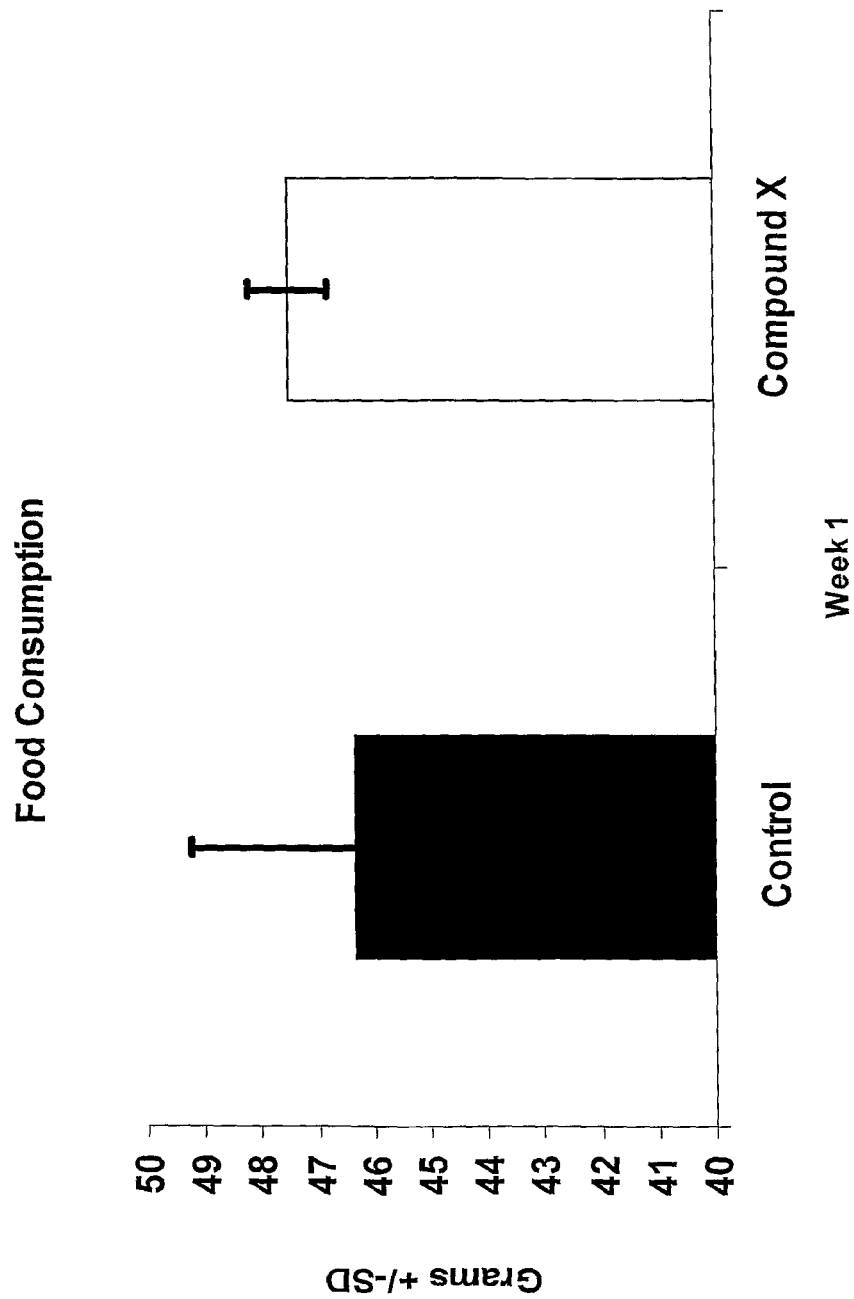
FIGS. 2A and B: shows the effect of Compound X on total food consumption (in grams) in mice one week before treatment (FIG. 2A) and at the second week during treatment (FIG. 2B).
Figure 2B:
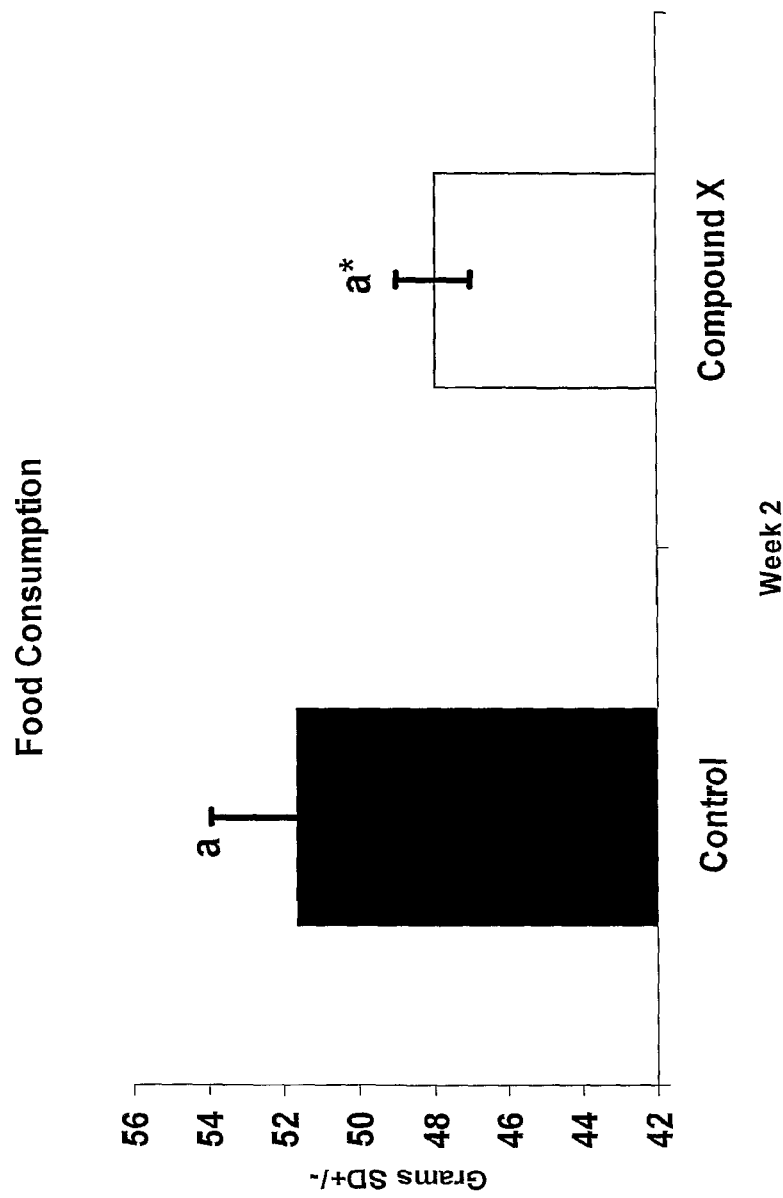

Total food consumption was evaluated in the first week before treatment and at the second week during the treatment (FIGS. 2A and 2B). As seen, Compound X significantly decreased food consumption in the second week ($P<0.05$).

Example 2

Effect of Compound X on Cognitive Function and Activity

Figure 3:
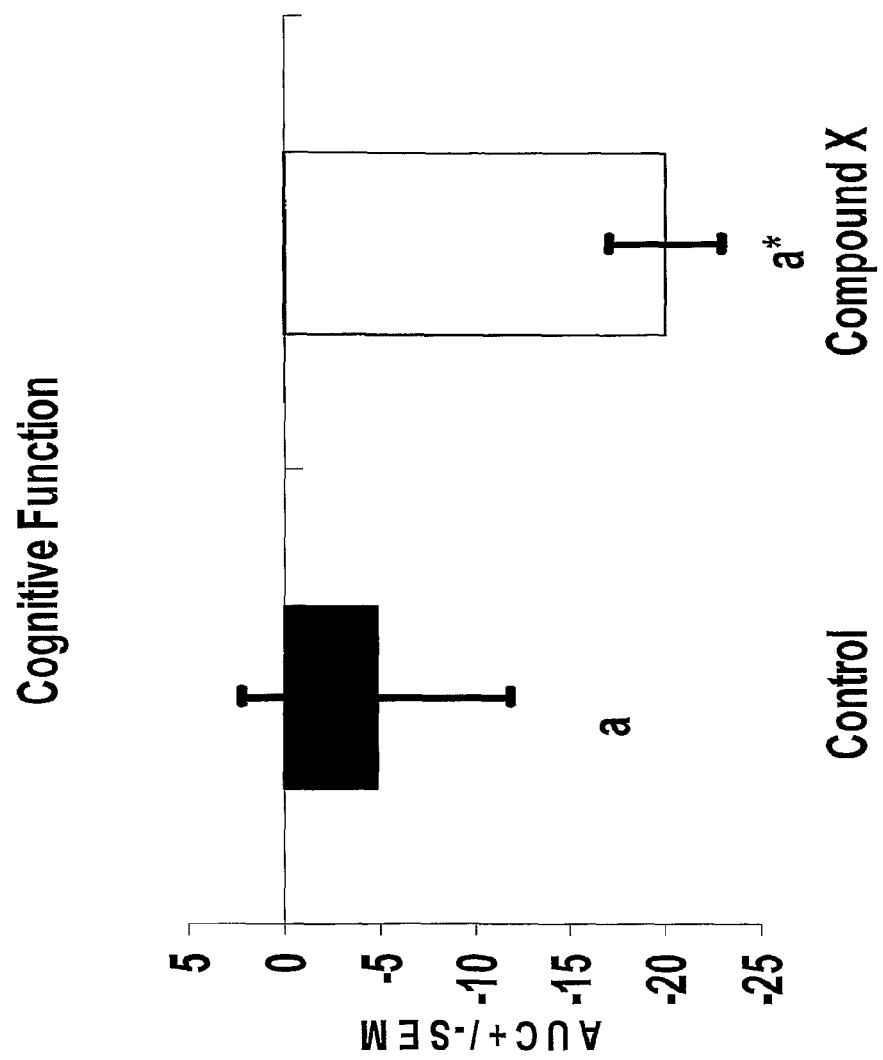
FIG. 3: shows the effect of Compound X on cognitive function in mice as evaluated by an 8 arm maze.

Mice were subjected to the treatment regimen outlined in Example 1, and during the second week of treatment their cognitive function was evaluated by an 8 arm maze on the second week of the experiment 15 minutes after injection. Two hours before the test, the mice were on a water deprivation schedule. At the end of each arm there was a drop of water as a reward. Each mouse was evaluated for its performance in the maze. The mice were observed until they made entries to all eight arms or until they completed 24 entries (whichever came first). The results, depicted in FIG. 3, were calculated as AUC (area under the curve) as follows: day2+day3+day4+day5−4(day1). As seen in FIG. 3, cognitive function was improved significantly by treatment with Compound X.

Figure 4:
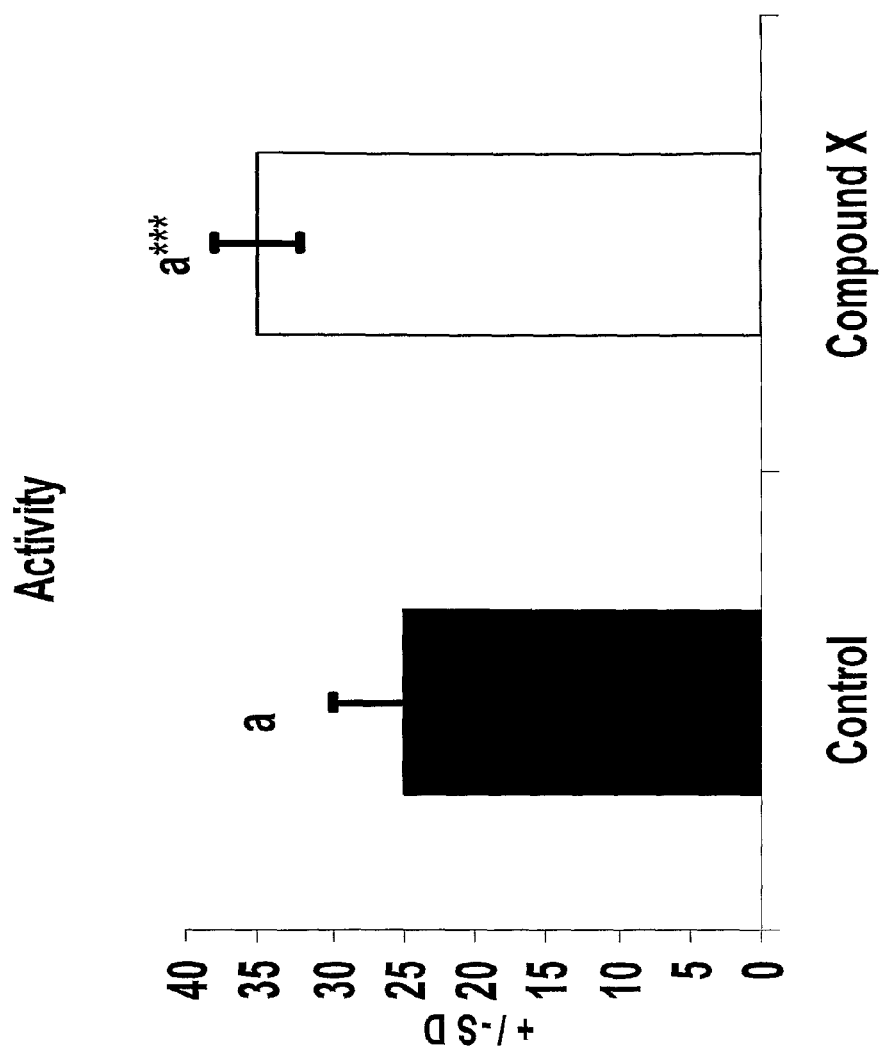
FIG. 4: shows the effect of Compound X on the activity index in mice.

Activity of the mice was assessed in an open field (20×30 cm) divided into 12 squares of equal size. Two mice were observed simultaneously for 5 minutes. The activity test was performed on day 11 of the experiment. Locomotor activity was recorded by counting the number of crossings by the mice at one minute intervals. The results, depicted in FIG. 4, are presented as the mean number of crossings per minute. As seen, there is a significant increase in the activity following Compound X administration ($p<0.001$).

Figure 5:
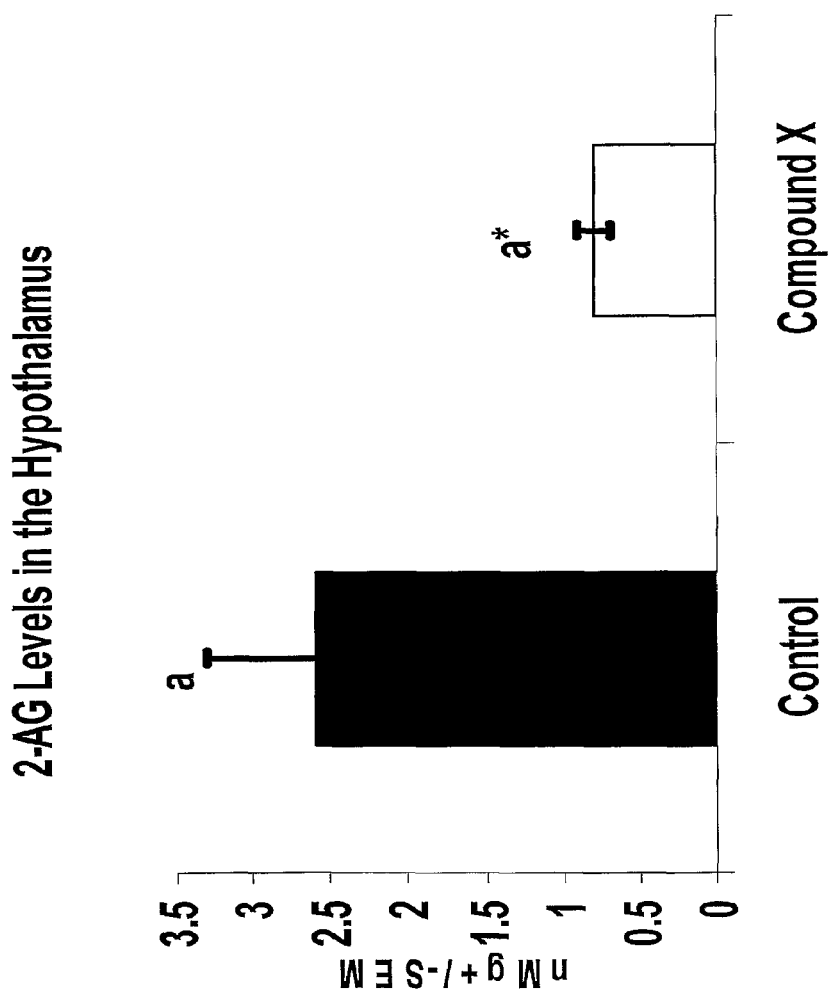
FIG. 5: shows the effect of Compound X on 2-AG levels in the Hypothalamus.

Mice were decapitated and their brains rapidly removed, and the hypothalamus and hippocampus were dissected. 2-AG levels in the hypothalamus were evaluated using TLC followed by GC-MS analysis. As shown in FIG. 5, there is significant decrease in brain 2-AG levels in the hypothalamus in the treated group vs. control ($p<0.05$).

Figure 6:
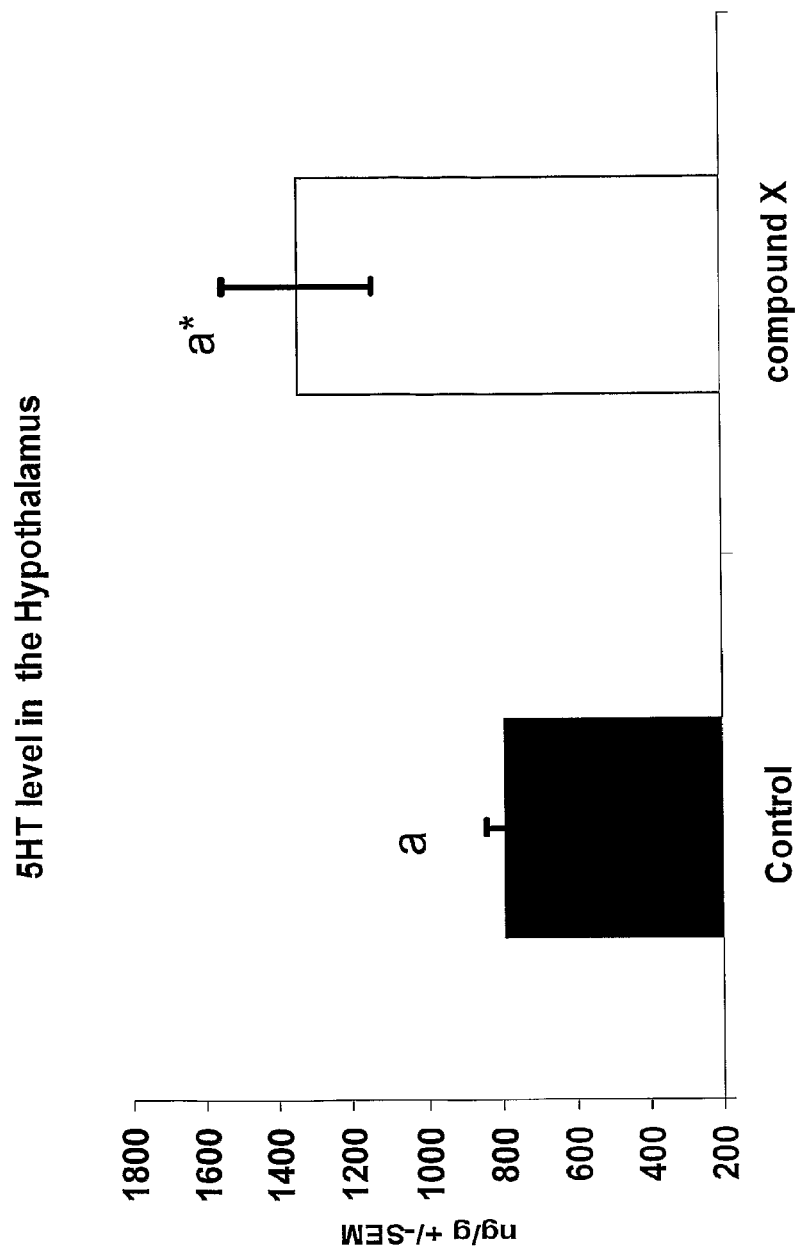
FIG. 6: shows the effect of Compound X on 5HT levels in the Hypothalamus.
Figure 7A:
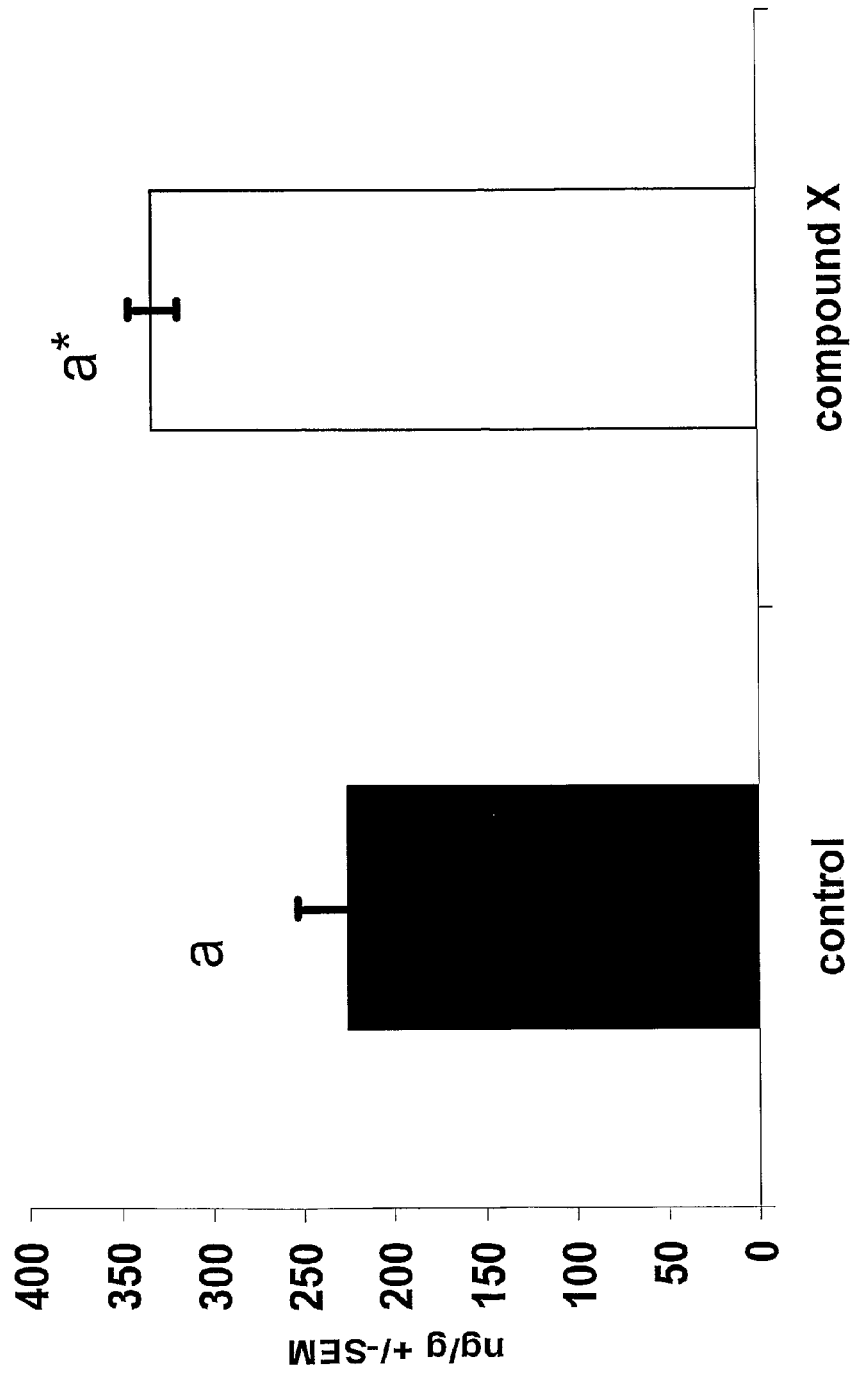
FIGS. 7A and 7B: show the effect of Compound X on Norepinephrine levels in the Hippocampus (7A) and Hypothalamus (7B).
Figure 7B:
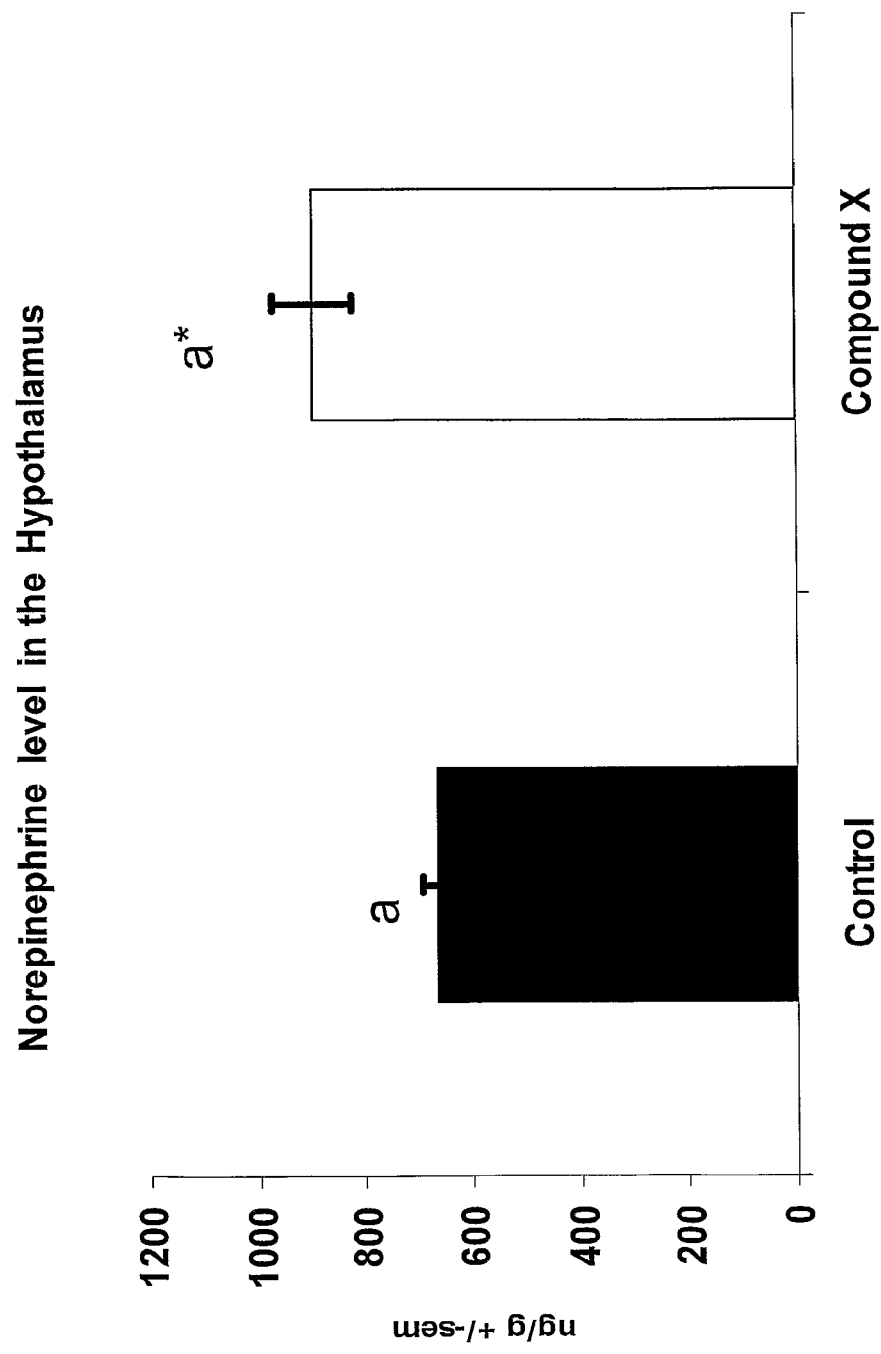

Serotonin (5-HT) and norepinephrine (NE) were valuated in the hypothalamus (serotonin and norepinephrine) and hippocampus (norepinephrine), using HPLC-ECD. As shown in FIG. 6, serotonin levels in the hypothalamus increased significantly in the treated group vs. control ($p<0.05$). FIGS. 7A and 7B show that NE levels also significantly increased in the hippocampus (FIG. 7A) and hypothalamus (FIG. 7B) upon treatment with compound X ($p<0.05$).

In conclusion, Compound X caused immediate decrease in body weight (10%, $p<0.001$), which was related to a 7% decrease in food consumption ($p<0.05$), 36% increased activity ($p<0.001$), decreased 2-AG levels ($p<0.05$) and increased 5-HT and NE levels in the hypothalamus. Treatment with Compound X also resulted in 400% improvement in cognitive function as evaluated by an 8 arm maze, and this correlated with the increase in NE levels in the hippocampus ($p<0.05$). The effect of compound X resembles the effect of moderate caloric restriction (to 60%) which has previously been shown to be beneficial Avraham Y., Bonne O B, Berry E. M., 1996. Behavioral and neurochemical alterations caused by diet restriction—The effect of tyrosine administration in mice. *Brain Research* 732, 133-144). Moreover, Compound X is derived from two natural products, namely oleic acid and valinol which is a derivate of valine obtained by reduction of the carboxyl group of valine to a hydroxyl group, and can conveniently be administered orally or by i.p. administration.

Example 3

Comparison Between Compound X and Rimonabant (SR141716A)

Rimonabant (SR141716A, Acomplia) is an anorectic anti-obesity drug, which is an inverse agonist of the cannabinoid receptor CB1. Rimonabant was the first selective CB1 receptor blocker to be approved for use anywhere in the world. In Europe, it was indicated for use in conjunction with diet and exercise for patients with a BMI greater than 30 kg/m$^2$, or patients with a BMI greater than 27 kg/m$^2$ with associated risk factors, such as type 2 diabetes or dyslipi-daemia. In the UK, was available beginning in July 2006. As of 2008, the drug was available in 56 countries. On 23 Oct. 2008, the European Medicines Agency (EMEA) released a press release stating that its Committee for Medical Products for Human Use (CHMP) had concluded that the benefits of Acomplia no longer outweighed its risks and subsequently recommended that the product be suspended from the UK market. Sanofi-Aventis later released a press statement stating that the drug had been suspended This study compared the effects of Compound X and Rimonabant. Female Sabra mice (32 g average weight) were divided randomly to 3 experimental groups: (a) control; (b) Compound X; and (3) Rimonabant, 10 mice in each group. Food consumption and weight were evaluated during the experiment. During the second week, mice were evaluated for cognitive function during 5 days using the eight arm maze. 15 min before evaluation mice were injected i.p. with either saline or 1 mg/kg Compound X or Rimonabant (days 8-12).

Figure 8:
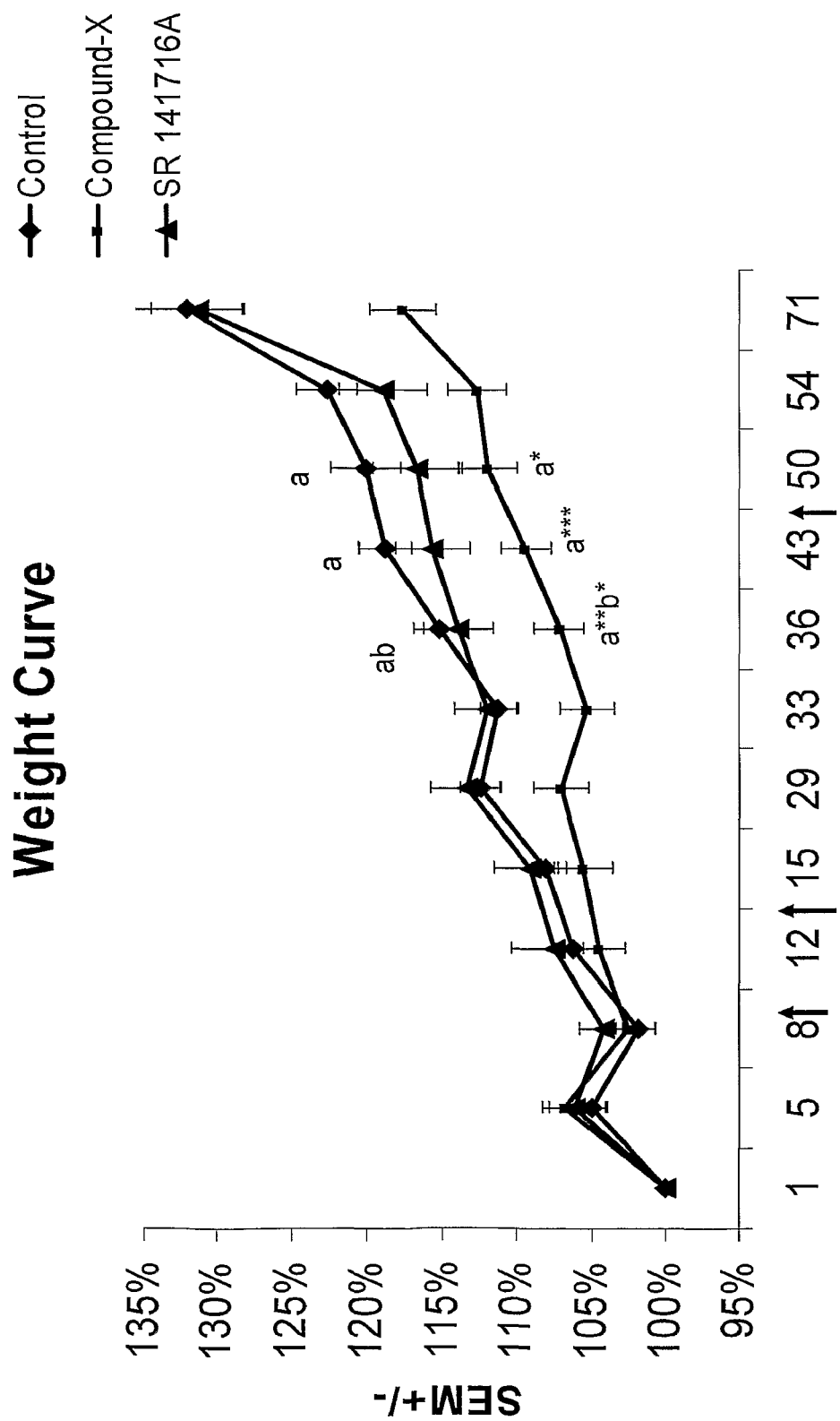
FIG. 8: shows the weight loss effects of Compound X and Rimonabant.

As shown in FIG. 8, Compound X produced a greater sustained weight loss than Rimonabant. Compound X caused significant decrease in weight (p<0.001 ab), while there was no significant difference in weight loss between the control and Rimonabant groups. The effect of Compound X continued for an additional 31 days without further administration. On day 43, it was administered again and the effect continued for an additional 28 days.

Figure 9A:
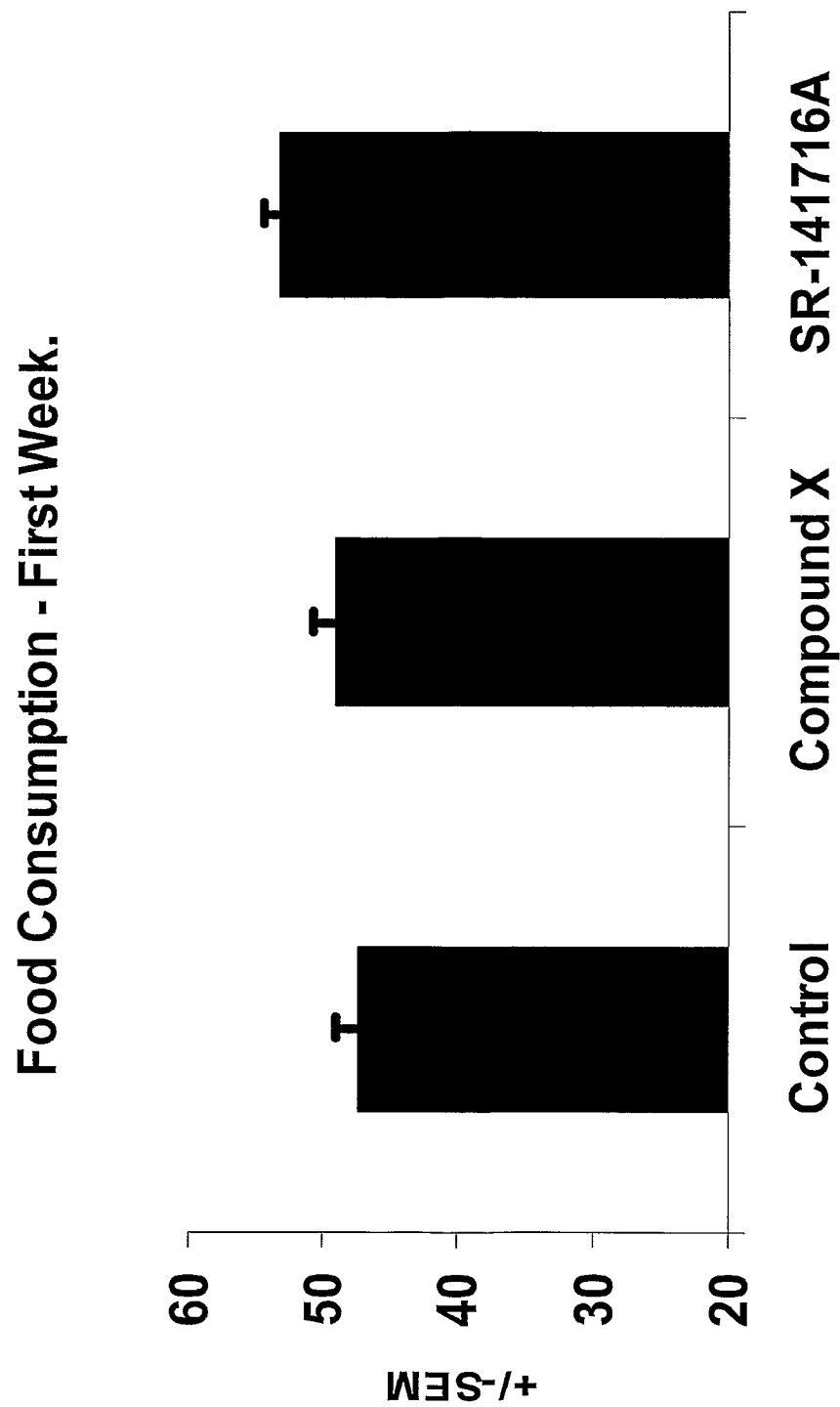
FIGS. 9A and B: show the effects of Compound X and Rimonabant on total food consumption (in grams) in mice one week before treatment (FIG. 9A) and at the second week during treatment (FIG. 9B).
Figure 9B:
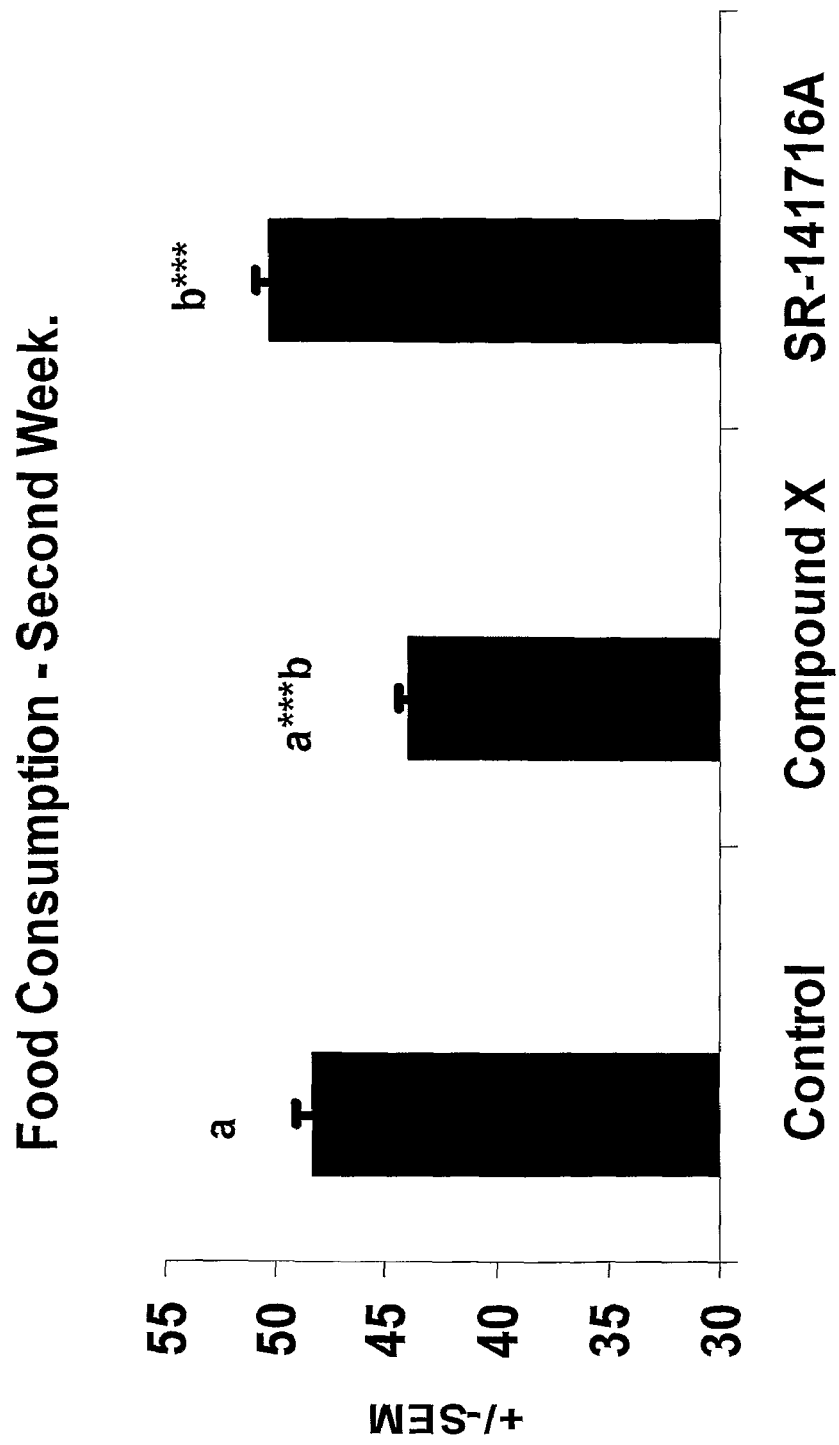

Total food consumption was evaluated in the first week before treatment and at the second week during the treatment (FIGS. 9A and 9B, respectively). As shown, Compound X decreased food consumption significantly (p<0.001ab) in the second week during administration, while there were no significant differences between control and Rimonabant.

Figure 10:
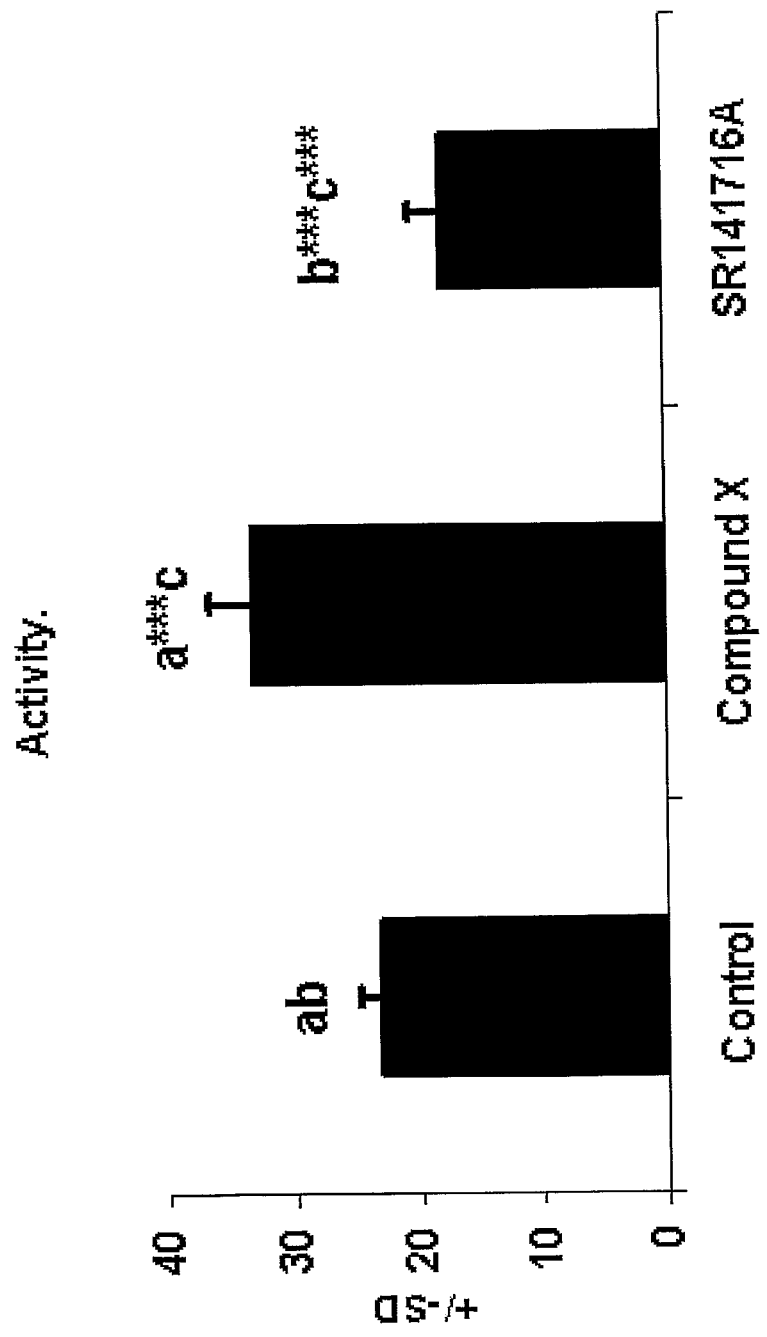
FIG. 10: shows the effects of Compound X and Rimonabant on the activity index in mice.

Activity of the mice was assessed in an open field (20×30 cm) divided into 12 squares of equal size, as detailed in Example 2. The results, depicted in FIG. 10, are presented as the mean number of crossings per minute. As seen, there is a significant increase in the activity following Compound X administration (p<0.001a), while Rimonabant significantly decreased activity (p<0.01bc).

Figure 11:
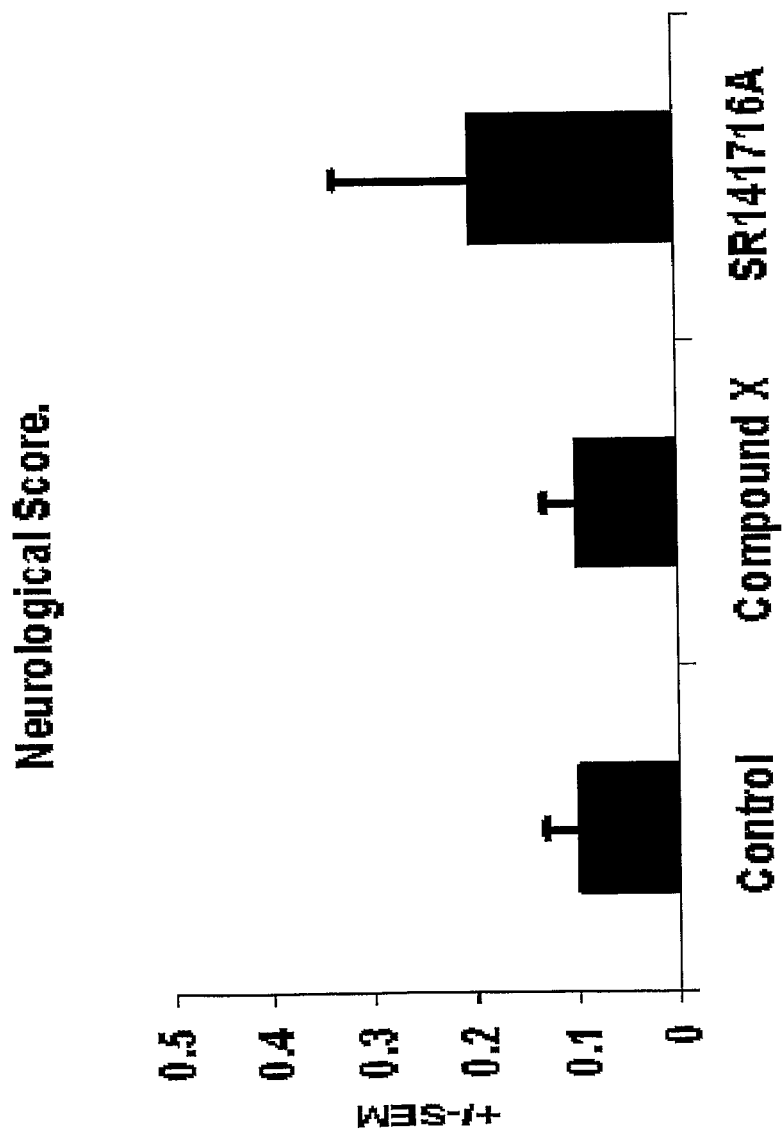
FIG. 11: shows the effects of Compound X and Rimonabant on neurological score.

Neurological score was evaluated by the NSS method Neurological function was assessed by a 10 point scale based on reflexes and task performance 37: Exit from a circle 1 meter in diameter in less than 1 minute, seeking, walking a straight line, startle reflex, grasping reflex, righting reflex, placing reflex, corneal reflex, maintaining balance on a beam 3, 2 and 1 cm in width, climbing onto a square and a round pole. For each task failed or abnormal reflex reaction a score of 1 was assigned. Thus, a higher score indicates poorer neurological function on day 10. As shown in FIG. 11, Compound X did not change the neurological score while Rimonabant showed a tendency to increase it.

Figure 12:
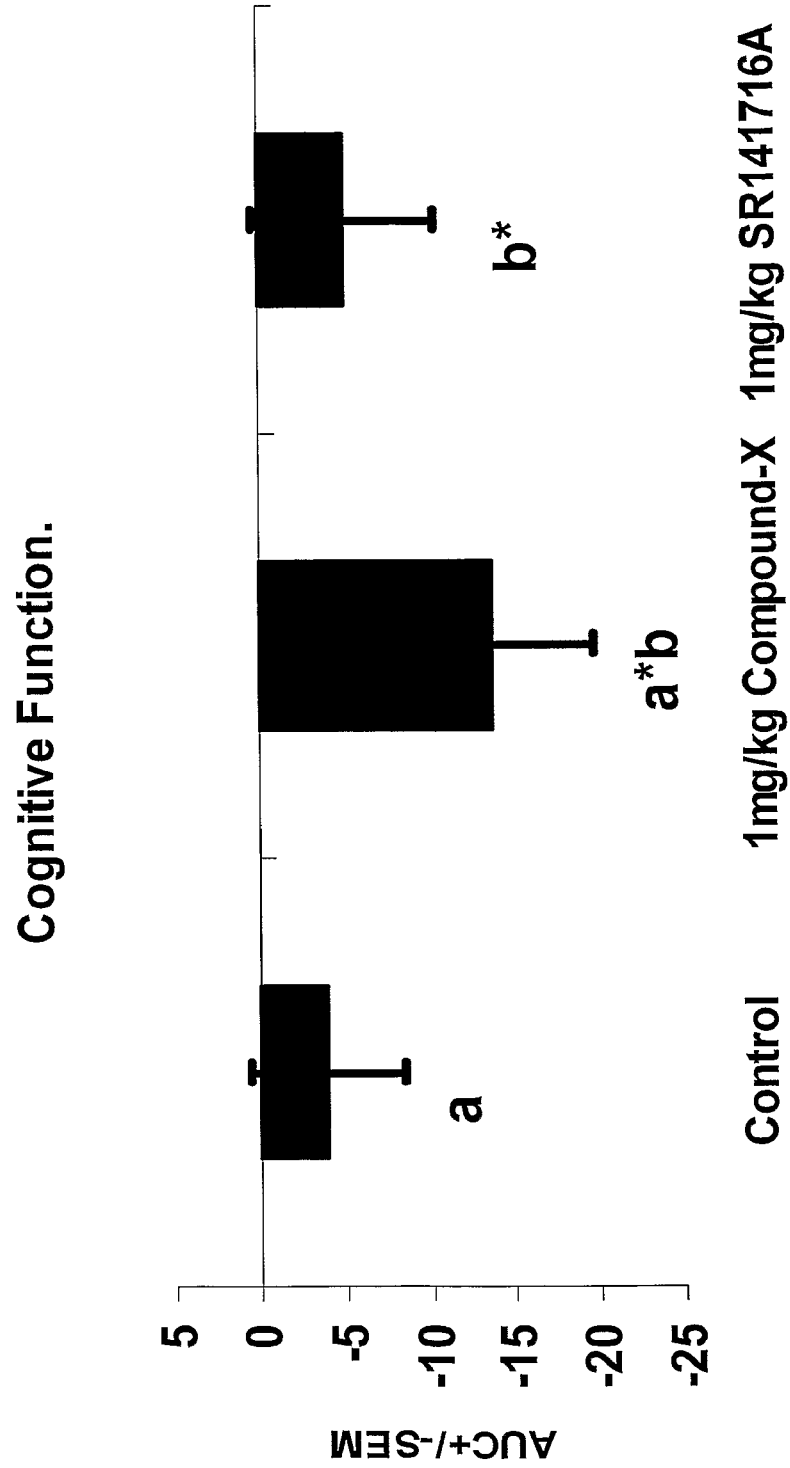
FIG. 12: shows the effects of Compound X and Rimonabant on cognitive function in mice as evaluated by an 8 arm maze.

Mice were subjected to treatment with Compound X (1 mg/kg) or Rimonabant (1 mg/kg), and during the second week of treatment their cognitive function was evaluated by an 8 arm maze as described above in Example 2. As seen in FIG. 12, cognitive function was improved significantly by treatment with Compound X (p<0.05a), while Rimonabant did not significantly affect cognitive function.

Figure 13:
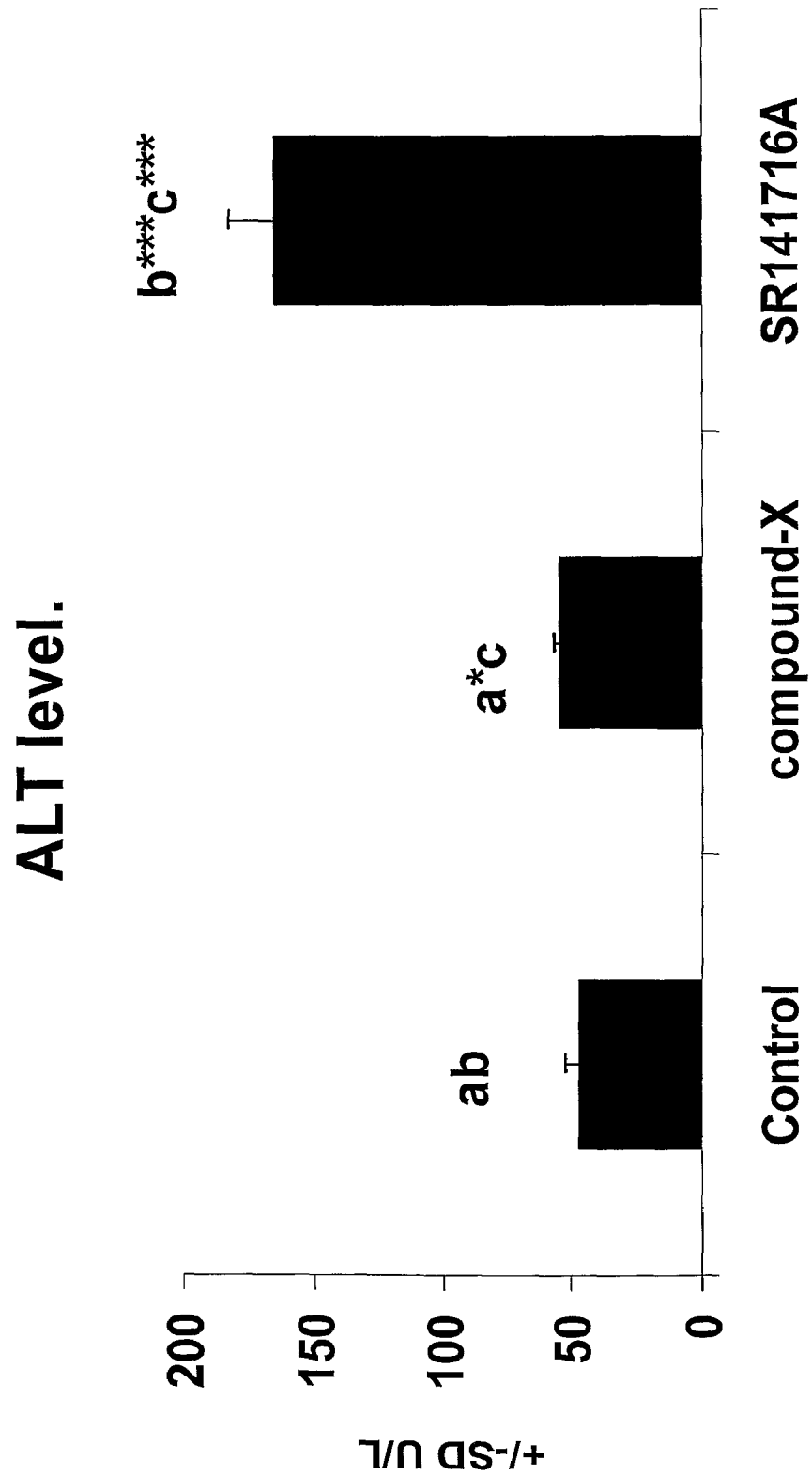
FIG. 13: shows the effects of Compound X and Rimonabant on ALT levels.

Mice were sacrificed 71 days after treatment, and ALT levels were measured. As shown in FIG. 13, Compound X slightly increased ALT levels (p<0.05a), while Rimonabant raised them significantly (p<0.001b).

In sum, 1 mg/kg Compound X decreased the animal weight significantly, which was related to decreased food consumption and increased activity, it improved cognitive function without affecting neurological score, it increased ALT levels slightly and it may be given orally. In contrast 1 mg/kg Rimonabant almost did not affect weight, food consumption and cognitive function, it decreased activity and showed tendency to impair neurological score. It greatly elevated ALT levels. In conclusion, 1 mg/kg Rimonabant in mice was not sufficient to produce weight loss while 1 mg/kg Compound X was effective.

Example 4

Synthesis

Abbreviations

DDW, double distilled water; SAR, structure activity relationship; DCC, dicyclohexylcarbodiimide; NHS, N-hydroxysuccinimide; CDI, carbonyldiimidazole; TEA, triethyl amine; DIEA, diisopropyl ethyl amine DMF, dimethylformamide; DCM, dichloromethane; EthAc, ethyl acetate; MeOH; methanol, EtOH; ethanol, ESIMS, electrospray ionization mass spectrometry; NMR, nuclear magnetic resonance; R.T., room temperature;

Materials

Fatty acids: Oleic (Merck), palmitic, myristic, lauric, linoleic, linolenic, were purchased from ACROS Chemicals Ltd, Oleyl alcohol and oleyl amine were purchased from Sigma-Aldrich.

Stearic acid was prepared by reducing oleic acid.

Oleic alcohol ((9Z)-Octadec-9-enoic acid), Oleoyl amine were purchased L-Valinol, Fmoc-D-Valinol, Prolinol, R-Phenyl glycinol, D-Alaninol, R-Phenyl Alaninol, L-Phenyl Alaninol Leucinol, Isoleucinol, Fmoc-Threoninol-(O-tert-Butyl), Fmoc-Isoleucinol, Fmoc-Leucinol, Fmoc-Aspartinol-(O-tert-Butyl) were purchased from GL Biochem (Shanghai) LTD, DCC, NHS, CDI, DMF, DCM, EthAc, were all purchased from ACROS Chemicals Ltd and were used without further purification. Deuterated solvents: $CDCl_3$, $DMSO-d_6$ were purchased from ACROS Chemicals Ltd. Silica gel, thin layer chromatography (TLC) sheets were all purchased from Merck Ltd.

$^1$H-NMR:

Data were collected using on Varian Unity Inova 500 MHz spectrometer equipped with a 5-mm switchable and data were processed using the VNMR software.

Electro-Spray Ionization Mass Spectrometry (ESI-MS):

ESIMS was performed using a ThermoQuest Finnigan LCQ-Duo in the positive ion mode. Elution was in a mixture of 49:49:2 water/methanol/acetic acid at a flow rate of 15 µL/min.

Experimental

Synthesis of Stearic Acid

Synthesis of Trans-Octadec-9-enoic acid (2) [Elaidic acid] (Scheme-1)

Oleic acid (5 g, 17.7 mmol) were dissolved in 20 ml dry acetonitrile and the mixture was refluxed for 24 hours. The solvent was removed under reduced pressure.

$^1$H-NMR ($CDCl_3$, δ ppm):

5.36 (d, 2H), 2.36 (t, 3H), 2.04 (m, 6H), 1.64 (m, 2H), 1.29 (m, 20H), 0.90 (t, 3H)

Scheme-1: Pathway-A: conversion of cis- to trans- (Oleic Acid → (2)

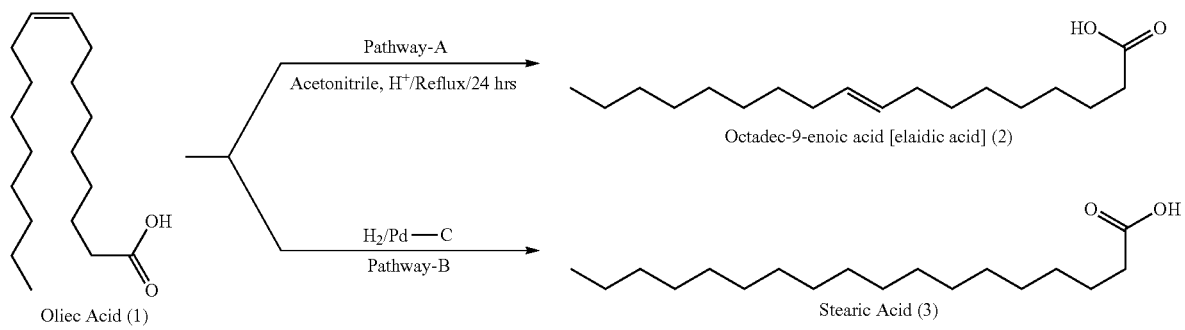

Synthesis of Stearic Acid (3) (Scheme-1)

In the hydrogenation vessel, oleic acid (10 g, 35.4 mmol) were dissolved in 50 ml ethyl acetate. 1 g of 5% Pd—C were added and the vessel was connected to the hydrogenation apparatus and pressure was set at 50 psi for 6 hours. At the end of this period white precipitate of stearic acid was formed. To ensure total solubilization of stearic acid, 400 ml of ethyl acetate were added and the black precipitate was filtered out and washed with additional 100 ethyl acetate. The filtrate was removed which gave stearic acid in quantitative yield.

$^1$H-NMR (CDCl$_3$, δ ppm): 2.35 (t, 2H), 1.63 (m, 2H), 1.25 (m, 28H), 0.88 (t, 3H)

Synthesis of Oleoyl-amide-Amino-ol derivatives

General Procedure:

In a round bottom flask, oleic acid (1) (0.5 g, 5.3 mmol) was dissolved in 20 ml of dry pyridine (kept over KOH). To the solution dry TEA (0.74 ml, 5.33 mmol), DCC (1.1 g, 5.33 mmol), and NHS (0.55 g, 4.85 mmol) were added. The mixture was stirred at room temperature for overnight. After confirming the total conversion of oleic acid to the NHS intermediate using TLC (5% MeOH), the relevant amino-ol derivative (4.85 mmol) was added and the mixture was stirred for additional 24 hours. After completion of the reaction using TLC: (100% Ethyl acetate), the volatiles were removed under reduced pressure to dryness. The gum was dissolved in 5 ml DCM and the desired product Oleoyl amido-ol (10) was obtained using column chromatography Scheme -2: Synthesis of Oleoyl-Derivatives: Oleoyl-L-Valinol (10), -D-Valinol (11), -L-Prolinol (12), -L-Leucinol (13), R-Phenyl Alaninol (14)

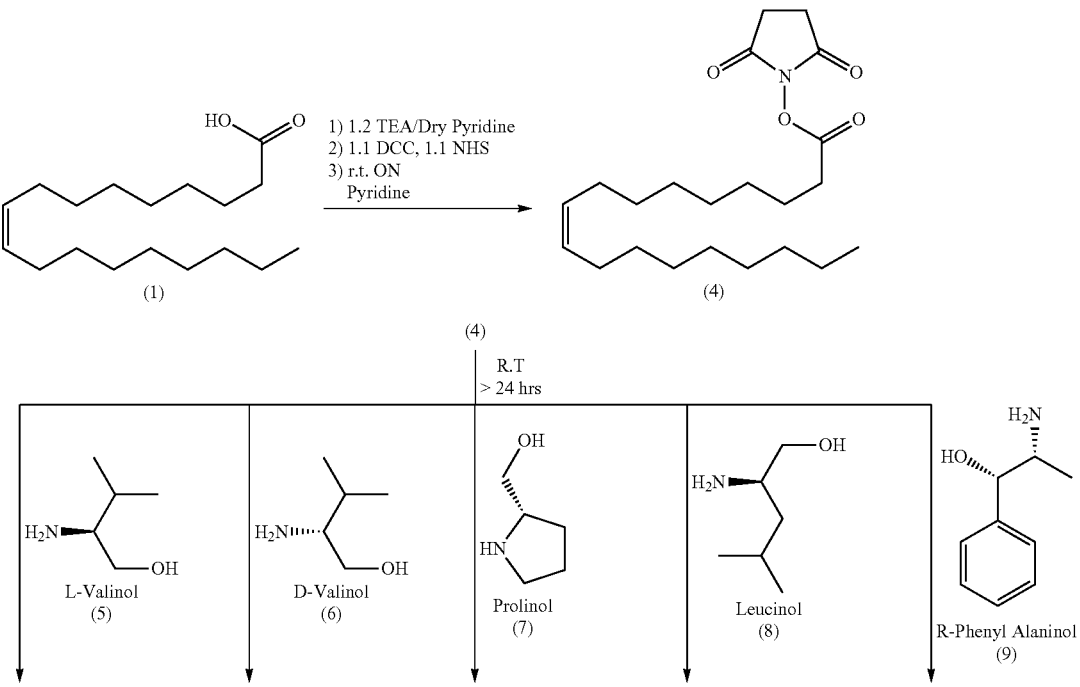

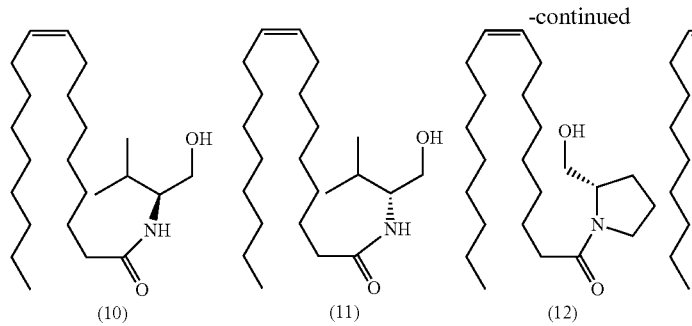
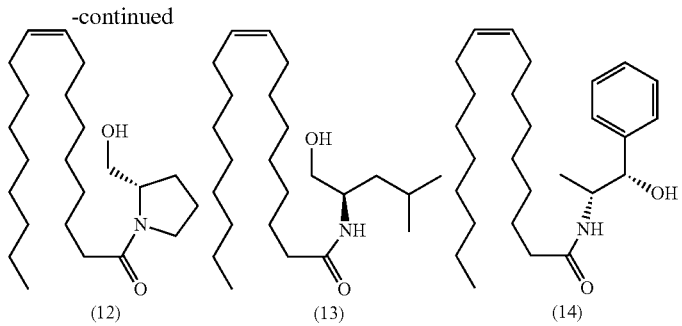

(dichloromethane/ethyl acetate=1:1, v/v)).

Oleoyl-Valinole[Octadec-9-enoic acid (1-hydroxymethyl-2-methyl-propyl)-amide] (10)

In a round bottom flask, oleic acid (1) (1.53 g, 5.33 mmol) was dissolved in 20 ml of dry pyridine (over KOH). To the solution TEA (0.74 ml, 5.33 mmol), DCC (1.1 g, 5.33 mmol), and NHS (0.55 g, 4.85 mmol) were added. The mixture was stirred at room temperature for overnight. After confirming the total conversion of the acid to the NHS intermediate using TLC (5% MeOH), L-Valinol (0.5 g, 4.85 mmol) was added and the mixture was stirred for additional 24 hours. After completion of the reaction (TLC: 100% Ethyl acetate), volatiles were removed under reduced pressure to dryness. The gum was dissolved in 5 ml DCM and the desired product oleoyl-valinol (10) was obtained using column chromatography (dichloromethane/ethyl acetate=1:1, v/v)). Colorless viscous oil (0.94 g, 46.8 yield).

TLC [100% ethyl acetate, I$_2$]: RF=4 cm $^1$H-NMR (CDCl$_3$, δ ppm): 0.93 (q, 3H), 0.98 (m, 6H), 5.32 (dd, 2H), 3.64 (m, 1H), 4.10 (q, 2H), 2.75 (s, 1H), 2 (s, 1H), 2.20 (m, 2H), 1.25 (m, 14H), 1.33 (t, 6H).

Oleoyl-Prolinol[1-(2-Hydroxymethyl-pyrrolidin-1-yl)-octadec-9-en-1-one] (12)

Oleic acid (1) (1.5 g, 5.4 mmol) was dissolved in 20 ml of dry pyridine. To the solution TEA (0.75 ml, 5.4 mmol), DCC (1.1 g, 5.4 mmol) and NHS (0.55 g, 4.9 mmol) were added. The mixture was stirred at r.t. for overnight. TLC (ethyl acetate) showed complete conversion of the starting material to the Oleoyl-NHS intermediate, Prolinol (7) (0.5 g, 4.94 mmol) were added and the reaction was left at r.t. for additional O.N. When reaction was completed, solvents were evaporated to dryness under reduced pressure. The gum was dissolved 20 ml DCM and column chromatography (DCM/ethyl acetate.=1:1; v/v) produced (12) as colorless viscous oil.

(1.17 g, 59.7% yield).

$^1$H-NMR (CDCl$_3$, δ ppm): 5.32 (dd, 2H), 4.10 (q, 2H), 3.62 (m, 1H), 3.46 (t, 2H), 2.28 (m, 2H), 2 (s, 1H), 1.95 (m, 2H), 1.58 (m, 2H), 1.25 (m, 14H), 0.86 (q, 3H), 1.34 (t, 6H).

Synthesis of Linoleic-Amino-Ol Derivatives (17-21, Scheme 3)

Scheme-3: Synthesis of Linoleic-Amino-Ol Derivatives (17-21)

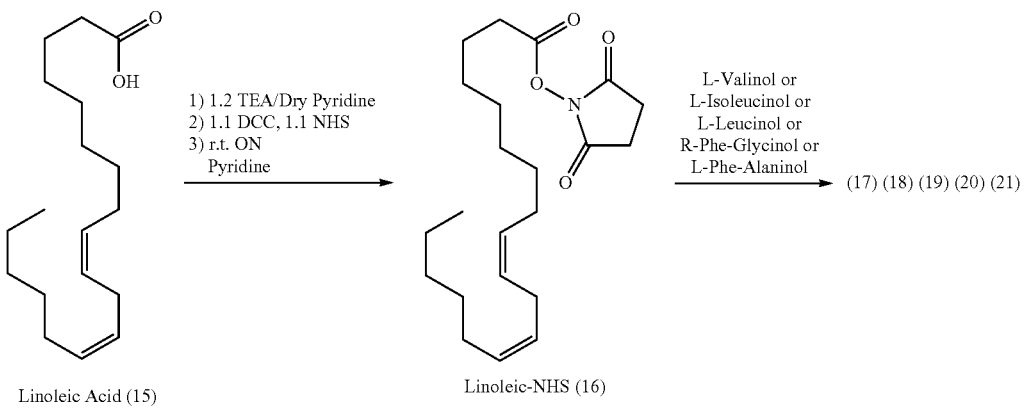

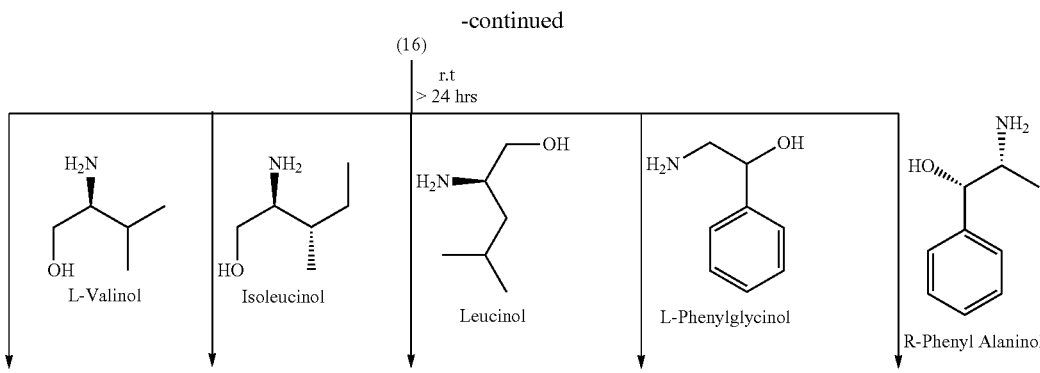

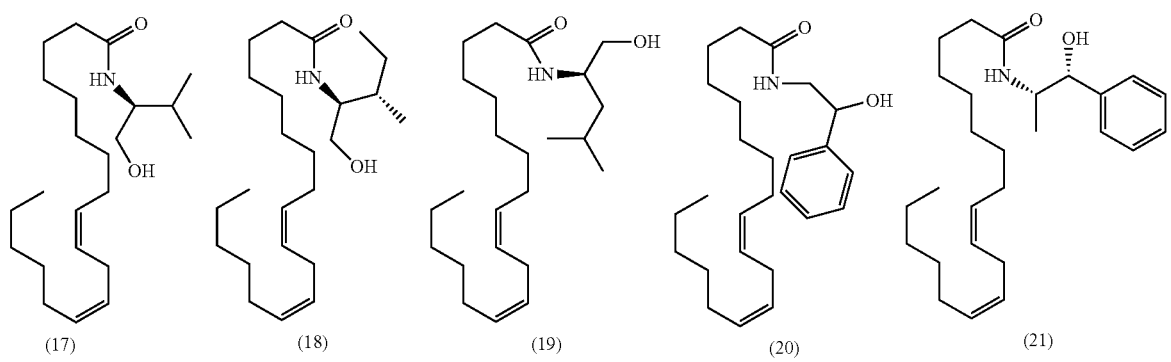

General Procedure:

In a round bottom flask, under calcium chloride tube, Linoleic acid (15) (0.5 g, 1.78 mmol) was dissolved in 15 ml of dry pyridine (dried over KOH). To the solution dry TEA (0.293 ml, 2.1 mmol), DCC (367 mg, 1.96 mmol), and NHS (226 mg, 1.96 mmol) were added. The mixture was stirred at room temperature overnight. After confirming the total conversion of the acid to the NHS activated intermediate using TLC (100% ethyl acetate), the relevant amino-ol derivative (1.8 mmol) were added and the mixture was stirred at room temperature for additional hours (24-78 hrs) needed to allow the reaction to reach its end. After completion of the reaction using TLC (100% ethyl acetate), the volatiles were removed under reduced pressure to dryness. The gum was dissolved in 20 ml DCM and the desired product Linoleoy-amido-ol (17-20) was obtained using column chromatography (dichloromethane/ethyl acetate=1:1, v/v, $I_2$).

Linoleoyl-L-Valinol (17)

Yield: 77%

$^1$H-NMR (CDCl$_3$, δ ppm): 8.02 (s, 1H), 5.63 (d, 2H), 4.10 (q, 1H), 3.69 (d, 2H), 2.88 (m, 1H), 2.77 (t, 2H), 2.17 (t, 2H), 2.00 (m, 4H), 1.64 (m, 2H), 1.31 (m, 9H)

ESI-MS M$^+$/e:

Linoleoyl-L-Isoleucinol (18)

$^1$H-NMR (CDCl$_3$, δ ppm): 5.7 (2H, d), 3.7 (m, 2H), 3.5 (q, 1H), 2.18 (m, 4H), 1.96 (m, 4H), 1.57 (3H, m), 1.33 (m, 6H), 1.29 (m, 10H), 1.06 (d, 3H), 0.96 (t, 6H)

Linoleoyl-L-Leucinol (19)

Yield: 76%

$^1$H-NMR(CDCl$_3$, δ ppm): 5.72 (d, 2H), 5.33 (d, 2H), 4.11 (q, 1H), 3.67 (m, 2H), 2.73 (t, 2H), 2.21 (m, 2H), 1.94 (m, 5H), 1.65 (m, 41-1), 1.26 (m, 14H), 1.10 (dt, 6H), 0.90 (t, 3H)

Linoleoyl-R-Phe-Glycinol (20)

Yield: 67%

$^1$H-NMR (CDCl$_3$, δ ppm): 7.1 (m, 5H), 6.2 (d, 2H), 5.2 (d, 2H), 4.9 (q, 1H), 3.7 (d, 2H), 2.6 (t, 2H), 2.18 (t, 2H), 1.96 (m, 4H), 1.35 (m, 8H), 1.2 (m, 8H), 0.96 (t, 3H).

Linoleoyl-R-Phe-Alaninol (21)

Yield: 67%

$^1$H-NMR(CDCl$_3$, δ ppm): 7.19 (m, 5H), 5.6 (d, 2H), 5.2 (d, 3H), 4.13 (q, 1H), 2.7 (t, 2H), 2.18 (t, 2H), 1.96 (q, 4H), 1.57 (m, 2H), 1.33 (m, 9H), 1.2 (m, 11H), 0.96 (t, 3H)

Linoleoyl-L-Phe-Alaninol (21)

Yield: 67%

$^1$H-NMR (CDCl$_3$, δ ppm): 7.1 (m, 5H), 5.65 (d, 2H), 5.2 (d, 2H), 4.1 (q, 1H), 2.65 (t, 2H), 2.18 (t, 2H), 1.96 (m, 4H), 1.4 (m, 20H), 0.96 (t, 3H)

Synthesis of the Oleoyl-Urethane (carbamate)amino-ols (Scheme-4)

General Procedure:

The synthesis of the carbamate derivatives followed the general procedure:

Scheme-4: synthesis of urethane derivatives of oleoyl alcohol-amino-ols (25-29)

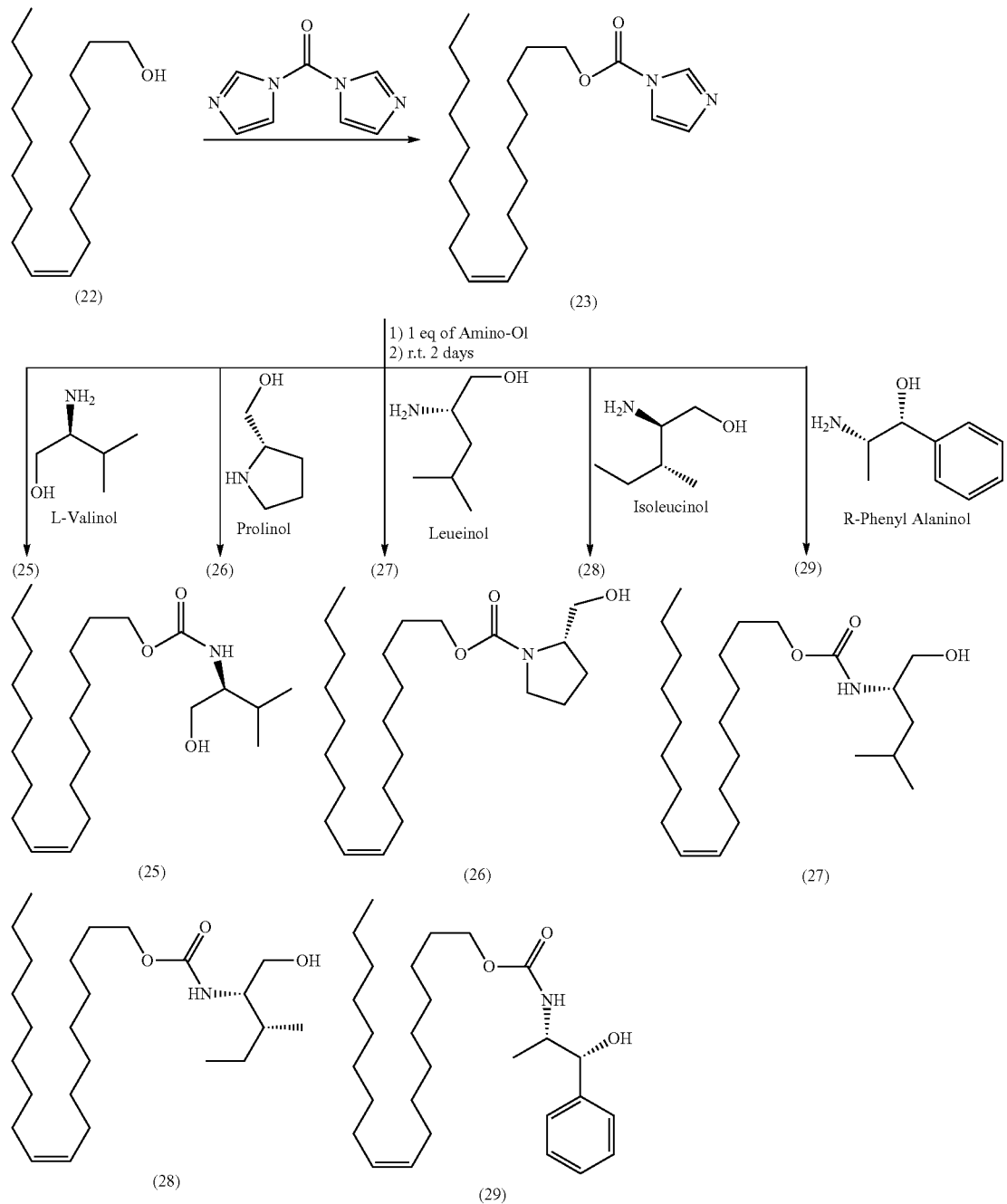

To Oleyl alcohol (22) (0.5 g, 1.86 mmol) were dissolved in 10 ml pyridine. While stirred at r.t., carbonyl diimidazole (CDI) (0.302 g, 1.86 mmol) were added. The reaction mixture was heated to 60° C. for 48 hrs. Reaction progress was followed using TLC (100% DCM). When the starting material disappeared as confirmed using TLC, 1 equivalent (1.86 mmol) of the desired amino-ol (L-Valinol, L-Prolinol, L-Leucinol, L-Isoleucinol, R-Phenylglycinol, L-Phenylalalinol, L-Alaninol) were added and the mixture was stirred for 2 days at room temperature. Reaction progress was followed by TLC (100% Ethyl acetate, $I_2$). After the reaction completion, the volatiles were removed under reduced pressure and the desired product was obtained using column chromatography (DCM/ethyl acetate=1:1; v/v). The fractions containing the desired product were pooled and volatiles were evaporated under reduced pressure.

Oleylcarbonyl-L-Valinol[(1-Hydroxymethyl-2-methyl-propyl)-carbamic acid octadec-9-enyl ester] (Scheme-4, 25)

To oleyl alcohol (22) (0.5 g, 1.58 mmol) in 5 ml pyridine, and while stirred at r.t., CDI (0.26 g, 1.58 mmol) was added. The reaction mixture was stirring at r.t for 48 hrs. Reaction was followed using TLC (100% DCM). When the starting material disappeared Valinol (0.162 g, 1.58 mmol) was added to the mixture was stirred for 1 week at room temperature. Reaction progress was followed by TLC (Eth. Ac100%). After the reaction was completed was the volatiles were removed under reduced pressure. The desired product Oleylcarbonyl-L-Valinol (25) was obtained using column chromatography (DCM/ethyl acetate.=1:1; v/v; $I_2$).

Yield: 67%

$^1$H-NMR (CDCl$_3$, δ ppm): 5.34 (dd, 2H), 4.04 (t, 2H), 3.68 (m, 1H), 3.78 (d, 2H), 2 (s, 1H), 0.87 (t, 3H), 1.27 (m, 14H), 1.57 (m, 2H), 0.94 (t, 6H), 1.83 (m, 6H), 2.54 (m, 1H).

Carbonyl diimidazol (0.26 g, 1.58 mmol) was added to a solution of Oleyl alcohol (0.5 g, 1.58 mmol) in 5 ml pyridine, and stirred at r.t for 48 hrs. Reaction was followed by TLC 100% DCM. Then (1.5 g, 14.9 mmol) of prolinol was added to the mixture, which was stirred for 1 week at r.t. Reaction was followed by TLC (100% Eth. Ac.). Solvent was evaporated and mixture was purified by CC (DCM/ethyl acetate.=1:1; v/v, $I_2$). NMR result showed pure product of (1-Hydroxymethyl-2-methyl-propyl)-carbamic acid octadec-9-enyl ester.

Yield: 67%

Oleylcarbonyl-L-Prolinol (Scheme-4, 26)

$^1$H-NMR (CDCl$_3$, δ ppm):
5.2 (d, 2H), 4.08 (q, 2H), 3.6 (t, 3H), 2.18 (t, 2H), 1.96 (t, 8H), 1.57 (m, 2H), 1.3 (m, 24H), 0.96 (t, 3H)

Yield: 67%

Preparation of Oleoylamine-D/L-Lactide[2-Hydroxy-N-octadec-9-enyl-propionamide] (31), (32)

(L)-2-Hydroxy-N-octadec-9-enyl-propionamide (31)

Scheme-5: Synthesis of the oleoyl-lactides (31) and (32).

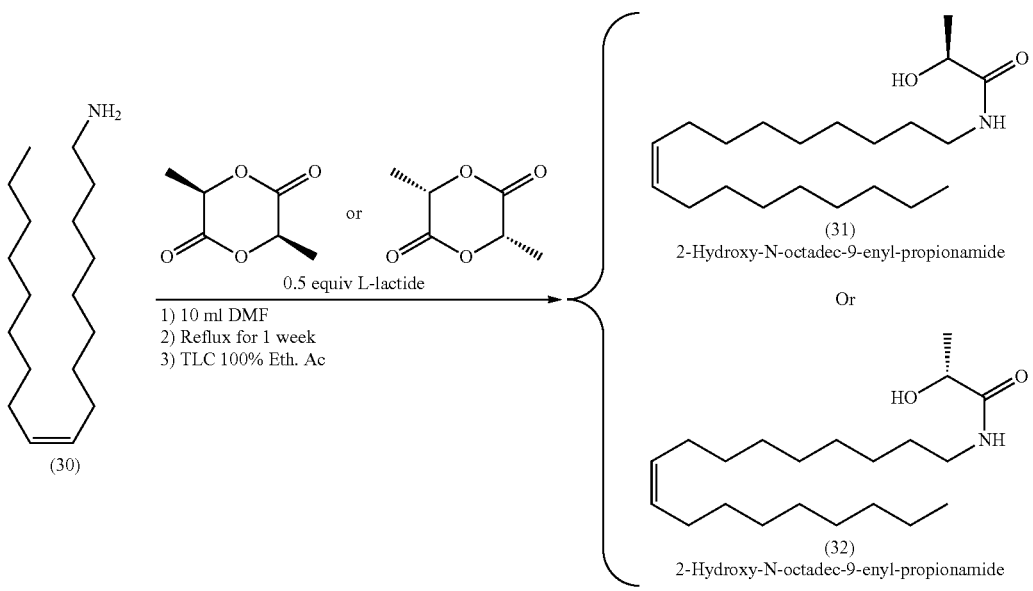

(300 mg, 2.08 mmol) L-Lactide was added to a solution of (1.6 g, 4.16 mmol) of oleyl amine in 10 ml DMF. The reaction mixture was heated to 80° C. for (34 hrs). Thorough out this period of time the color turned from colorless to yellow. Reaction was followed by TLC (100% Eth. Ac.). When reaction was over, the product was obtained by column chromatography (CHCl$_3$/Hexane=20:80; v/v).

Yield=85%

$^1$H-NMR (CDCl$_3$, δ ppm): 0.96 (t, 3H), 1.25-1.39 (m, 16H), 1.43-1.46 (d, 3H), 1.6-1.7 (m, 4H), 2-2.1 (dt, 4H), 3.2 (dt, 2H), 4.2 (q, 1H), 5.32-5.35 (dt, 2H).

(D)-2-Hydroxy-N-octadec-9-enyl-propionamide (32)

This compound was synthesized using the same procedure used for the synthesis of (31).

Yield=85%

$^1$H-NMR (CDCl$_3$, δ ppm): 0.96 (t, 3H), 1.25-1.39 (m, 16H), 1.43-1.46 (d, 3H), 1.6-1.7 (m, 4H), 2-2.1 (dt, 4H), 3.2 (dt, 2H), 4.2 (q, 1H), 5.32-5.35 (dt, 2H).

Synthesis of Saturated Fatty Acid Conjugates

Scheme-9: General scheme for conjugating of sturated fatty acid to the amino-ol derivatives

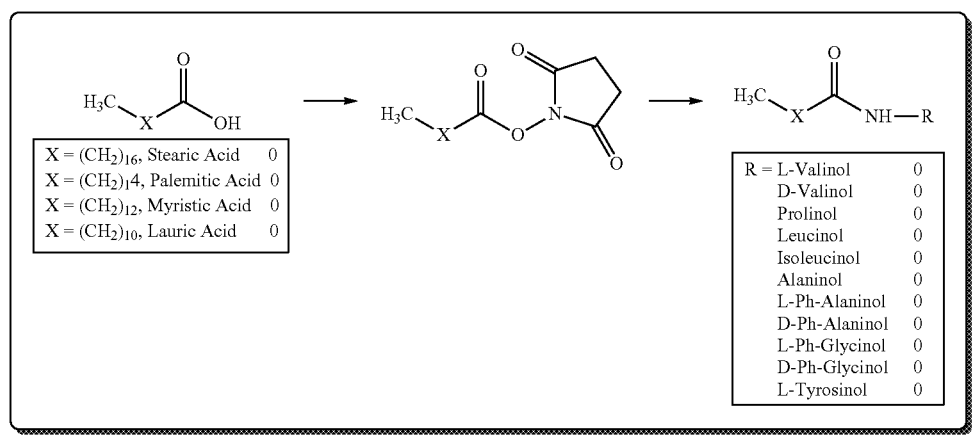

Synthesis of Palmitoylvalinol[Hexadecanoic acid (1-hydroxymethyl-2-methyl-propyl)-amide] (37) and Palmitoylprolinol[1-(2-Hydroxymethyl-pyrrolidin-1-yl)-hexadecan-1-one] (38)

Palmitic acid (0.5 g, 1.95 mmol) dissolved in 5 ml of dry pyridine to which 1.2 equivalents of dry TEA, DCC (0.442 g, 2.1441=01) and NHS (0.2467, g 2.144 mmol). The reaction mixture was stirred at 24 hr at room temperature for O.N. Reaction progress was followed using TLC (5% MeOH/CHCl$_3$) When the starting martial was fully converted to the active—NHS intermediate, Valinol (5) (0.201 g, 1.95 mmol) or (0.197 g, 1.95 mmol) was added and the reaction was allowed to stand at room temperature for the time needed for completion. TLC (100% Eth.Ac.). When the reaction was completed pyridine was removed under reduced pressure and the gum was dissolved in 20 ml DCM and purified on column chromatography using (Ethyl acetate:DCM; 1:1). Correct fractions were collected and volatiles were removed to dryness under reduced pressure to afford the desired product as white solid.

Palmitoylvalinol; [Hexadecanoic acid (1-hydroxymethyl-2-methyl-propyl)-amide] (37)

Yield: 36.4%

$^1$H-NMR (CDCl$_3$, δ ppm):

5.59 (s, 1H), 3.8 (d, 2H), 3.7 (q, 1H) 2.60 (m, 1H), 2.24 (t, 2H), 1.90 (m, 2H), 1.63 (m, 2H), 1.27 (m, 22) 0.97 (q, 6H), 0.98 (t, 3H)

Palmitoylprolinol; [1-(2-Hydroxymethyl-pyrrolidin-1-yl)-hexadecan-1-one] (38)

Yield: 60.4%

$^1$H-NMR (CDCl$_3$, δ ppm):

5.21 (s, 1H), 4.23 (q, 2H), 3.67 (t, 1H), 3.52 (m, 1H), 2.31 (t, 2H), 1.98 (m, 2H), 1.94 (m, 2H), 1.61 (m, 2H), 1.30 (m, 24H), 0.89 (t, 3H)

Scheme-10: synthesis for palmitic acid derivatives: Pathway-A: synthesis of Plamitoyl-Valinol (37); Pathway-B: synthesis of Plamitoyl-Prolinol (38).

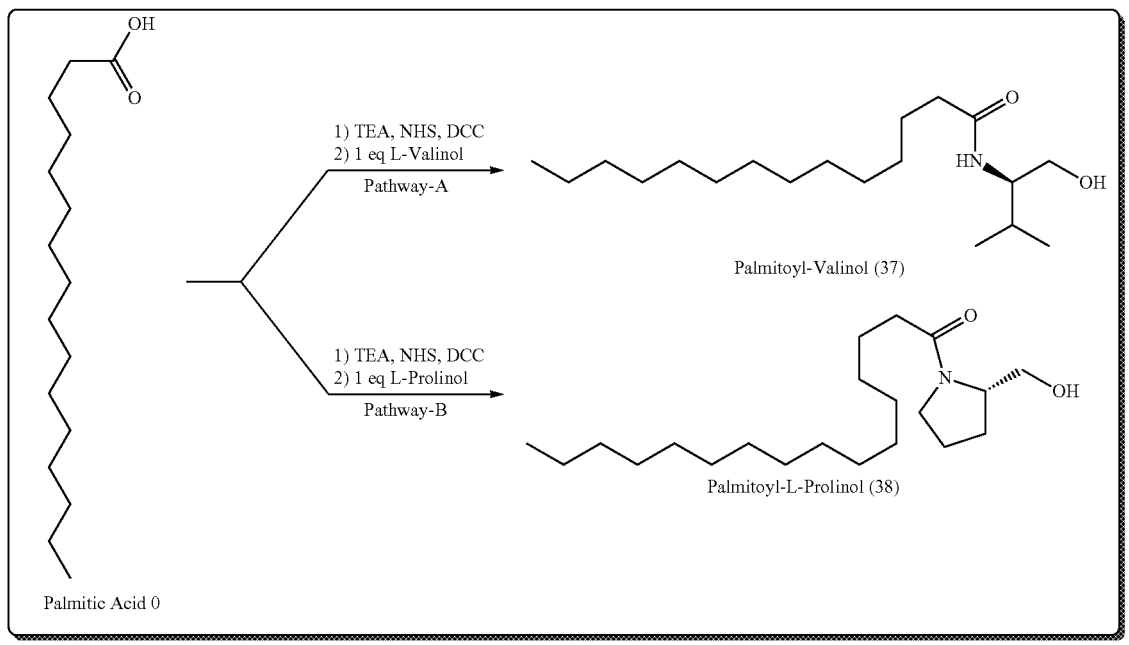

Synthesis of Stearic Acid Derivatives

Stearoyl-Prolinol (39)

To a solution of stearic acid (0.5 g 1.758 mmol) in 5 ml dry pyridine (kept over KOH) (0.399 g, 1.93 mmol) and NHS (0.223 g, 1.93 mmol) were added and dissolved in, stirred for 24 hr at room temperature. Reaction was followed by TLC 5% MeOH. Prolinol (0.197 g, 1.949 mmol) were added and the mixture was stirred at room temperature for three days was added to the mixture, and stirred at room temperature. Reaction controlled by TLC (100% Ethyl acetate). At the end of the reaction, volatiles were removed under reduced pressure and the mixture was dissolved in 30 ml DCM and DCU precipitate was filtrated off and the desired product was purified using column chromatography (ethyl acetate/DCM=1:1).
Yield:
$^1$H-NMR (CDCl$_3$, δ ppm):
4.24 (d, 2H), 3.67 (t, 1H), 3.51 (t, 2H), 2.30 (t, 2H), 2.04 (m, 2H), 1.88 (q, 2H), 1.65 (m, 2H), 1.27 (m, 28H), 0.88 (t, 3, H)

Stearoyl-Valinol (40)

Synthesized following similar procedure used for the Stearoyl-Valinol (40).
Yield:
$^1$H-NMR (CDCl$_3$, δ ppm):
5.62 (s, 1H), 3.76 (d, 2H), 2.66 (q, 1H), 2.25 (m, 1H), 1.91 (t, 2H) 1.67 (m, 2H) 1.28 (m, 28H), 0.99 (q, 9H)

Synthesis of Myristic Acid Derivatives

Myristoyl-Valinole (41)

Synthesized following similar procedure used for the Stearoyl-Valinol (40).

Yield: 39.6%
$^1$H-NMR (CDCl$_3$, δ ppm):
4.09 (d, 2H), 3.51 (q, 1H), 2.26 (m, 11-1), 1.96 (t, 2H), 1.68 (m, 2H), 1.35 (m, 2H), 1.16 (m, 18H), 0.99 (m, 6H), 0.92 (t, 3H)

Synthesis of Laurie Acid Derivatives

Lauroyl-Valinole (42)

Synthesized following similar procedure used for the Stearoyl-Valinol (40).
Yield: 67.4%
$^1$H-NMR (CDCl$_3$, δ ppm):
5.62 (s, 1H), 3.75 (d, 2H), 3.67 (d, 1H), 2.24 (m, 1H), 1.90 (t, 2H), 1.65 (m, 2H), 1.27 (m, 16H), 0.97 (m, 6H), 0.90 (t, 3H)

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:
1. A method for treating or reducing the severity of obesity, increasing or facilitating weight loss, suppressing, inhibiting or reducing appetite, decreasing food consumption, or improving cognitive function in a subject, comprising:
administering to a subject in need thereof a compound selected from the group consisting of

(17)
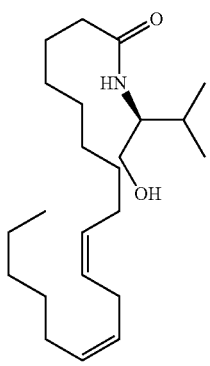
(18)
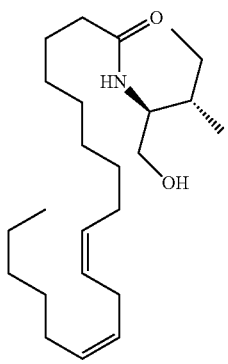
(19)
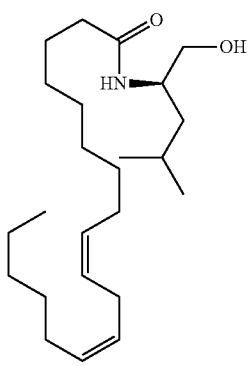
(20)
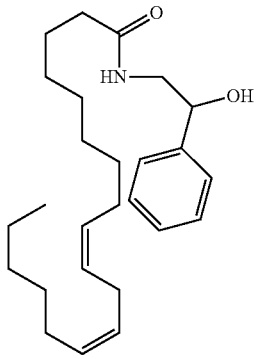
(21)
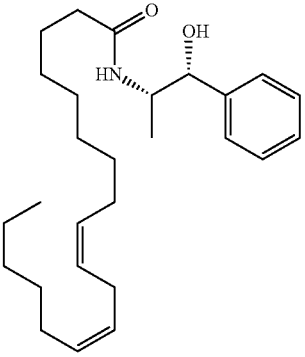
(25)
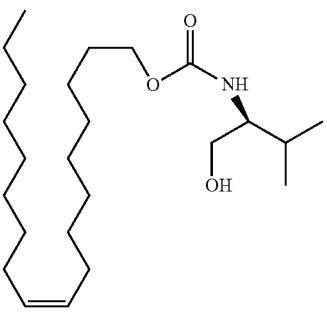
(26)
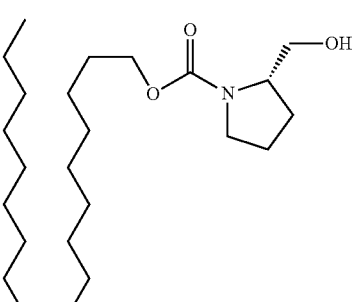
(27)
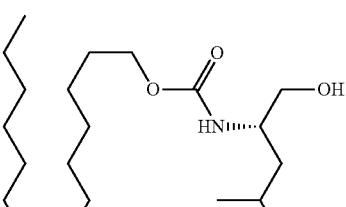
(25)
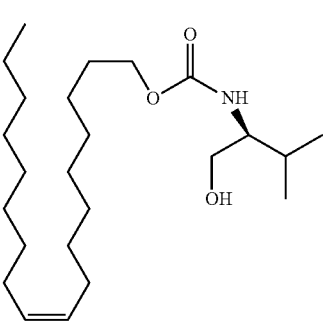

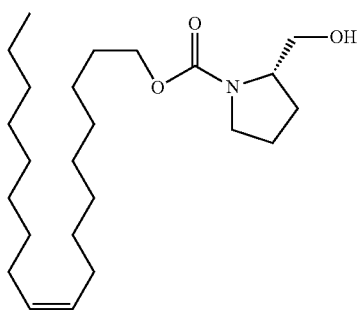
(26)

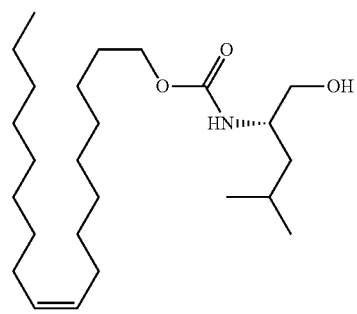
(27)

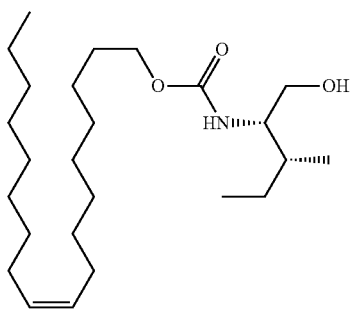
(28)

and

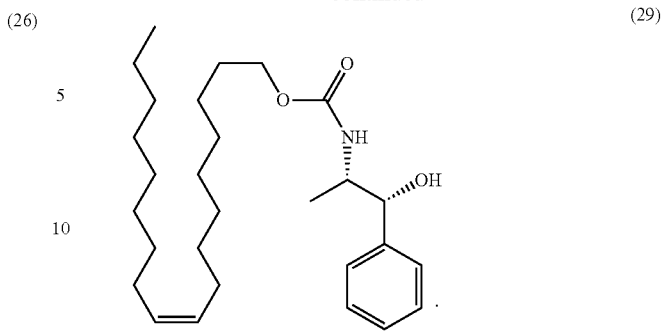
(29)

2. A method for suppressing, inhibiting or reducing appetite, decreasing food consumption, or improving cognitive function in a subject, comprising:
administering to a subject in need thereof a formula 10:

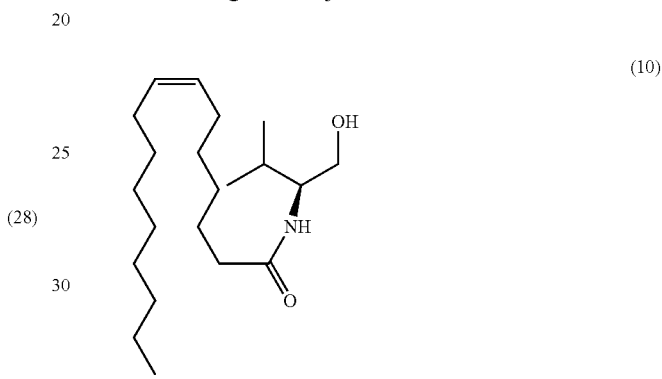
(10)

3. The method of claim 1, for treating obesity in a subject.
4. The method of claim 1, for increasing or facilitating weight loss in a subject.
5. The method of claim 1, for suppressing, inhibiting or reducing appetite in a subject.

* * * * *